US006787145B1

(12) United States Patent
Tsarev et al.

(10) Patent No.: US 6,787,145 B1
(45) Date of Patent: *Sep. 7, 2004

(54) RECOMBINANT PROTEINS OF A PAKISTANI STRAIN OF HEPATITIS E AND THEIR USE IN DIAGNOSTIC METHODS AND VACCINES

(75) Inventors: Sergei A. Tsarev, Rockville, MD (US); Suzanne U. Emerson, Rockville, MD (US); Robert H. Purcell, Boyds, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/724,475

(22) Filed: Nov. 28, 2000

Related U.S. Application Data

(63) Continuation of application No. 08/809,523, filed as application No. PCT/US95/13102 on Oct. 3, 1995, now Pat. No. 6,207,416, which is a continuation-in-part of application No. 08/316,765, filed on Oct. 3, 1994, which is a continuation-in-part of application No. 07/947,263, filed on Sep. 18, 1992, now abandoned.

(51) Int. Cl.[7] .............................................. A61K 39/29
(52) U.S. Cl. ............................... 424/228.1; 424/189.1; 424/184.1; 530/350; 435/69.3
(58) Field of Search .......................... 424/228.1, 189.1, 424/184.1; 530/350; 435/69.3

(56) References Cited

U.S. PATENT DOCUMENTS

| 5,686,239 A | 11/1997 | Reyes et al. ................... 435/5 |
| 5,741,490 A | 4/1998 | Reyes et al. ............. 424/189.1 |
| 5,770,689 A | 6/1998 | Reyes et al. ................. 530/324 |
| 6,287,759 B1 * | 9/2001 | Tsarev et al. .................. 435/5 |

FOREIGN PATENT DOCUMENTS

| WO | WO 91/15603 | 10/1991 |
| WO | WO 93/14116 | 7/1993 |
| WO | WO 94/06913 | 3/1994 |
| WO | WO 95/08632 | 3/1995 |
| WO | WO 95/17501 | 6/1995 |
| WO | WO 96/12807 | 5/1996 |

OTHER PUBLICATIONS

He, J. et al. (1995) *J. Clin. Microbiol*, 33:3308–3311.
Panda et al. (1995) "An Indian Strain of Hepatitis E Virus (HEV): Cloning, Sequence, and Express of Structural Region and Antibody Responses in Sera from Individuals from an Area of High–Level HEV Endemicity" *Journal of Clinical Microbiology*, vol. 33, No. 10, p. 2653–2659.

Yin et al. (1994) A New Chinese Isolate of Hepatitis E Virus: Comparison with Strains Recovered from Different Geographical Regions, *Virus Genes* 9:1, 22–32.
Dawson et al., "Solid–Phase Enzyme–Linked Immunosorbent Assay For Hepatitis E Virus IgG and IgM Antibodies Utilizing Recombinant Antigens And Synthetic Peptides," *J. Virol. Methods*, 38:175–186 (1992).
Uchida et al., "Hepatitis E Virus: cDNA Cloning and Expression," *Microbiol, Immunol.*, 36:67–79 (1992).
Skidmore et al., "Hepatitis E Virus: The Cause Of A Waterbourne Hepatitis Outbreak," *J. Med. Virol.*, 37:58–60 (1992).
Saeed et al., "ELISA For Diagnosis Of Acute Sporadic Hepatitis E," *Lancet*, 339:882 (1992).
Aye et al., "Complete Nucleotide Sequence Of A Hepatitis E Virus Isolated From The Xinjiang Epidemic (1986–1988) Of China," *Nucleic Acids Res.*, 20:3512 (1992).
Hyams et al., "Acute Sporadic Hepatitis E In Sudanese Children: Analysis Based On A New Western Blot Assay," *J. Infect. Dis.*, 165:1001–1005 (1992).
Tsarev et al., "Characterization Of A Prototype Strain Of Hepatitis E Virus," *Proc. Nat. Acad. Sci.*, 89:559–563 (1992).
Ichikawa et al., "Cloning and Expression of cDNAs From Enterically–Transmitted Non–A, Non–B Hepatitis Virus," *Microbiol. Immunol.*, 35:535–543 (1992).
Purdy et al., "Expression Of A Hepatitis E Virus (HEV)–trpE Fusion Protein Containing Epitopes Recognized By Antibodies In Sera From Human Cases And Experimentally Infected Primates," *Archives Virol.*, 123:335–349 (1992).
Favorov et al., Serologic Identificaton Of Hepatitis E Virus Infections In Epidemic And Endemic Settings, *J. Med. Virol.*, 36:246–250 (1992).
Reyes et al., "Isolation Of A cDNA From The Virus Responsible For Enterically Transmitted Non–A, Non–B Hepatitis," *Science*, 247:1335–1339 (1992).
Tam et al., "Hepatitis E Virus (HEV): Molecular Cloning And Sequencing Of The Full–Length Viral Genome," *Virology*, 185:120–131 (1992).
Goldsmith et al., "Enzyme–Linked Immunosorbent Assay For Diagnosis Of Acute Sporadic Heptatis E In Egyptian Children," *Lancet*, 339:328–331 (1992).

(List continued on next page.)

*Primary Examiner*—James Housel
*Assistant Examiner*—Stacy B. Chen
(74) *Attorney, Agent, or Firm*—Knobbe, Martens, Olson & Bear, LLP

(57) ABSTRACT

A strain of hepatitis E virus from Pakistan (SAR-55) implicated in an epidemic of enterically transmitted non-A, non-B hepatitis, now called hepatitis E, is disclosed. The invention relates to the expression of the whole structural region of SAR-55, designated open reading frame 2 (ORF-2), in a eukaryotic expression system. The expressed protein is capable of forming HEV virus-like particles which can serve as an antigen in diagnostic immunoassays and as an immunogen or vaccine to protect against infection by hepatitis E.

16 Claims, 29 Drawing Sheets

OTHER PUBLICATIONS

Fry et al., "Hepatitis E Virus (HEV): Strain Variation In The Nonstructural Gene Region Encoding Consensus Motifs For An RNA–Dependent RNA Polymerase And An ATP/GTP Binding Site," *Virus Genes,* 6:173–185 (1992).

He, J. et al., "Expression and Diagnostic Utility of Hepatitis E Virus Putative Structural Proteins Expressed in Insect Cells," *J. Clin. Micro.,* 31:2167–2173 (1993).

Purdy M.A. et al., "Preliminary Evidence that a trpE–HEV Fusion Protein Projects Cynomolgus Macaques Against Challenge With Wild–Type Hepatitis E Virus (HEV)," *J. Med. Virology,* 41:90–94 (1993).

Tsarev, S. et al., Variation In Course Of Hepatitis E In Experimentally Infected Cynomolgus Monkeys (1993) *J. Infect. Dis.,* 167:1302–1306.

Tsarev, S. et al., Infectivity Titration Of A Prototype Strain Of Hepatitis E Virus Cynomolgus Monkeys (1994) *J. Med. Virol.,* 43:135–142.

Reyes et al. (1991) "Hepatitis E Virus (HEV): Epitope Mapping and Detection of Strain Variation", Elsevier Science Publisher Shikata et al. eds., Chapter 43:237–245.

Mast E. et al. (1996) *Ann Rev. Med.,* 47:257–266.

Salynn Boyles (1995) *Vaccine Weekly.*

* cited by examiner

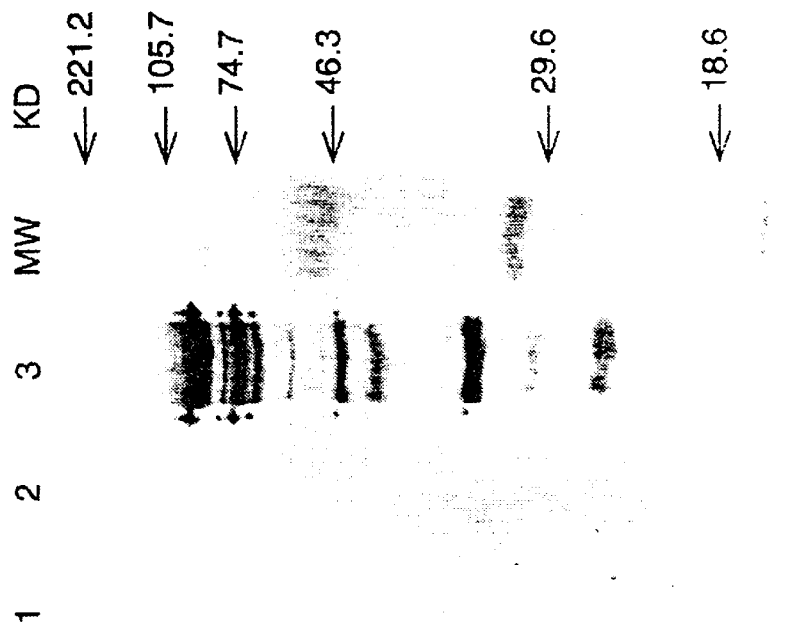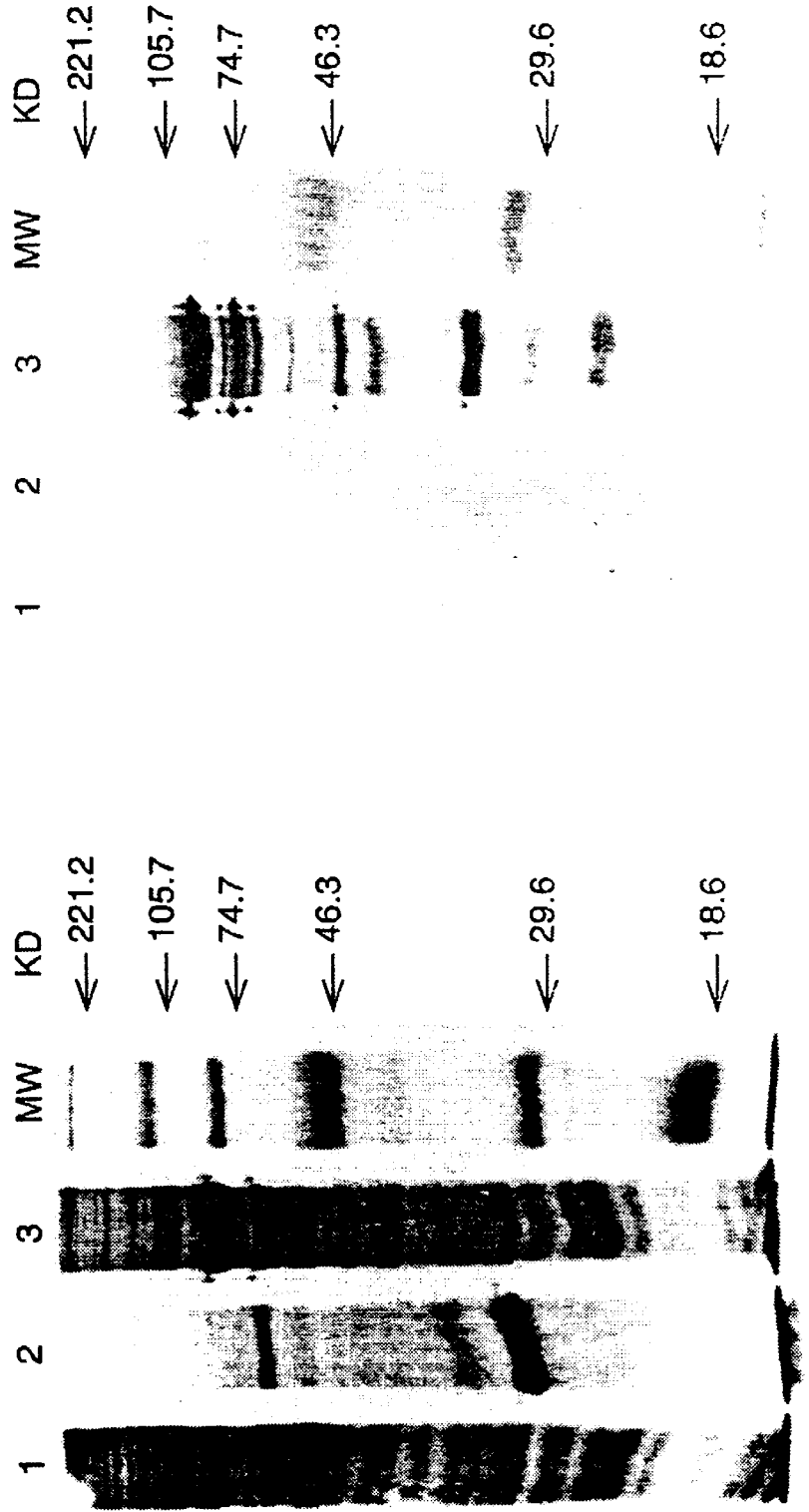

FIG. 3A
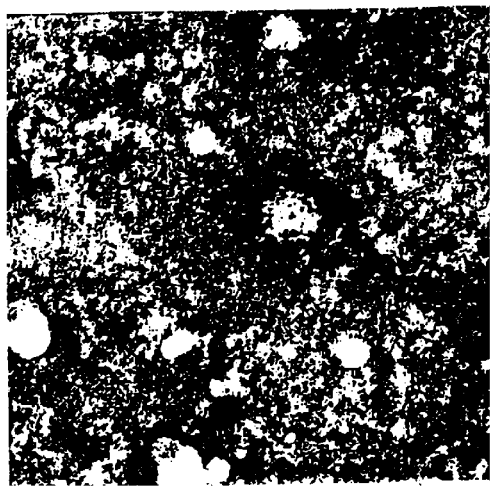
FIG. 3A'
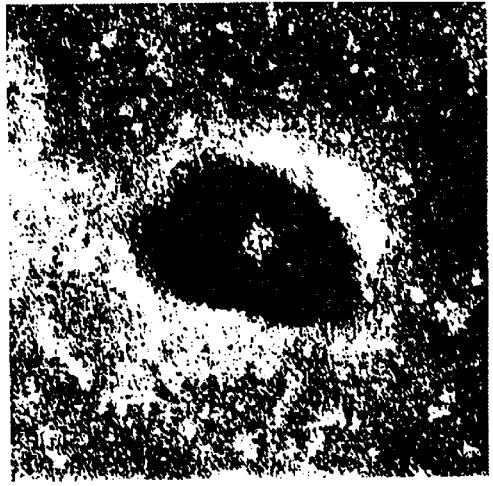
FIG. 3A"
FIG. 3A'''
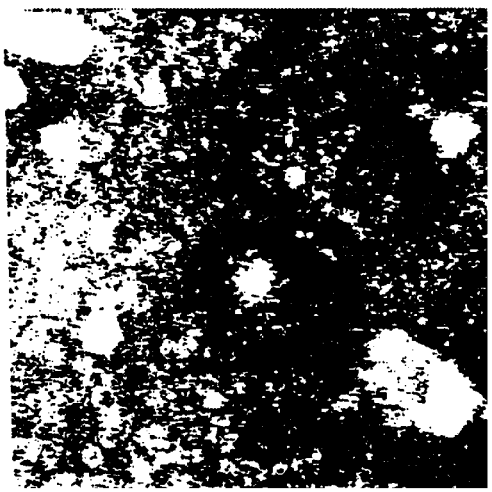

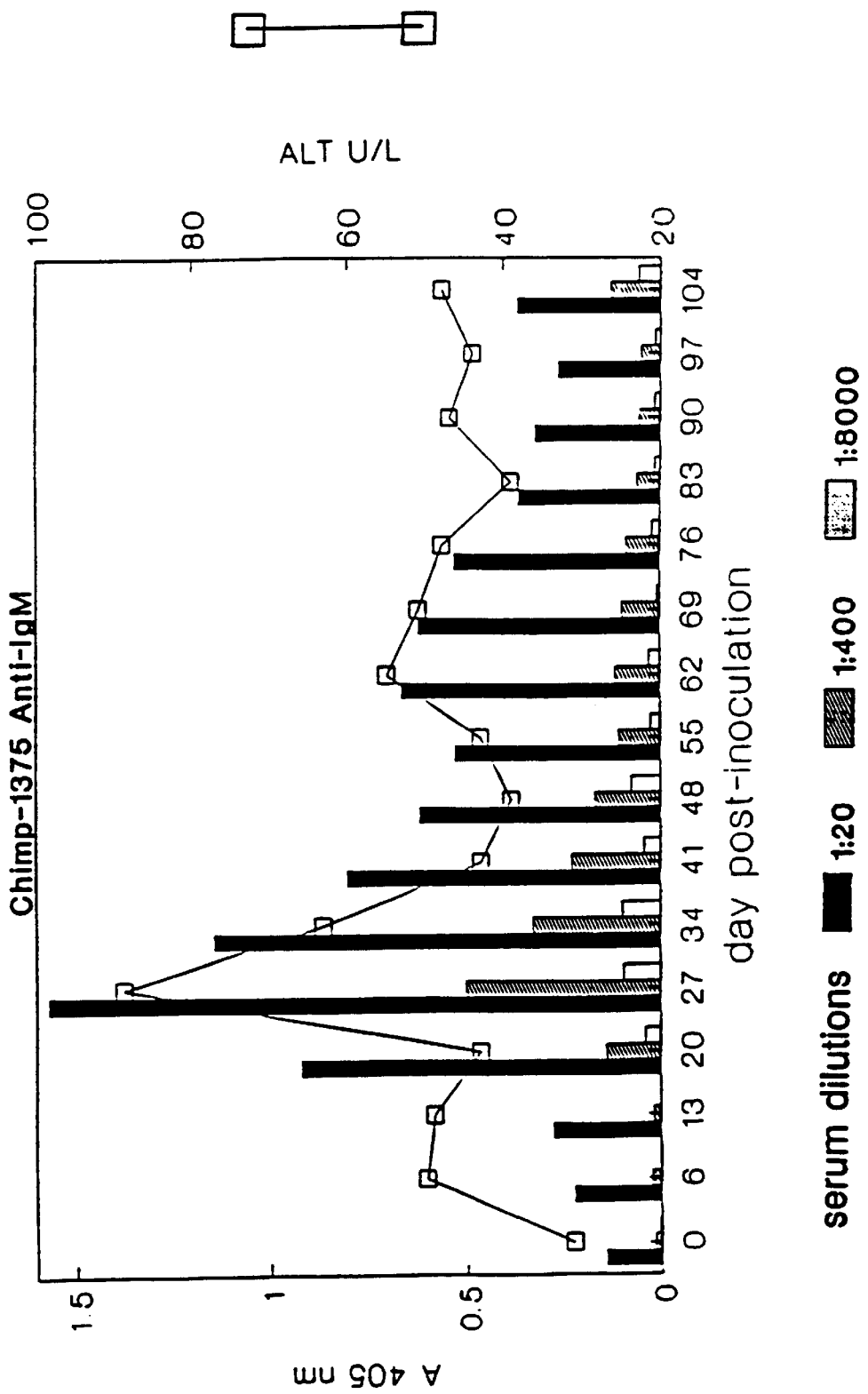

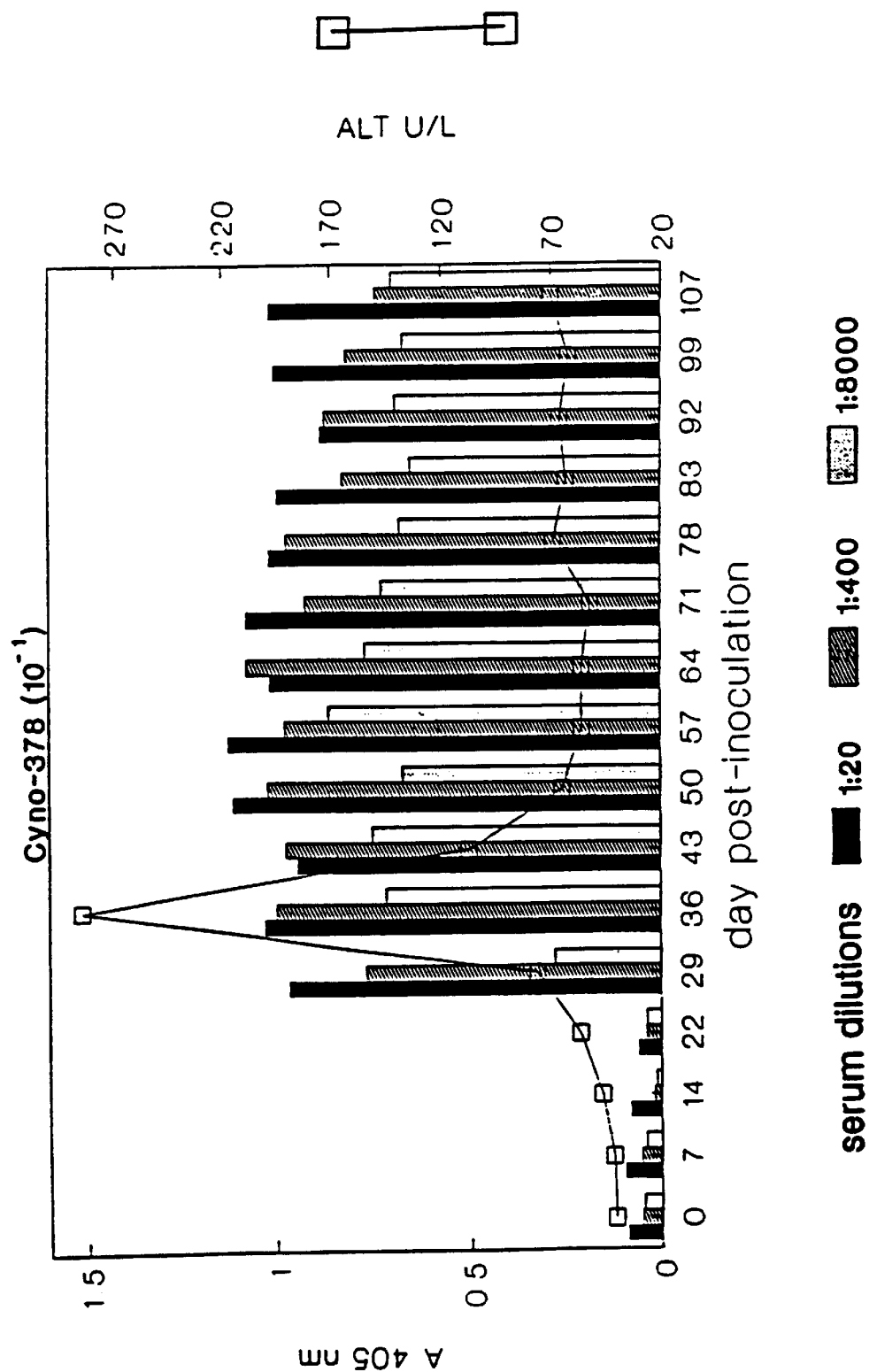

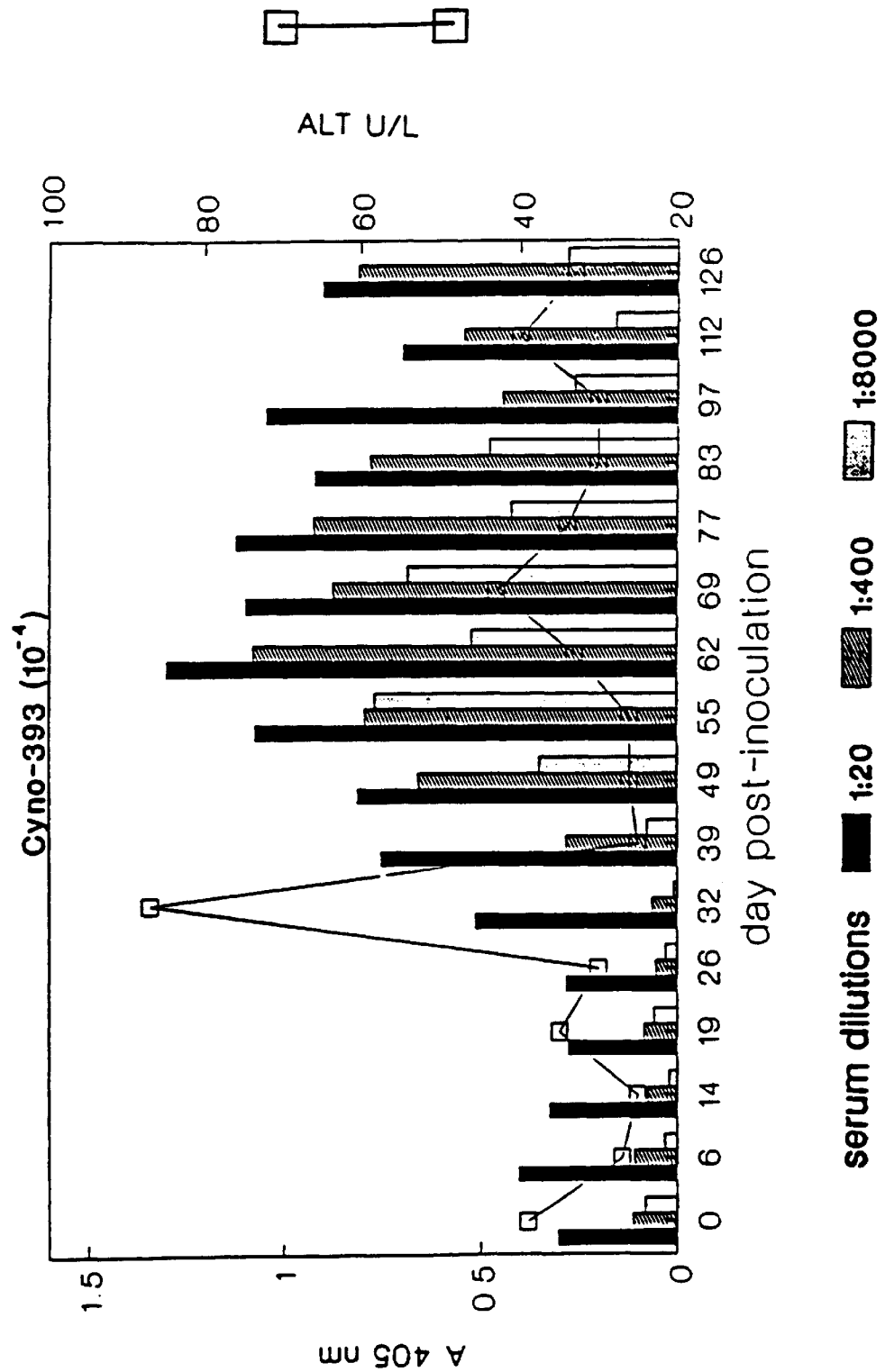

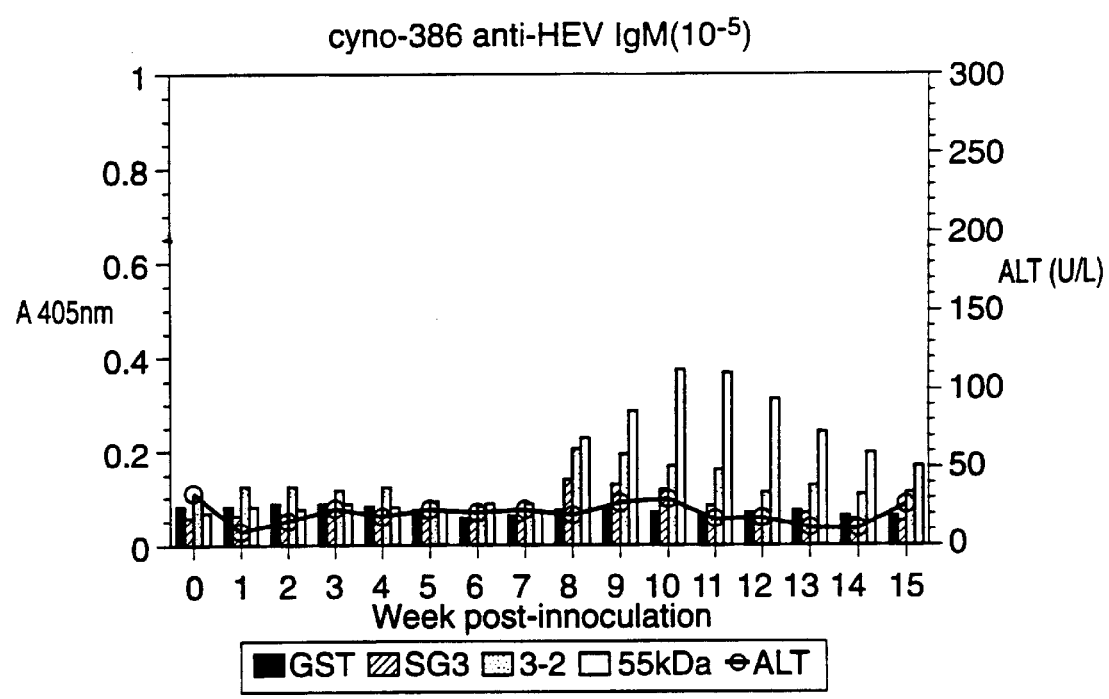

RECOMBINANT PROTEINS OF A PAKISTANI STRAIN OF HEPATITIS E AND THEIR USE IN DIAGNOSTIC METHODS AND VACCINES

This is a continuation of application Ser. No. 08/809,523 filed May 5, 1997 now U.S. Pat. No. 6,207,416, which is a national filing under 35 U.S.C. §371 of PCT application PCT/US95/13102, filed on Oct. 3, 1995, which is a continuation-in-part of Ser. No. 08/316,765, filed on Oct. 3, 1994, which is a continuation-in-part of Ser. No. 07/947,263, filed on Sep. 18, 1992, now abandoned.

FIELD OF INVENTION

The invention is in the field of hepatitis virology. More specifically, this invention relates to recombinant proteins derived from an enterically transmitted strain of hepatitis E from Pakistan, SAR-55, and to diagnostic methods and vaccine applications which employ these proteins.

BACKGROUND OF INVENTION

Epidemics of hepatitis E, an enterically transmitted non-A/non-B hepatitis, have been reported in Asia, Africa and Central America (Balayan, M. S. (1987), Soviet Medical Reviews, Section E, Virology Reviews, Zhdanov, 0-V. M. (ed), Chur, Switzerland: *Harwood Academic Publishers*, vol. 2, 235–261; Purcell, R. G., et al. (1988) in Zuckerman, A. J. (ed), "Viral Hepatitis and Liver Disease", New York: Alan R. Liss, 131–137; Bradley, D. W. (1990), *British Medical Bulletin*, 46:442–461; Ticehurst, J. R. (1991) in Hollinger, F. B., Lemon, S. M., Margolis, H. S. (eds): "Viral Hepatitis and Liver Disease", Williams and Wilkins, Baltimore, 501–513). Cases of sporadic hepatitis, presumed to be hepatitis E, account for up to 90% of reported hepatitis in countries where hepatitis E virus (HEV) is endemic. The need for development of a serological test for the detection of anti-HEV antibodies in the sera of infected individuals is widely recognized in the field, but the very low concentration of HEV excreted from infected humans or animals made it impossible to use such HEV as the source of antigen for serological tests and although limited success was reported in propagation of HEV in cell culture (Huang, R. T. et al. (1992), *J. Gen. Virol.*, 73:1143–1148), cell culture is currently too inefficient to produce the amounts of antigen required for serological tests.

Recently, major efforts worldwide to identify viral genomic sequences associated with hepatitis E have resulted in the cloning of the genomes of a limited number of strains of HEV (Tam, A. W. et al. (1991), *Virology*, 185:120–131; Tsarev, S. A. et al. (1992), *Proc. Natl. Acad. Sci. USA*, 89:559–563; Fry, K. E. et al. (1992), *Virus Genes*, 6:173–185). Analysis of the DNA sequences have led investigators to hypothesize that the HEV genome is organized into three open reading frames (ORFs) and to hypothesize that these ORFs encode intact HEV proteins.

A partial DNA sequence of the genome of an HEV strain from Burma (Myanmar) is disclosed in Reyes et al., 1990, *Science*, 247:1335–1339. Tam et al., 1991, and Reyes et al., PCT Patent Application WO91/15603 published Oct. 17, 1991 disclose the complete nucleotide sequence and a deduced amino acid sequence of the Burma strain of HEV. These authors hypothesized that three forward open reading frames (ORFs) are contained within the sequence of this strain.

Ichikawa et al., 1991, *Microbiol. Immunol.*, 35:535–543, discloses the isolation of a series of clones of 240–320 nucleotides in length upon the screening of a λgt11 expression library with sera from HEV-infected cynomolgus monkeys. The recombinant protein expressed by one clone was expressed in *E. coli*. This fusion protein is encoded by the 3' region of ORF-2 of the Myanmar strain of HEV.

The expression of additional proteins encoded within the 3' region of ORF-2 of a Mexican strain of HEV and of a Burmese strain of HEV is described in Yarbough et al., 1991 *J. Virology*, 65:5790–5797. This article describes the isolation of two cDNA clones derived from HEV. These clones encode the proteins in the 3' region of ORF-2. The clones were expressed in *E. coli* as fusion proteins.

Purdy et al., 1992, *Archives of Virology*, 123:335–349, and Favorov et al., 1992, *J. of Medical Virology*, 36:246–250, disclose the expression of a larger ORF-2 protein fragment from the Burma strain in *E. coli*. These references, as well as those previously discussed, only disclose the expression of a portion of the ORF-2 gene using bacterial expression systems. Successful expression of the full-length ORF-2 protein has not been disclosed until the present invention.

Comparison of the genome organization and morphological structure of HEV to that of other viruses revealed that HEV is most closely related to the caliciviruses. Of interest, the structural proteins of caliciviruses are encoded by the 3' portion of their genome (Neil, J. D. et al. (1991) *J. Virol.*, 65:5440–5447; and Carter, M. J. et al. (1992), *J. Arch. Virol.*, 122:223–235) and although there is no direct evidence that the 3' terminal part of the HEV genome also encodes the structural proteins, expression of certain small portions of the 3' genome region in bacterial cells resulted in production of proteins reactive with anti-HEV sera in ELISA and Western blots (Yarborough, et al., (1991); Ichikawa et al. (1991); Favorov et al. (1992) and Dawson, G. J. et al. (1992) *J. Virol. Meth*; 38:175–186). However, the function of ORF-2 protein as a structural protein was not proven until the present invention.

The small proteins encoded by a portion of the ORF-2 gene have been used in immunoassay to detect antibodies to HEV in animal sera. The use of small bacterially expressed proteins as antigens in serological immunoassays has several potential drawbacks. First, the expression of these small proteins in bacterial cells often results in solubility problems and in non-specific cross-reactivity of patients' sera with *E. coli* proteins when crude *E. coli* lysates are used as antigens in immunoassays (Purdy et al. (1992)). Second, the use of Western blots as a first-line serological test for anti-HEV antibodies in routine epidemiology is impractical due to time and cost constraints. An ELISA using small-peptides derived from the 3'-terminal part of the HEV genome resulted in the detection of only 41% positives from known HEV-infected patients. Third, it has been shown that for many viruses, including Picornaviridae which is the closest family to the Caliciviridae, important antigenic and immunogenic epitopes are highly conformational (Lemon, S. M. et al. (1991), in Hollinger, F. B., Lemon, S. M., Margolis, H. S. (eds): "Viral Hepatitis and Liver Disease", Williams and Wilkins, Baltimore, 20–24). For this reason, it is believed that expression in a eukaryotic system of a complete ORF encoding an intact HEV gene would result in production of a protein which could form HEV-virus-like particles. Such a complete ORF protein would have an immunological structure closer to that of native capsid protein(s) than would the above-noted smaller proteins which represent only portions of the structural proteins of HEV. Therefore, these complete ORF proteins would likely serve as a more representative antigen and a more efficient immunogen than the currently-used smaller proteins.

SUMMARY OF INVENTION

The present invention relates to an isolated and substantially pure preparation of a human hepatitis E viral strain SAR-55.

The invention also relates to an isolated and substantially pure preparation of the genomic RNA of the human hepatitis E viral strain SAR-55.

The invention further relates to the cDNA of the human hepatitis E viral strain SAR-55.

It is an object of this invention to provide synthetic nucleic acid sequences capable of directing production of recombinant HEV proteins, as well as equivalent natural nucleic acid sequences. Such natural nucleic acid sequences may be isolated from a cDNA or genomic library from which the gene capable of directing synthesis of the HEV proteins may be identified and isolated. For purpose of this application, nucleic acid sequence refers to RNA, DNA, cDNA or any synthetic variant thereof which encodes for protein.

The invention further relates to a method for detection of the hepatitis E virus in biological samples based on selective amplification of hepatitis E gene fragments utilizing primers derived from the SAR-55 cDNA.

The invention also relates to the use of single-stranded antisense poly-or oligonucleotides derived from the SAR-55 cDNA to inhibit the expression of hepatitis E genes.

The invention also relates to isolated and substantially purified HEV proteins and variants thereof encoded by the HEV genome of SAR-55 or encoded by synthetic nucleic acid sequences and in particular to recombinant proteins encoded by at least one complete open reading frame of HEV.

The invention also relates to the method of preparing recombinant HEV proteins derived from an HEV genomic sequence by cloning the nucleic acid and inserting the cDNA into an expression vector and expressing the recombinant protein in a host cell.

The invention also relates to the use of the resultant recombinant HEV proteins as diagnostic agents and as vaccines.

The present invention also encompasses methods of detecting antibodies specific for hepatitis E virus in biological samples. Such methods are useful for diagnosis of infection and disease caused by HEV, and for monitoring the progression of such disease. Such methods are also useful for monitoring the efficacy of therapeutic agents during the course of treatment of HEV infection and disease in a mammal.

This invention also relates to pharmaceutical compositions for use in prevention or treatment of Hepatitis E in a mammal.

DESCRIPTION OF FIGURES

FIGS. 2A and 2B are sodium dodecyl sulfate-polyacrylamide gels (SDS-PAGE) in which cell lysates of insect cells infected with wild-type baculovirus or recombinant baculovirus (containing the gene encoding ORF-2) were either stained with Coomassie blue (A) or subjected to Western blotting with serum of an HEV-infected chimp (B). In both FIGS. 2A and 2B, lane 1 contains total cell lysate of noninfected SF-9 cells; lane 2 contains lysate of cells infected with wild-type baculovirus; lane 3 contains lysate of cells infected with recombinant baculovirus and lane 4 contains molecular weight markers.

FIGS. 5A–D show the results of an ELISA using as the antigen, recombinant ORF-2 which was expressed from insect cells containing the gene encoding the complete ORF-2. Serum IgG or IgM anti-HEV levels were determined over time following inoculation of two chimpanzees with HEV.

FIGS. 6A–J show a comparison of ELISA data obtained using as the antigen the recombinant complete ORF-2 protein derived from SAR-55 as the antigen vs. a recombinant partial ORF-2 protein derived from the Burma strain of HEV (Genelabs).

FIGS. 8A–E show anti-HEV IgM ELISA and ALT values for positive cynomolgus monkeys inoculated with ten-fold serial dilutions (indicated in parenthesis at the top of each panel) of the 10% fecal suspension of SAR-55 HEV. Recombinant antigens used in ELISA were: glutathione-S-transferase (GST); 3-2(M), a fusion of the 3-2 epitope [Yarbough et al., 1991] and (GST); SG3 (B), a fusion of 327 C-terminal amino acids of ORF-2 and GST [Yarbough et al., 1993]; and the 55 kDa ORF-2 product directly expressed in insect cells.

DETAILED DESCRIPTION OF THE INVENTION

Figure 1:
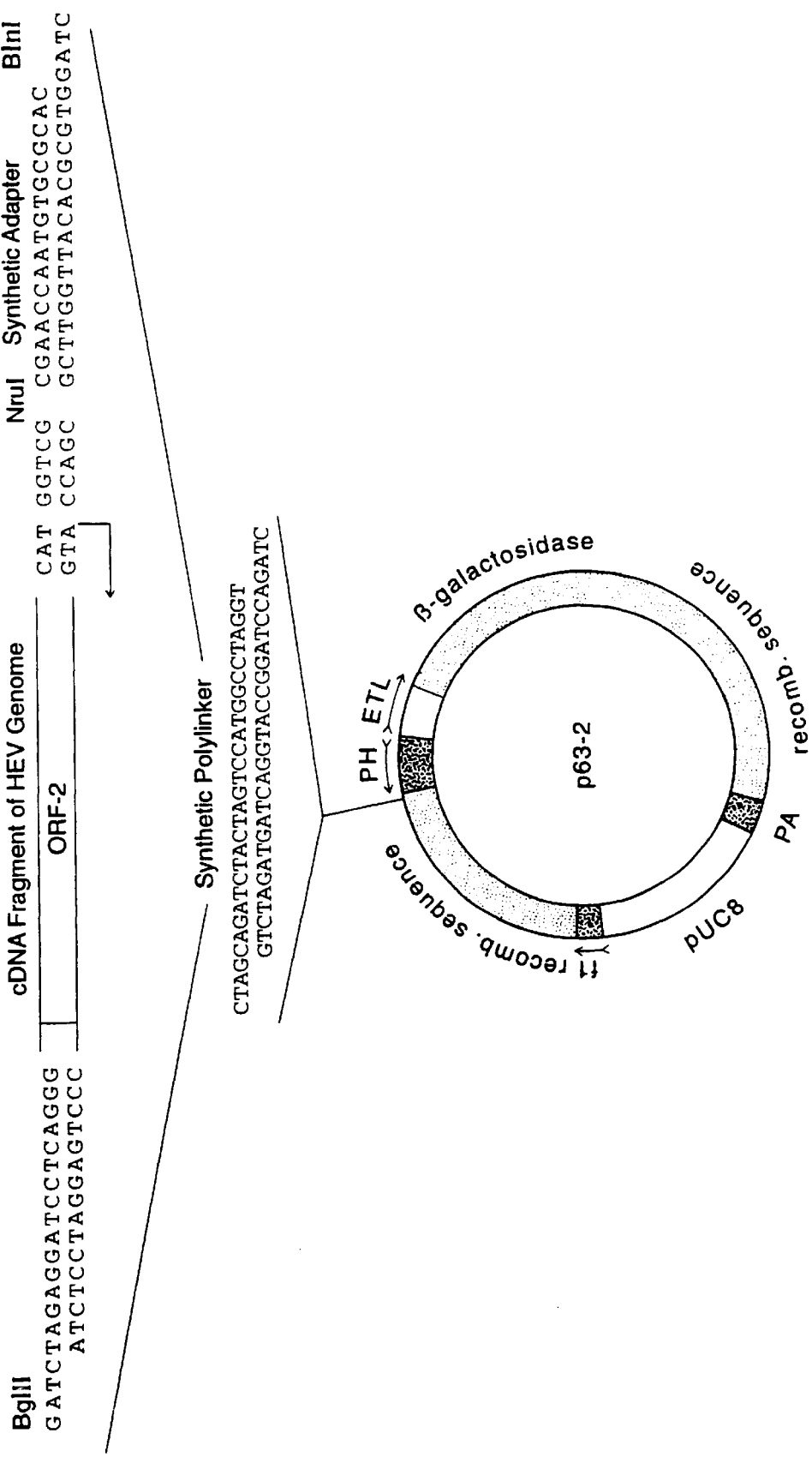
FIG. 1 shows the recombinant vector used to express the complete ORF-2 protein of the genome of HEV strain SAR-55.

The present invention relates to an isolated and substantially purified strain of hepatitis E virus (HEV) from Pakistan, SAR-55. The present invention also relates to the cloning of the viral genes encoding proteins of HEV and the expression of the recombinant proteins using an expression system. More specifically, the present invention relates to the cloning and expression of the open reading frames (ORF) of HEV derived from SAR-55.

The present invention relates to isolated HEV proteins. Preferably, the HEV proteins of the present invention are substantially homologous to, and most preferably biologically equivalent to, the native HEV proteins. By "biologically equivalent" as used throughout the specification and claims, it is meant that the compositions are capable of forming viral-like particles and are immunogenic. The HEV proteins of the present invention may also stimulate the production of protective antibodies upon injection into a mammal that would serve to protect the mammal upon challenge with a wild-type HEV. By "substantially homologous" as used throughout the ensuing specification and claims, is meant a degree of homology in the amino acid sequence to the native HEV proteins. Preferably the degree of homology is in excess of 70%, preferably in excess of 90%, with a particularly preferred group of proteins being in excess of 99% homologous with the native HEV proteins.

Preferred HEV proteins are those proteins that are encoded by the ORF genes. Of particular interest are proteins encoded by the ORF-2 gene of HEV and most particularly proteins encoded by the ORF-2 gene of the SAR-55 strain of HEV. The preferred proteins of the present invention, encoded by the ORF-2 gene, form virus-like particles. The amino acid sequences of the ORF-1, ORF-2 and ORF-3 proteins are shown below as SEQ ID NO.: 1, SEQ ID NO.: 2, and SEQ ID NO.: 3, respectively:

```
Met Glu Ala His Gln Phe Ile Lys Ala Pro Gly Ile Thr Thr Ala    (SEQ. ID NO.: 1)
1               5                   10                  15

Ile Glu Gln Ala Ala Leu Ala Ala Ala Asn Ser Ala Leu Ala Asn
                20              25                  30

Ala Val Val Val Arg Pro Phe Leu Ser His Gln Gln Ile Glu Ile
                35              40                  45

Leu Ile Asn Leu Met Gln Pro Arg Gln Leu Val Phe Arg Pro Glu
                50              55                  60

Val Phe Trp Asn His Pro Ile Gln Arg Val Ile His Asn Glu Leu
                65              70                  75

Glu Leu Tyr Cys Arg Ala Arg Ser Gly Arg Cys Leu Glu Ile Gly
                80              85                  90

Ala His Pro Arg Ser Ile Asn Asp Asn Pro Asn Val Val His Arg
                95              100                 105

Cys Phe Leu Arg Pro Ala Gly Arg Asp Val Gln Arg Trp Tyr Thr
                110             115                 120

Ala Pro Thr Arg Gly Pro Ala Ala Asn Cys Arg Arg Ser Ala Leu
                125             130                 135

Arg Gly Leu Pro Ala Ala Asp Arg Thr Tyr Cys Phe Asp Gly Phe
                140             145                 150

Ser Gly Cys Asn Phe Pro Ala Glu Thr Gly Ile Ala Leu Tyr Ser
                155             160                 165

Leu His Asp Met Ser Pro Ser Asp Val Ala Glu Ala Met Phe Arg
                170             175                 180

His Gly Met Thr Arg Leu Tyr Ala Ala Leu His Leu Pro Pro Glu
                185             190                 195

Val Leu Leu Pro Pro Gly Thr Tyr Arg Thr Ala Ser Tyr Leu Leu
                200             205                 210

Ile His Asp Gly Arg Arg Val Val Val Thr Tyr Glu Gly Asp Thr
                215             220                 225

Ser Ala Gly Tyr Asn His Asp Val Ser Asn Leu Arg Ser Trp Ile
                230             235                 240

Arg Thr Thr Lys Val Thr Gly Asp His Pro Leu Val Ile Glu Arg
                245             250                 255

Val Arg Ala Ile Gly Cys His Phe Val Leu Leu Leu Thr Ala Ala
                260             265                 270

Pro Glu Pro Ser Pro Met Pro Tyr Val Pro Tyr Pro Arg Ser Thr
                275             280                 285

Glu Val Tyr Val Arg Ser Ile Phe Gly Pro Gly Gly Thr Pro Ser
                290             295                 300
```

```
                          -continued
Leu Phe Pro Thr Ser Cys Ser Thr Lys Ser Thr Phe His Ala Val
                305                 310                 315

Pro Ala His Ile Trp Asp Arg Leu Met Leu Phe Gly Ala Thr Leu
                320                 325                 330

Asp Asp Gln Ala Phe Cys Cys Ser Arg Leu Met Thr Tyr Leu Arg
                335                 340                 345

Gly Ile Ser Tyr Lys Val Thr Val Gly Thr Leu Val Ala Asn Glu
                350                 355                 360

Gly Trp Asn Ala Ser Glu Asp Ala Leu Thr Ala Val Ile Thr Ala
                365                 370                 375

Ala Tyr Leu Thr Ile Cys His Gln Arg Tyr Leu Arg Thr Gln Ala
                380                 385                 390

Ile Ser Lys Gly Met Arg Arg Leu Glu Arg Glu His Ala Gln Lys
                395                 400                 405

Phe Ile Thr Arg Leu Tyr Ser Trp Leu Phe Glu Lys Ser Gly Arg
                410                 415                 420

Asp Tyr Ile Pro Gly Arg Gln Leu Glu Phe Tyr Ala Gln Cys Arg
                425                 430                 435

Arg Trp Leu Ser Ala Gly Phe His Leu Asp Pro Arg Val Leu Val
                440                 445                 450

Phe Asp Glu Ser Ala Pro Cys His Cys Arg Thr Ala Ile Arg Lys
                455                 460                 465

Ala Val Ser Lys Phe Cys Cys Phe Met Lys Trp Leu Gly Gln Glu
                470                 475                 480

Cys Thr Cys Phe Leu Gln Pro Ala Glu Gly Val Val Gly Asp Gln
                485                 490                 495

Gly His Asp Asn Glu Ala Tyr Glu Gly Ser Asp Val Asp Pro Ala
                500                 505                 510

Glu Ser Ala Ile Ser Asp Ile Ser Gly Ser Tyr Val Pro Gly
                515                 520                 525

Thr Ala Leu Gln Pro Leu Tyr Gln Ala Leu Asp Leu Pro Ala Glu
                530                 535                 540

Ile Val Ala Arg Ala Gly Arg Leu Thr Ala Thr Val Lys Val Ser
                545                 550                 555

Gln Val Asp Gly Arg Ile Asp Cys Glu Thr Leu Leu Gly Asn Lys
                560                 565                 570

Thr Phe Arg Thr Ser Phe Val Asp Gly Ala Val Leu Glu Thr Asn
                575                 580                 585

Gly Pro Glu Arg His Asn Leu Ser Phe Asp Ala Ser Gln Ser Thr
                590                 595                 600

Met Ala Ala Gly Pro Phe Ser Leu Thr Tyr Ala Ala Ser Ala Ala
                605                 610                 615

Gly Leu Glu Val Arg Tyr Val Ala Ala Gly Leu Asp His Arg Ala
                620                 625                 630

Val Phe Ala Pro Gly Val Ser Pro Arg Ser Ala Pro Gly Glu Val
                635                 640                 645

Thr Ala Phe Cys Ser Ala Leu Tyr Arg Phe Asn Arg Glu Ala Gln
                650                 655                 660

Arg Leu Ser Leu Thr Gly Asn Phe Trp Phe His Pro Glu Gly Leu
                665                 670                 675

Leu Gly Pro Phe Ala Pro Phe Ser Pro Gly His Val Trp Glu Ser
                680                 685                 690

Ala Asn Pro Phe Cys Gly Glu Ser Thr Leu Tyr Thr Arg Thr Trp
                695                 700                 705
```

-continued

```
Ser Glu Val Asp Ala Val Pro Ser Pro Ala Gln Pro Asp Leu Gly
            710                 715                 720
Phe Thr Ser Glu Pro Ser Ile Pro Ser Arg Ala Ala Thr Pro Thr
            725                 730                 735
Pro Ala Ala Pro Leu Pro Pro Ala Pro Asp Pro Ser Pro Thr
            740                 745                 750
Leu Ser Ala Pro Ala Arg Gly Glu Pro Ala Pro Gly Ala Thr Ala
            755                 760                 765
Arg Ala Pro Ala Ile Thr His Gln Thr Ala Arg His Arg Arg Leu
            770                 775                 780
Leu Phe Thr Tyr Pro Asp Gly Ser Lys Val Phe Ala Gly Ser Leu
            785                 790                 795
Phe Glu Ser Thr Cys Thr Trp Leu Val Asn Ala Ser Asn Val Asp
            800                 805                 810
His Arg Pro Gly Gly Gly Leu Cys His Ala Phe Tyr Gln Arg Tyr
            815                 820                 825
Pro Ala Ser Phe Asp Ala Ala Ser Phe Val Met Arg Asp Gly Ala
            830                 835                 840
Ala Ala Tyr Thr Leu Thr Pro Arg Pro Ile Ile His Ala Val Ala
            845                 850                 855
Pro Asp Tyr Arg Leu Glu His Asn Pro Lys Arg Leu Glu Ala Ala
            860                 865                 870
Tyr Arg Glu Thr Cys Ser Arg Leu Gly Thr Ala Ala Tyr Pro Leu
            875                 880                 885
Leu Gly Thr Gly Ile Tyr Gln Val Pro Ile Gly Pro Ser Phe Asp
            890                 895                 900
Ala Trp Glu Arg Asn His Arg Pro Gly Asp Glu Leu Tyr Leu Pro
            905                 910                 915
Glu Leu Ala Ala Arg Trp Phe Glu Ala Asn Arg Pro Thr Cys Pro
            920                 925                 930
Thr Leu Thr Ile Thr Glu Asp Val Ala Arg Thr Ala Asn Leu Ala
            935                 940                 945
Ile Glu Leu Asp Ser Ala Thr Asp Val Gly Arg Ala Cys Ala Gly
            950                 955                 960
Cys Arg Val Thr Pro Gly Val Val Gln Tyr Gln Phe Thr Ala Gly
            965                 970                 975
Val Pro Gly Ser Gly Lys Ser Arg Ser Ile Thr Gln Ala Asp Val
            980                 985                 990
Asp Val Val Val Pro Thr Arg Glu Leu Arg Asn Ala Trp Arg
            995                 1000                1005
Arg Arg Gly Phe Ala Ala Phe Thr Pro His Thr Ala Ala Arg Val
            1010                1015                1020
Thr Gln Gly Arg Arg Val Val Ile Asp Glu Ala Pro Ser Leu Pro
            1025                1030                1035
Pro His Leu Leu Leu Leu His Met Gln Arg Ala Ala Thr Val His
            1040                1045                1050
Leu Leu Gly Asp Pro Asn Gln Ile Pro Ala Ile Asp Phe Glu His
            1055                1060                1065
Ala Gly Leu Val Pro Ala Ile Arg Pro Asp Leu Ala Pro Thr Ser
            1070                1075                1080
Trp Trp His Val Thr His Arg Cys Pro Ala Asp Val Cys Glu Leu
            1085                1090                1095
Ile Arg Gly Ala Tyr Pro Met Ile Gln Thr Thr Ser Arg Val Leu
```

-continued

Arg Ser Leu Phe Trp Gly Glu Pro Ala Val Gly Gln Lys Leu Val
1100                1105                1110            1125
                1115                1120

Phe Thr Gln Ala Ala Lys Ala Ala Asn Pro Gly Ser Val Thr Val
                1130                1135                1140

His Glu Ala Gln Gly Ala Thr Tyr Thr Glu Thr Thr Ile Ile Ala
                1145                1150                1155

Thr Ala Asp Ala Arg Gly Leu Ile Gln Ser Ser Arg Ala His Ala
                1160                1165                1170

Ile Val Ala Leu Thr Arg His Thr Glu Lys Cys Val Ile Ile Asp
                1175                1180                1185

Ala Pro Gly Leu Leu Arg Glu Val Gly Ile Ser Asp Ala Ile Val
                1190                1195                1200

Asn Asn Phe Phe Leu Ala Gly Gly Glu Ile Gly His Gln Arg Pro
                1205                1210                1215

Ser Val Ile Pro Arg Gly Asn Pro Asp Ala Asn Val Asp Thr Leu
                1220                1225                1230

Ala Ala Phe Pro Pro Ser Cys Glu Ile Ser Ala Phe His Glu Leu
                1235                1240                1245

Ala Glu Glu Leu Gly His Arg Pro Ala Pro Val Ala Ala Val Leu
                1250                1255                1260

Pro Pro Cys Pro Glu Leu Glu Gln Gly Leu Leu Tyr Leu Pro Gln
                1265                1270                1275

Glu Leu Thr Thr Cys Asp Ser Val Val Thr Phe Glu Leu Thr Asp
                1280                1285                1290

Ile Val His Cys Arg Met Ala Ala Pro Ser Gln Arg Lys Ala Val
                1295                1300                1305

Leu Ser Thr Leu Val Gly Arg Tyr Gly Arg Arg Thr Lys Leu Tyr
                1310                1315                1320

Asn Ala Ser His Ser Asp Val Arg Asp Ser Leu Ala Arg Phe Ile
                1325                1330                1335

Pro Ala Ile Gly Pro Val Gln Val Thr Thr Cys Glu Leu Tyr Glu
                1340                1345                1350

Leu Glu Glu Ala Met Val Glu Lys Gly Gln Asp Gly Ser Ala Val
                1355                1360                1365

Leu Glu Leu Asp Leu Cys Ser Arg Asp Val Ser Arg Ile Thr Phe
                1370                1375                1380

Phe Gln Lys Asp Cys Asn Lys Phe Thr Thr Gly Glu Thr Ile Ala
                1385                1390                1395

His Gly Lys Val Gly Gln Gly Ile Ser Ala Trp Ser Lys Thr Phe
                1400                1405                1410

Cys Ala Leu Phe Gly Pro Trp Phe Arg Ala Ile Glu Lys Ala Ile
                1415                1420                1425

Leu Ala Leu Leu Pro Gln Gly Val Phe Tyr Gly Asp Ala Phe Asp
                1430                1435                1440

Asp Thr Val Phe Ser Ala Ala Val Ala Ala Lys Ala Ser Met
                1445                1450                1455

Val Phe Glu Asn Asp Phe Ser Glu Phe Asp Ser Thr Gln Asn Asn
                1460                1465                1470

Phe Ser Leu Gly Leu Glu Cys Ala Ile Met Glu Glu Cys Gly Met
                1475                1480                1485

Pro Gln Trp Leu Ile Arg Leu Tyr His Leu Ile Arg Ser Ala Trp
                1490                1495                1500

```
Ile Leu Gln Ala Pro Lys Glu Ser Leu Arg Gly Phe Trp Lys Lys
               1505                1510                1515

His Ser Gly Glu Pro Gly Thr Leu Leu Trp Asn Thr Val Trp Asn
           1520                1525                1530

Met Ala Val Ile Thr His Cys Tyr Asp Phe Arg Asp Leu Gln Val
           1535                1540                1545

Ala Ala Phe Lys Gly Asp Asp Ser Ile Val Leu Cys Ser Glu Tyr
           1550                1555                1560

Arg Gln Ser Pro Gly Ala Ala Val Leu Ile Ala Gly Cys Gly Leu
           1565                1570                1575

Lys Leu Lys Val Asp Phe Arg Pro Ile Gly Leu Tyr Ala Gly Val
           1580                1585                1590

Val Val Ala Pro Gly Leu Gly Ala Leu Pro Asp Val Val Arg Phe
           1595                1600                1605

Ala Gly Arg Leu Thr Glu Lys Asn Trp Gly Pro Gly Pro Glu Arg
           1610                1615                1620

Ala Glu Gln Leu Arg Leu Ala Val Ser Asp Phe Leu Arg Lys Leu
           1625                1630                1635

Thr Asn Val Ala Gln Met Cys Val Asp Val Val Ser Arg Val Tyr
           1640                1645                1650

Gly Val Ser Pro Gly Leu Val His Asn Leu Ile Glu Met Leu Gln
           1655                1660                1665

Ala Val Ala Asp Gly Lys Ala His Phe Thr Glu Ser Val Lys Pro
           1670                1675                1680

Val Leu Asp Leu Thr Asn Ser Ile Leu Cys Arg Val Glu
           1685                1690

Met Arg Pro Arg Pro Ile Leu Leu Leu Leu Met Phe Leu Pro   (SEQ. ID NO.: 2)
1               5                  10                15

Met Leu Pro Ala Pro Pro Gly Gln Pro Ser Gly Arg Arg Arg
               20                  25                 30

Gly Arg Arg Ser Gly Gly Ser Gly Gly Gly Phe Trp Gly Asp Arg
           35                  40                  45

Val Asp Ser Gln Pro Phe Ala Ile Pro Tyr Ile His Pro Thr Asn
           50                  55                  60

Pro Phe Ala Pro Asp Val Thr Ala Ala Gly Ala Gly Pro Arg
               65                  70                 75

Val Arg Gln Pro Ala Arg Pro Leu Gly Ser Ala Trp Arg Asp Gln
           80                  85                  90

Ala Gln Arg Pro Ala Ala Ala Ser Arg Arg Pro Thr Thr Ala
               95                 100                105

Gly Ala Ala Pro Leu Thr Ala Val Ala Pro Ala His Asp Thr Pro
           110                 115                 120

Pro Val Pro Asp Val Asp Ser Arg Gly Ala Ile Leu Arg Arg Gln
           125                 130                 135

Tyr Asn Leu Ser Thr Ser Pro Leu Thr Ser Ser Val Ala Thr Gly
           140                 145                 150

Thr Asn Leu Val Leu Tyr Ala Ala Pro Leu Ser Pro Leu Leu Pro
           155                 160                 165

Leu Gln Asp Gly Thr Asn Thr His Ile Met Ala Thr Glu Ala Ser
           170                 175                 180

Asn Tyr Ala Gln Tyr Arg Val Ala Arg Ala Thr Ile Arg Tyr Arg
           185                 190                 195

Pro Leu Val Pro Asn Ala Val Gly Gly Tyr Ala Ile Ser Ile Ser
           200                 205                 210
```

-continued

```
Phe Tyr Pro Gln Thr Thr Thr Pro Thr Ser Val Asp Met Asn
                215                 220                 225

Ser Ile Thr Ser Thr Asp Val Arg Ile Leu Val Gln Pro Gly Ile
                230                 235                 240

Ala Ser Glu Leu Val Ile Pro Ser Glu Arg Leu His Tyr Arg Asn
                245                 250                 255

Gln Gly Trp Arg Ser Val Glu Thr Ser Gly Val Ala Glu Glu Glu
                260                 265                 270

Ala Thr Ser Gly Leu Val Met Leu Cys Ile His Gly Ser Pro Val
                275                 280                 285

Asn Ser Tyr Thr Asn Thr Pro Tyr Thr Gly Ala Leu Gly Leu Leu
                290                 295                 300

Asp Phe Ala Leu Glu Leu Glu Phe Arg Asn Leu Thr Pro Gly Asn
                305                 310                 315

Thr Asn Thr Arg Val Ser Arg Tyr Ser Thr Ala Arg His Arg
                320                 325                 330

Leu Arg Arg Gly Ala Asp Gly Thr Ala Glu Leu Thr Thr Thr Ala
                335                 340                 345

Ala Thr Arg Phe Met Lys Asp Leu Tyr Phe Thr Ser Thr Asn Gly
                350                 355                 360

Val Gly Glu Ile Gly Arg Gly Ile Ala Leu Thr Leu Phe Asn Leu
                365                 370                 375

Ala Asp Thr Leu Leu Gly Gly Leu Pro Thr Glu Leu Ile Ser Ser
                380                 385                 390

Ala Gly Gly Gln Leu Phe Tyr Ser Arg Pro Val Val Ser Ala Asn
                395                 400                 405

Gly Glu Pro Thr Val Lys Leu Tyr Thr Ser Val Glu Asn Ala Gln
                410                 415                 420

Gln Asp Lys Gly Ile Ala Ile Pro His Asp Ile Asp Leu Gly Glu
                425                 430                 435

Ser Arg Val Val Ile Gln Asp Tyr Asp Asn Gln His Glu Gln Asp
                440                 445                 450

Arg Pro Thr Pro Ser Pro Ala Pro Ser Arg Pro Phe Ser Val Leu
                455                 460                 465

Arg Ala Asn Asp Val Leu Trp Leu Ser Leu Thr Ala Ala Glu Tyr
                470                 475                 480

Asp Gln Ser Thr Tyr Gly Ser Ser Thr Gly Pro Val Tyr Val Ser
                485                 490                 495

Asp Ser Val Thr Leu Val Asn Val Ala Thr Gly Ala Gln Ala Val
                500                 505                 510

Ala Arg Ser Leu Asp Trp Thr Lys Val Thr Leu Asp Gly Arg Pro
                515                 520                 525

Leu Ser Thr Ile Gln Gln Tyr Ser Lys Thr Phe Phe Val Leu Pro
                530                 535                 540

Leu Arg Gly Lys Leu Ser Phe Trp Glu Ala Gly Thr Thr Lys Ala
                545                 550                 555

Gly Tyr Pro Tyr Asn Tyr Asn Thr Thr Ala Ser Asp Gln Leu Leu
                560                 565                 570

Val Glu Asn Ala Ala Gly His Arg Val Ala Ile Ser Thr Tyr Thr
                575                 580                 585

Thr Ser Leu Gly Ala Gly Pro Val Ser Ile Ser Ala Val Ala Val
                590                 595                 600

Leu Ala Pro His Ser Val Leu Ala Leu Leu Glu Asp Thr Met Asp
```

-continued

```
              605              610              615
Tyr Pro Ala Arg Ala His Thr Phe Asp Asp Phe Cys Pro Glu Cys
                620              625              630
Arg Pro Leu Gly Leu Gln Gly Cys Ala Phe Gln Ser Thr Val Ala
                635              640              645
Glu Leu Gln Arg Leu Lys Met Lys Val Gly Lys Thr Arg Glu Leu
                650              655              660
Met Asn Asn Met Ser Phe Ala Ala Pro Met Gly Ser Arg Pro Cys  (SEQ. ID NO.: 3)
 1               5              10              15
Ala Leu Gly Leu Phe Cys Cys Cys Ser Ser Cys Phe Cys Leu Cys
                20              25              30
Cys Pro Arg His Arg Pro Val Ser Arg Leu Ala Ala Val Val Gly
                35              40              45
Gly Ala Ala Ala Val Pro Ala Val Val Ser Gly Val Thr Gly Leu
                50              55              60
Ile Leu Ser Pro Ser Gln Ser Pro Ile Phe Ile Gln Pro Thr Pro
                65              70              75
Ser Pro Pro Met Ser Pro Leu Arg Pro Gly Leu Asp Leu Val Phe
                80              85              90
Ala Asn Pro Pro Asp His Ser Ala Pro Leu Gly Val Thr Arg Pro
                95             100             105
Ser Ala Pro Pro Leu Pro His Val Val Asp Leu Pro Gln Leu Gly
               110             115             120
Pro Arg Arg
```

The three-letter abbreviations follow the conventional amino acid shorthand for the twenty naturally occuring amino acids.

The preferred recombinant HEV proteins consist of at least one ORF protein. Other recombinant proteins made up of more than one of the same or different ORF proteins may be made to alter the biological properties of the protein. It is contemplated that additions, substitutions or deletions of discrete amino acids or of discrete sequences of amino acids may enhance the biological activity of the HEV proteins.

The present invention is also a nucleic acid sequence which is capable of directing the production of the above-discussed HEV protein or proteins substantially homologous to the HEV proteins. This nucleic acid sequence, designated SAR-55, is set forth below as SEQ ID NO.: 4 and was deposited with the American Type Culture Collection (ATCC) on Sep. 17, 1992 (ATCC accession number 75302).

```
AGGCAGACCA CATATGTGGT CGATGCCATG GAGGCCCATC     40

AGTTTATCAA GGCTCCTGGC ATCACTACTG CTATTGAGCA     80

GGCTGCTCTA GCAGCGGCCA ACTCTGCCCT TGCGAATGCT    120

GTGGTAGTTA GGCCTTTTCT CTCTCACCAG CAGATTGAGA    160

TCCTTATTAA CCTAATGCAA CCTCGCCAGC TTGTTTTCCG    200

CCCCGAGGTT TTCTGGAACC ATCCCATCCA GCGTGTTATC    240

CATAATGAGC TGGAGCTTTA CTGTCGCGCC CGCTCCGGCC    280

GCTGCCTCGA AATTGGTGCC CACCCCCGCT CAATAAATGA    320

CAATCCTAAT GTGGTCCACC GTTGCTTCCT CCGTCCTGCC    360
```

-continued

```
GGGCGTGATG TTCAGCGTTG GTATACTGCC CCTACCCGCG    400

GGCCGGCTGC TAATTGCCGG CGTTCCGCGC TGCGCGGGCT    440

CCCCGCTGCT GACCGCACTT ACTGCTTCGA CGGGTTTTCT    480

GGCTGTAACT TTCCCGCCGA GACGGGCATC GCCCTCTATT    520

CTCTCCATGA TATGTCACCA TCTGATGTCG CCGAGGCTAT    560

GTTCCGCCAT GGTATGACGC GGCTTTACGC TGCCCTCCAC    600

CTCCCGCCTG AGGTCCTGTT GCCCCCTGGC ACATACCGCA    640

CCGCGTCGTA CTTGCTGATC CATGACGGCA GGCGCGTTGT    680

GGTGACGTAT GAGGGTGACA CTAGTGCTGG TTATAACCAC    720

GATGTTTCCA ACCTGCGCTC CTGGATTAGA ACCACTAAGG    760

TTACCGGAGA CCACCCTCTC GTCATCGAGC GGGTTAGGGC    800

CATTGGCTGC CACTTTGTCC TTTTACTCAC GGCTGCTCCG    840

GAGCCATCAC CTATGCCCTA TGTCCCTTAC CCCCGGTCTA    880

CCGAGGTCTA TGTCCGATCG ATCTTCGGCC CGGGTGGCAC    920

CCCCTCCCTA TTTCCAACCT CATGCTCCAC CAAGTCGACC    960

TTCCATGCTG TCCCTGCCCA TATCTGGGAC CGTCTCATGT   1000

TGTTCGGGGC CACCCTAGAT GACCAAGCCT TTTGCTGCTC   1040

CCGCCTAATG ACTTACCTCC GCGGCATTAG CTACAAGGTT   1080

ACTGTGGGCA CCCTTGTTGC CAATGAAGGC TGGAACGCCT   1120
```

-continued

| | |
|---|---|
| CTGAGGACGC TCTTACAGCT CTCATCACTG CCGCCTACCT | 1160 |
| TACCATCTGC CACCAGCGGT ACCTCCGCAC TCAGGCTATA | 1200 |
| TCTAAGGGGA TGCGTCGCCT GGAGCGGGAG CATGCTCAGA | 1240 |
| AGTTTATAAC ACGCCTCTAC AGTTGGTCTC TTGAGAAGTC | 1280 |
| CGGCCGTGAT TATATCCCCG GCCGTCAGTT GGAGTTCTAC | 1320 |
| GCTCAGTGTA GGCGCTGGCT CTCGGCCGGC TTTCATCTTG | 1360 |
| ACCCACGGGT GTTGGTTTTT GATGAGTCGG CCCCCTGCCA | 1400 |
| CTGTAGGACT GCGATTCGTA AGGCGGTCTC AAAGTTTTGC | 1440 |
| TGCTTTATGA AGTGGCTGGG CCAGGAGTGC ACCTGTTTTC | 1480 |
| TACAACCTGC AGAAGGCGTC GTTGGCGACC AGGGCCATGA | 1520 |
| CAACGAGGCC TATGAGGGGT CTGATGTTGA CCCTGCTGAA | 1560 |
| TCCGCTATTA GTGACATATC TGGGTCCTAC GTAGTCCCTG | 1600 |
| GCACTGCCCT CCAACCGCTT TACCAAGCCC TTGACCTCCC | 1640 |
| CGCTGAGATT GTGGCTCGTG CAGGCCGGCT GACCGCCACA | 1680 |
| GTAAAGGTCT CCCAGGTCGA CGGGCGGATC GATTGTGAGA | 1720 |
| CCCTTCTCGG TAATAAAACC TTCCGCACGT CGTTTGTTGA | 1760 |
| CGGGGCGGTT TTAGAGACTA ATGGCCCAGA GCGCCACAAT | 1800 |
| CTCTCTTTTG ATGCCAGTCA GAGCACTATG GCCGCCGGCC | 1840 |
| CTTTCAGTCT CACCTATGCC GCCTCTGCTG CTGGGCTGGA | 1880 |
| GGTGCGCTAT GTCGCCGCCG GGCTTGACCA CCGGGCGGTT | 1920 |
| TTTGCCCCCG GCGTTTCACC CCGGTCAGCC CCTGGCGAGG | 1960 |
| TCACCGCCTT CTGTTCTGCC CTATACAGGT TTAATCGCGA | 2000 |
| GGCCCAGCGC CTTTCGCTGA CCGGTAATTT TTGGTTCCAT | 2040 |
| CCTGAGGGGC TCCTTGGCCC CTTTGCCCCG TTTTCCCCCG | 2080 |
| GGCATGTTTG GGAGTCGGCT AATCCATTCT GTGGCGAGAG | 2120 |
| CACACTTTAC ACCCGCACTT GGTCGGAGGT TGATGCTGTT | 2160 |
| CCTAGTCCAG CCCAGCCCGA CTTAGGTTTT ACATCTGAGC | 2200 |
| CTTCTATACC TAGTAGGGCC GCCACACCTA CCCCGGCGGC | 2240 |
| CCCTCTACCC CCCCCTGCAC CGGATCCTTC CCCTACTCTC | 2280 |
| TCTGCTCCGG CGCGTGGTGA GCCGGCTCCT GGCGCTACCG | 2320 |
| CCAGGGCCCC AGCCATAACC CACCAGACGG CCCGGCATCG | 2360 |
| CCGCCTGCTC TTTACCTACC CGGATGGCTC TAAGGTGTTC | 2400 |
| GCCGGCTCGC TGTTTGAGTC GACATGTACC TGGCTCGTTA | 2440 |
| ACGCGTCTAA TGTTGACCAC CGCCCTGGCG GTGGGCTCTG | 2480 |
| TCATGCATTT TACCAGAGGT ACCCCGCCTC CTTTGATGCT | 2520 |
| GCCTCTTTTG TGATGCGCGA CGGCGCGGCC GCCTACACAT | 2560 |
| TAACCCCCCG GCCAATAATT CATGCCGTCG CTCCTGATTA | 2600 |
| TAGGTTGGAA CATAACCCAA AGAGGCTTGA GGCTGCCTAC | 2640 |
| CGGGAGACTT GCTCCCGCCT CGGTACCGCT GCATACCCAC | 2680 |
| TCCTCGGGAC CGGCATATAC CAGGTGCCGA TCGGTCCCAG | 2720 |
| TTTTGACGCC TGGGAGCGGA ATCACCGCCC CGGGGACGAG | 2760 |
| TTGTACCTTC CTGAGCTTGC TGCCAGATGG TTCGAGGCCA | 2800 |
| ATAGGCCGAC CTGCCCAACT CTCACTATAA CTGAGGATGT | 2840 |
| TGCGCGGACA GCAAATCTGG CTATCGAACT TGACTCAGCC | 2880 |
| ACAGACGTCG GCCGGGCCTG TGCCGGCTGT CGAGTCACCC | 2920 |
| CCGGCGTTGT GCAGTACCAG TTTACCGCAG GTGTGCCTGG | 2960 |
| ATCCGGCAAG TCCCGCTCTA TTACCCAAGC CGACGTGGAC | 3000 |
| GTTGTCGTGG TCCCGACCCG GGAGTTGCGT AATGCCTGGC | 3040 |
| GCCGCCGCGG CTTCGCTGCT TTCACCCCGC ACACTGCGGC | 3080 |
| TAGAGTCACC CAGGGGCGCC GGGTTGTCAT TGATGAGGCC | 3120 |
| CCGTCCCTTC CCCCTCATTT GCTGCTGCTC CACATGCAGC | 3160 |
| GGGCCGCCAC CGTCCACCTT CTTGGCGACC CGAATCAGAT | 3200 |
| CCCAGCCATC GATTTTGAGC ACGCCGGGCT CGTTCCCGCC | 3240 |
| ATCAGGCCCG ATTTGGCCCC CACCTCCTGG TGGCATGTTA | 3280 |
| CCCATCGCTG CCCTGCGGAT GTATGTGAGC TAATCCGCGG | 3320 |
| CGCATACCCT ATGATTCAGA CCACTAGTCG GGTCCTCCGG | 3360 |
| TCGTTGTTCT GGGGTGAGCC CGCCGTTGGG CAGAAGCTAG | 3400 |
| TGTTCACCCA GGCGGCTAAG GCCGCCAACC CCGGTTCAGT | 3440 |
| GACGGTCCAT GAGGCACAGG GCGCTACCTA CACAGAGACT | 3480 |
| ACCATCATTG CCACGGCAGA TGCTCGAGGC CTCATTCAGT | 3520 |
| CGTCCCGAGC TCATGCCATT GTTGCCTTGA CGCGCCACAC | 3560 |
| TGAGAAGTGC GTCATCATTG ACGCACCAGG CCTGCTTCGC | 3600 |
| GAGGTGGGCA TCTCCGATGC AATCGTTAAT AACTTTTTCC | 3640 |
| TTGCTGGTGG CGAAATTGGC CACCAGCGCC CATCTGTTAT | 3680 |
| CCCTCGCGGC AATCCTGACG CCAATGTTGA CACCTTGGCT | 3720 |
| GCCTTCCCGC CGTCTTGCCA GATTAGCGCC TTCCATCAGT | 3760 |
| TGGCTGAGGA GCTTGGCCAC AGACCTGCCC CTGTCGCGGC | 3800 |
| TGTTCTACCG CCCTGCCCTG AGCTTGAACA GGGCCTTCTC | 3840 |
| TACCTGCCCC AAGAACTCAC CACCTGTGAT AGTGTCGTAA | 3880 |
| CATTTCAATT AACAGATATT GTGCATTGTC GTATGGCCGC | 3920 |
| CCCGAGCCAG CGCAAGGCCG TGCTGTCCAC GCTCGTGGGC | 3960 |
| CGTTATGGCC GCCGCACAAA GCTCTACAAT GCCTCCCACT | 4000 |
| CTGATGTTCG CGACTCTCTC GCCCGTTTTA TCCCGGCCAT | 4040 |
| TGGCCCCGTA CAGGTTACAA CCTGTGAATT GTACGAGCTA | 4080 |
| GTGGAGGCCA TGGTCGAGAA GGGCCAGGAC GGCTCCGCCG | 4120 |
| TCCTTGAGCT CGACCTTTGT AGCCGCGACG TGTCCAGGAT | 4160 |
| CACCTTCTTC CAGAAAGATT GTAATAAATT CACCACGGGG | 4200 |
| GAGACCATCG CCCATGGTAA AGTGGGCCAG GGCATTTCGG | 4240 |
| CCTGGAGTAA GACCTTCTGT GCCCTTTTCG GCCCCTGGTT | 4280 |
| CCGTGCTATT GAGAAGGCTA TCCTGGCCCT GCTCCCTCAG | 4320 |

```
GGTGTGTTTT ATGGGGATGC CTTTGATGAC ACCGTCTTCT      4360
CGGCGGCTGT GGCCGCAGCA AAGGCATCCA GAATGACTTT      4400
TCTGAGTTTG ATTCCACCCA GAATAATTTT TCCTTGGGCC      4440
TAGAGTGTGC TATTATGGAG GAGTGTGGGA TGCCGCAGTG      4480
GCTCATCCGC TTGTACCACC TTATAAGGTC TGCGTGGATT      4520
CTGCAGGCCC CGAAGGAGTC CCTGCGAGGG TTTTGGAAGA      4560
AACACTCCGG TGAGCCCGGC ACCCTTCTGT GGAATACTGT      4600
CTGGAACATG GCCGTTATCA CCCACTGTTA TGATTTCCGC      4640
GATCTGCAGG TGGCTGCCTT TAAAGGTGAT GATTCGATAG      4680
TGCTTTGCAG TGAGTACCGT CAGAGCCCAG GGGCTGCTGT      4720
CCTGATTGCT GGCTGTGGCC TAAAGTTGAA GGTGGATTTC      4760
CGTCCGATTG GTCTGTATGC AGGTGTTGTG GTGGCCCCCG      4800
GCCTTGGCGC GCTTCCTGAT GTCGTGCGCT TCGCCGGTCG      4840
GCTTACTGAG AAGAATTGGG GCCCTGGCCC CGAGCGGGCG      4880
GAGCAGCTCC GCCTCGCTGT GAGTGATTTT CTCCGCAAGC      4920
TACCGAATGT AGCTCAGATG TGTGTGGATG TTGTCTCTCG      4960
TGTTTATGGG GTTTCCCCTG GCTCGTTCA TAACCTGATT       5000
GGCATGCTAC AGGCTGTTGC TGATGGCAAG GCTCATTTCA      5040
CTGAGTCAGT GAAGCCAGTG CTTGACCTGA CAAATTCAAT      5080
TCTGTGTCGG GTGGAATGAA TAACATGTCT TTTGCTGCGC      5120
CCATGGGTTC GCGACCATGC GCCCTCGGCC TATTTTGCTG      5160
TTGCTCCTCA TGTTTCTGCC TATGCTGCCC GCGCCACCGC      5200
CCGGTCAGCC GTCTGGCCGC CGTCGTGGGC GGCGCAGCGG      5240
CGGTTCCGGC GGTGGTTTCT GGGGTGACCG GGTTGATTCT      5280
CAGCCCTTCG CAATCCCCTA TATTCATCCA ACCAACCCCT      5320
TCGCCCCCGA TGTCACCGCT GCGGCCGGGG CTGGACCTCG      5360
TGTTCGCCAA CCCGCCCGAC CACTCGGCTC CGCTTGGCGT      5400
GACCAGGCCC AGCGCCCCGC CGCTGCCTCA CGTCGTAGAC      5440
CTACCACAGC TGGGGCCGCG CCGCTAACCG CGGTCGCTCC      5480
GGCCCATGAC ACCCCGCCAG TGCCTGATGT TGACTCCCGC      5520
GGCGCCATCC TGCGCCGGCA GTATAACCTA TCAACATCTC      5560
CCCTCACCTC TTCCGTGGCC ACCGGCACAA ATTTGGTTCT      5600
TTACGCCGCT CCTCTTAGCC CGCTTCTACC CCTCCAGGAC      5640
GGCACCAATA CTCATATAAT GGCTACAGAA GCTTCTAATT      5680
ATGCCCAGTA CCGGGTTGCT CGTGCCACAA TTCGCTACCG      5720
CCCGCTGGTC CCCAACGCTG TTGGTGGCTA CGCTATCTCC      5760
ATTTCGTTCT GGCCACAGAC CACCACCACC CCGACGTCCG      5800
TTGACATGAA TTCAATAACC TCGACGGATG TCCGTATTTT      5840
AGTCCAGCCC GGCATAGCCT CCGAGCTTGT TATTCCAAGT      5880
GAGCGCCTAC ACTATCGCAA GGCCGGTTGG CGCTCTGTTG      5920
AGACCTCCGG GGTGGCGGAG GAGGAGGCCA CCTCTGGTCT      5960
TGTCATGCTC TGCATACATG GCTCACCTGT AAATTCTTAT      6000
ACTAATACAC CCTATACCGG TGCCCTCGGG CTGTTGGACT      6040
TTGCCCTCGA ACTTGAGTTC CGCAACCTCA CCCCCGGTAA      6080
TACCAATACG CGGGTCTCGC GTTACTCCAG CACTGCCCGT      6120
CACCGCCTTC GTCGCGGTGC AGATGGGACT GCCGAGCTCA      6160
CCACCACGGC TGCTACTCGC TTCATGAAGG ACCTCTATTT      6200
TACTAGTACT AATGGTGTTG GTGAGATCGG CCGCGGGATA      6240
GCGCTTACCC TGTTTAACCT TGCTGACACC CTGCTTGGCG      6280
GTCTACCGAC AGAATTGATT TCGTCGGCTG GTGGCCAGCT      6320
GTTCTACTCT CGCCCCGTCG TCTCAGCCAA TGGCGAGCCG      6360
ACTGTTAAGC TGTATACATC TGTGGAGAAT GCTCAGCAGG      6400
ATAAGGGTAT TGCAATCCCG CATGACATCG ACCTCGGGGA      6440
ATCCCGTGTA GTTATTCAGG ATTATGACAA CCAACATGAG      6480
CAGGACCGAC CGACACCTTC CCCAGCCCCA TCGCGTCCTT      6520
TTTCTGTCCT CCGAGCTAAC GATGTGCTTT GGCTTTCTCT      6560
CACCGCTGCC GAGTATGACC AGTCCACTTA CGGCTCTTCG      6600
ACCGGCCCAG TCTATGTCTC TGACTCTGTG ACCTTGGTTA      6640
ATGTTGCGAC CGGCGCGCAG GCCGTTGCCC GGTCACTCGA      6680
CTGGACCAAG GTCACACTTG ATGGTCGCCC CCTTTCCACC      6720
ATCCAGCAGT ATTCAAAGAC CTTCTTTGTC CTGCCGCTCC      6760
GCGGTAAGCT CTCCTTTTGG GAGGCAGGAA CTACTAAAGC      6800
CGGGTACCCT TATAATTATA ACACCACTGC TAGTGACCAA      6840
CTGCTCGTTG AGAATGCCGC TGGGCATCGG GTTGCTATTT      6880
CCACCTACAC TACTAGCCTG GGTGCTGGCC CCGTCTCTAT      6920
TTCCGCGGTT GCTGTTTTAG CCCCCCACTC TGTGCTAGCA      6960
TTGCTTGAGG ATACCATGGA CTACCCTGCC CGCGCCCATA      7000
CTTTCGATGA CTTCTGCCCG GAGTGCCGCC CCCTTGGCCT      7040
CCAGGGTTGT GCTTTTCAGT CTACTGTCGC TGAGCTTCAG      7080
CGCCTTAAGA TGAAGGTGGG TAAAACTCGG GAGTTATAGT      7120
TTATTTGCTT GTGCCCCCCT TCTTTCTGTT GCTTATTT       7168
```

The abbreviations used for the nucleotides are those standardly used in the art.

The sequence in one direction has been designated by convention as the "plus" sequence since it is the protein-encoding strand of RNA viruses and this is the sequence shown above as SEQ ID. NO.:4.

The deduced amino acid sequences of the open reading frames of SAR-55 have SEQ ID NO. 1, SEQ ID NO. 2, and SEQ ID NO. 3. ORF-1 starts at nucleotide 28 of SEQ ID NO. 4 and extends 5078 nucleotides; ORF-2 starts at nucleotide 5147 of SEQ. ID NO. 4 and extends 1979 nucleotides; and ORF-3 starts at nucleotide 5106 of SEQ. ID NO. 4 and extends 368 nucleotides.

Variations are contemplated in the DNA sequence which will result in a DNA sequence that is capable of directing production of analogs of the ORF-2 protein. By "analogs of the ORF-2 protein" as used throughout the specification and claims is meant a protein having an amino acid sequence substantially identical to a sequence specifically shown herein where one or more of the residues shown in the sequences presented herein have been substituted with a biologically equivalent residue such that the resultant protein (i.e. the "analog") is capable of forming viral particles and is immunogenic. It should be noted that the DNA sequence set forth above represents a preferred embodiment of the present invention. Due to the degeneracy of the genetic code, it is to be understood that numerous choices of nucleotides may be made that will lead to a DNA sequence capable of directing production of the instant ORF proteins or their analogs. As such, DNA sequences which are functionally equivalent to the sequences set forth above or which are functionally equivalent to sequences that would direct production of analogs of the ORF proteins produced pursuant to the amino acid sequence set forth above, are intended to be encompassed within the present invention.

The present invention relates to a method for detecting the hepatitis E virus in biological samples based on selective amplification of hepatitis E gene fragments. Preferably, this method utilizes a pair of single-stranded primers derived from non-homologous regions of opposite strands of a DNA duplex fragment, which in turn is derived from a hepatitis E virus whose genome contains a region homologous to the SAR-55 sequence shown in SEQ ID No.: 4. These primers can be used in a method following the process for amplifying selected nucleic acid sequences as defined in U.S. Pat. No. 4,683,202.

The present invention also relates to the use of single-stranded antisense poly-or oligonucleotides derived from sequences homologous to the SAR-55 cDNA to inhibit the expression of hepatitis E genes. These anti-sense poly-or oligonucleotides can be either DNA or RNA. The targeted sequence is typically messenger RNA and more preferably, a signal sequence required for processing or translation of the RNA. The antisense poly- or oligonucleotides can be conjugated to a polycation such as polylysine as disclosed in Lemaitre, M. et al. (1989) Proc Natl Acad Sci USA 84:648–652; and this conjugate can be administered to a mammal in an amount sufficient to hybridize to and inhibit the function of the messenger RNA.

The present invention includes a recombinant DNA method for the manufacture of HEV proteins, preferably a protein composed of at least one ORF protein, most preferably at least one ORF-2 protein. The recombinant ORF protein may be composed of one ORF protein or a combination of the same or different ORF proteins. A natural or synthetic nucleic acid sequence may be used to direct production of the HEV proteins. In one embodiment of the invention, the method comprises:

(a) preparation of a nucleic acid sequence capable of directing a host organism to produce a protein of HEV;

(b) cloning the nucleic acid sequence into a vector capable of being transferred into and replicated in a host organism, such vector containing operational elements for the nucleic acid sequence;

(c) transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of a protein encoded by nucleic acids of HEV, preferably encoding by at least one ORF of HEV or a combination of the same or different ORF proteins, most preferably encoding at least one ORF-2 nucleic acid sequence, comprises:

(a) culturing a transformed or transfected host organism containing a nucleic acid sequence capable of directing the host organism to produce a protein, under conditions such that the protein is produced, said protein exhibiting substantial homology to a native HEV protein isolated from HEV having the amino acid sequence according to SEQ ID NO. 1, SEQ ID NO. 2 or SEQ ID NO. 3, or combinations thereof.

In one embodiment, the RNA sequence of the viral genome of HEV strain SAR-55 was isolated and cloned to cDNA as follows. Viral RNA is extracted from a biological sample collected from cynomolgus monkeys infected with SAR-55 and the viral RNA is then reverse transcribed and amplified by polymerase chain reaction using primers complementary to the plus or minus strands of the genome of a strain of HEV from Burma (Tam et al. (1991)) or the SAR-55 genome. The PCR fragments are subcloned into pBR322 or pGEM-32 and the double-stranded PCR fragments were sequenced.

The vectors contemplated for use in the present invention include any vectors into which a nucleic acid sequence as described above can be inserted, along with any preferred or required operational elements, and which vector can then be subsequently transferred into a host organism and replicated in such organism. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

In construction of the cloning vector of the present invention, it should additionally be noted that multiple copies of the nucleic acid sequence and its attendant operational elements may be inserted into each vector. In such an embodiment, the host organism would produce greater amounts per vector of the desired HEV protein. The number of multiple copies of the DNA sequence which may be inserted into the vector is limited only by the ability of the resultant vector due to its size, to be transferred into and replicated and transcribed in an appropriate host microorganism.

In another embodiment, restriction digest fragments containing a coding sequence for HEV proteins can be inserted into a suitable expression vector that functions in prokaryotic or eukaryotic cells. By suitable is meant that the vector is capable of carrying and expressing a complete nucleic acid sequence coding for HEV proteins, preferably at least one complete ORF protein. In the case or ORF-2, the expressed protein should form viral-like particles. Preferred expression vectors are those that function in a eukaryotic cell. Examples of such vectors include but are not limited to vectors useful for expression in yeast (e.g. pPIC9 vector-Invitrogen) vaccinia virus vectors, adenovirus or herpesviruses, preferably the baculovirus transfer vector, pBlueBac. Preferred vectors are p63-2, which contains the complete ORF-2 gene, and P59-4, which contains the complete ORF-3 and ORF-2 genes. These vectors were deposited with the American Type Culture Collection, 12301 Parklawn Drive, Rockville, Md. 20852 USA on Sep. 10, 1992 and have accession numbers 75299 (P63-2) and 75300 (P59-4). Example 1 illustrates the cloning of the ORF-2 gene into pBlueBac to produce p63-2. This method includes digesting the genome of HEV strain SAR-55 with the restriction enzymes NruI and BglII, inserting a polylinker containing BlnI and BglII sites into the unique NheI site of the vector and inserting the NruI-BglII ORF-2 fragment in BlnI-BglII PBlueBac using an adapter.

In yet another embodiment, the selected recombinant expression vector may then be transfected into a suitable eukaryotic cell system for purposes of expressing the recombinant protein. Such eukaryotic cell systems include, but are not limited to, yeast, and cell lines such as HeLa, MRC-5 or Cv-1. One preferred eukaryotic cell system is SF9 insect cells. One preferred method involves use of the pBlueBac expression vector where the insect cell line SF9 is cotransfected with recombinant pBlueBac and AcMNPV baculovirus DNA by the Ca precipitation method.

The expressed recombinant protein may be detected by methods known in the art which include Coomassie blue staining and Western blotting using sera containing anti-HEV antibody as shown in Example 2. Another method is the detection of virus-like particles by immunoelectron microscopy as shown in Example 3.

In a further embodiment, the recombinant protein expressed by the SF9 cells can be obtained as a crude lysate or it can be purified by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the recombinant protein may be purified by passage through a column containing a resin which has bound thereto antibodies specific for the ORF protein. An example of a protocol for the purification of a recombinantly expressed HEV ORF protein is provided in Example 10.

In another embodiment, the expressed recombinant proteins of this invention can be used in immunoassays for diagnosing or prognosing hepatitis E in a mammal including but not limited to humans, chimpanzees, Old World monkeys, New World monkeys, other primates and the like. In a preferred embodiment, the immunoassay is useful in diagnosing hepatitis E infection in humans. Immunoassays using the HEV proteins, particularly the ORF proteins, and especially ORF 2 proteins, provide a highly specific, sensitive and reproducible method for diagnosing HEV infections, in contrast to immunoassays which utilize partial ORF proteins. Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Methods in Immunodiagnosis*, 2nd Edition, Rose and Bigazzi, eds., John Wiley and Sons, 1980 and Campbell et al., *Methods of Immunology*, W.A. Benjamin, Inc., 1964, both of which are incorporated herein by reference. Such assays may be a direct, indirect, competitive, or noncompetitive immunoassay as described in the art. (Oellerich, M. 1984. *J. Clin. Chem. Clin*. BioChem. 22: 895–904) Biological samples appropriate for such detection assays include, but are not limited to, tissue biopsy extracts, whole blood, plasma, serum, cerebrospinal fluid, pleural fluid, urine and the like.

In one embodiment, test serum is reacted with a solid phase reagent having surface-bound recombinant HEV protein as an antigen, preferably an ORF protein or combination of different ORF proteins such as ORF-2 and ORF-3, ORF-1 and ORF-3 and the like. More preferably, the HEV protein is an ORF-2 protein that forms virus-like particles. The solid surface reagent can be prepared by known techniques for attaching protein to solid support material. These attachment methods include non-specific adsorption of the protein to the support or covalent attachment of the protein to a reactive group on the support. After reaction of the antigen with anti-HEV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

In a preferred embodiment, protein expressed by the recombinant vector pBlueBac containing the entire ORF-2 sequence of SAR-55 is used as a specific binding agent to detect anti-HEV antibodies, preferably IgG or IgM antibodies. Examples 4 and 5 show the results of an ELISA in which the solid phase reagent has recombinant ORF-2 as the surface antigen. This protein, encoded by the entire ORF-2 nucleic acid sequence, is superior to the partial ORF-2 proteins, as it is reactive with more antisera from different primate species infected with HEV than are partial antigens of ORF-2. The protein of the present invention is also capable of detecting antibodies produced in response to different strains of HEV but does not detect antibodies produced in response to Hepatitis A, B, C or Hepatitis D.

The HEV protein and analogs may be prepared in the form of a kit, alone, or in combinations with other reagents such as secondary antibodies, for use in immunoassays.

The recombinant HEV proteins, preferably an ORF protein or combination of ORF proteins, more preferably an ORF-2 protein and substantially homologous proteins and analogs of the invention can be used as a vaccine to protect mammals against challenge with Hepatitis E. The vaccine, which acts as an immunogen, may be a cell, cell lysate from cells transfected with a recombinant expression vector or a culture supernatant containing the expressed protein. Alternatively, the immunogen is a partially or substantially purified recombinant protein. While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen can be administered by any route appropriate for antibody production such as intravenous, intraperitoneal, intramuscular, subcutaneous, and the like. The immunogen may be administered once or at periodic intervals until a significant titer of anti-HEV antibody is produced. The antibody may be detected in the serum using an immunoassay.

In yet another embodiment, the immunogen may be nucleic acid sequence capable of directing host organism synthesis of an HEV ORF protein. Such nucleic acid sequence may be inserted into a suitable expression vector by methods known to those skilled in the art. Expression vectors suitable for producing high efficiency gene transfer in vivo include, but are not limited to, retroviral, adenoviral and vaccinia viral vectors. Operational elements of such expression vectors are disclosed previously in the present specification and are known to one skilled in the art. Such expression vectors can be administered intravenously, intramuscularly, subcutaneously, intraperitoneally or orally.

In an alternative embodiment, direct gene transfer may be accomplished via intramuscular injection of, for example, plasmid-based eukaryotic expression vectors containing a nucleic acid sequence capable of directing host organism synthesis HEC ORF protein(s). Such an approach has previously been utilized to produce the hepatitis B surface antigen in vivo and resulted in an antibody response to the surface antigen (Davis, H. L. et al. (1993) *Human Molecular Genetics*, 2:1847–1851; see also Davis et al. (1993) *Human Gene Therapy*, 4:151–159 and 733–740).

When the immunogen is a partially or substantially purified recombinant HEV ORF protein, dosages effective to elicit a protective antibody response against HEV range from about 2 μg to about 100 μg. A more preferred range is from about 5 μg to about 70 μg and a most preferred range is from about 10 μg to about 60 μg.

Dosages of HEV-ORF protein—encoding nucleic acid sequence effective to elicit a protective antibody response against HEV range from about 1 to about 5000 μg; a more preferred range being about 300 to about 1000 μg.

The expression vectors containing a nucleic acid sequence capable of directing host organism synthesis of an HEV ORF protein(s) may be supplied in the form of a kit, alone, or in the form of a pharmaceutical composition as described above.

The administration of the immunogen of the present invention may be for either a prophylactic or therapeutic purpose. When provided prophylactically, the immunogen is provided in advance of any exposure to HEV or in advance of any symptom due to HEV infection. The prophylactic administration of the immunogen serves to prevent or attenuate any subsequent infection of HEV in a mammal. When provided therapeutically, the immunogen is provided at (or shortly after) the onset of the infection or at the onset of any symptom of infection or disease caused by HEV. The therapeutic administration of the immunogen serves to attenuate the infection or disease.

A preferred embodiment is a vaccine prepared using recombinant ORF-2 protein expressed by the ORF-2 sequence of HEV strain SAR-55 and equivalents thereof. Since the recombinant ORF-2 protein has already been demonstrated to be reactive with a variety of HEV-positive sera, their utility in protecting against a variety of HEV strains is indicated.

In addition to use as a vaccine, the compositions can be used to prepare antibodies to HEV virus-like particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80: 15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedler al. 1988 J. Immunol. 141:4053, all incorporated herein by reference).

The antibodies or antigen binding fragments may also be produced by genetic engineering. The technology for expression of both heavy and light cain genes in *E. coli* is the subject the PCT patent applications; publication number WO 901443, WO901443, and WO 9014424 and in Huse et al., 1989 Science 246:1275–1281.

The antibodies can also be used as a means of enhancing the immune response. The antibodies can be administered in amounts similar to those used for other therapeutic administrations of antibody. For example, pooled gamma globulin is administered at 0.02–0.1 ml/lb body weight during the early incubation period of other viral diseases such as rabies, measles and hepatitis B to interfere with viral entry into cells. Thus, antibodies reactive with the HEV virus particle can be passively administered alone or in conjunction with another anti-viral agent to a host infected with an HEV to enhance the effectiveness of an antiviral drug.

Alternatively, anti-HEV antibodies can be induced by administering anti-idiotype antibodies as immunogens. Conveniently, a purified anti-HEV antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the FC region of the administered antibodies can be removed. Following induction of anti-idiotype antibody in the host animal, serum or plasma is removed to provide an antibody composition. The composition can be purified as described above for anti-HEV antibodies, or by affinity chromatography using anti-HEV antibodies bound to the affinity matrix. The anti-idiotype antibodies produced are similar in conformation to the authentic HEV-antigen and may be used to prepare an HEV vaccine rather than using an HEV particle antigen.

When used as a means of inducing anti-HEV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HEV derived proteins of the invention are also intended for use in producing antiserum designed for pre- or post-exposure prophylaxis. Here an HEV protein, or mixture of proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HEV serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis. Of course, those of skill in the art would readily understand that immune globulin (HEV immune globulin) purified from the antiserum of immunized individuals using standard techniques may be used as a pre-exposure prophylactic measure or in treating individuals post-exposure.

For both in vivo use of antibodies to HEV virus-like particles and proteins and anti-idiotype antibodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., NY, N.Y., pp. 56–97). To produce a human-human hybridoma, a human lymphocyte donor is selected. A donor known to be infected with HEV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to HEV virus particles. For monoclonal anti-idiotype antibodies, the antibodies must bind to anti-virus particle antibodies. Cells producing antibodies of the desired specificity are selected.

The above described antibodies and antigen binding fragments thereof may be supplied in kit form alone, or as a pharmaceutical composition for in vivo use. The antibodies may be used for therapeutic uses, diagnostic use in immunoassays or as an immunoaffinity agent to purify ORF proteins as described herein.

Material

The materials used in the Examples were as follows:

Primates. Chimpanzee (Chimp) (*Pan troglodytes*). Old world monkeys: cynomolgus monkeys (Cyno) (*Macaca fascicularis*), rhesus monkeys (Rhesus) (*M. mulatta*), pigtail monkeys (PT) (*M. nemestrina*), and African green monkeys (AGM) (*Cercopithecus aethiops*). New World monkeys: mustached tamarins (Tam) (*Saguinus mystax*), squirrel monkeys (SQM) (*Saimiri sciureus*) and owl monkeys (OWL) (*Aotus trivigatus*). Primates were housed singly under conditions of biohazard containment. The housing, maintenance and care of the animals met or exceeded all requirements for primate husbandry.

Most animals were inoculated intravenously with HEV, strain SAR-55 contained in 0.5 ml of stool suspension diluted in fetal calf serum as described in Tsarev, S. A. et al. (1992), *Proc. Natl. Acad. Sci USA*, 89:559–563; and Tsarev, S. A. et al. (1993), *J. Infect. Dis*. (167:1302–1306). Chimp-1313 and 1310 were inoculated with a pool of stools collected from 7 Pakistani hepatitis E patients.

Serum samples were collected approximately twice a week before and after inoculation. Levels of the liver enzymes serum alanine amino transferase (ALT), isocitrate dehydrogenase (ICD), and gamma glutamyl transferase (GGT) were assayed with commercially available tests (Medpath Inc., Rockville, Md.). Serologic tests were performed as described above.

EXAMPLE 1

Identification of the DNA Sequence of the Genome of HEV Strain SAR-55

Preparation of Virus RNA Template for PCR. Bile from an HEV-infected cynomolgus monkey (10 μl), 20% (wt/vol) SDS (to a final concentration of 1%), proteinase K (10 mg/ml; to a final concentration of 1 mg/ml), 1 μl of tRNA (10 mg/ml), and 3 μl of 0.5 M EDTA were mixed in a final volume of 250 μl and incubated for 30 min. at 55° C. Total nucleic acids were extracted from bile twice with phenol/chloroform, 1:1 (vol/vol), at 65° C. and once with chloroform, then precipitated by ethanol, washed with 95% ethanol, and used for RT-PCR. RT-PCR amplification of HEV RNA from feces and especially from sera was more efficient when RNA was more extensively purified. Serum (100 μl) or a 10% fecal suspension (200 μl) was treated as above with proteinase K. After a 30-min incubation, 300 μl of CHAOS buffer (4.2 M guanidine thiocyanate/0.5 N-lauroylsarocosine/0.025 M Tris-HCL, pH 8.0) was added. Nucleic acids were extracted twice with phenol/chloroform at 65° C. followed by chloroform extraction at room temperature. Then 7.5 M ammonium acetate (225 μl) was added to the upper phase and nucleic acids were precipitated with 0.68 ml of 2-propanol. The pellet was dissolved in 300 ul CHAOS buffer and 100 ul of $H_2O$ was added. Chloroform extraction and 2-propanol precipitation were repeated. Nucleic acids were dissolved in water, precipitated with ethanol, washed with 95% ethanol, and used for RT-PCR.

Primers. Ninety-four primers, 21–40 nucleotides (nt) long, and complementary to plus or minus strands of the genome of a strain of HEV from Burma (BUR-121) (Tam, A. W. et al. (1991), *Virology*, 185:120–131) or the SAR-55 genome were synthesized using an Applied Biosystems model 391 DNA synthesizer.

The sequences of these 94 primers are shown below starting with SEQ. ID NO. 5 and continuing to SEQ. ID NO. 98:

HEV Primer List

| Primer | ORF Region | Sequence | |
|---|---|---|---|
| D 3042 B | 1 | ACATTTGAATTCACAGACAT TGTGC | (SEQ. ID. NO. 5) |
| R 3043 B | 1 | ACACAGATCTGAGCTACATT CGTGAG | (SEQ. ID. NO. 6) |
| D 3044 B | 1 | AAAGGGATCCATGGTGTTTG AGAATGZ | (SEQ. ID. NO. 7) |
| R 3045 B | 1 | ACTCACTGCAGAGCACTATC GAATC | (SEQ. ID. NO. 8) |
| R 261 S | 1 | CGGTAAACTGGTACTGCACA AC | (SEQ. ID. NO. 9) |
| D 260 S | 1 | AAGTCCCGCTCTATTACCCA AG | (SEQ. ID. NO. 10) |
| D 259 S | 1 | ACCCACGGGTGTTGGTTTTT G | (SEQ. ID. NO. 11) |
| R 255 S | 1 | TTCTTGGGGCAGGTAGAGAA G | (SEQ. ID. NO. 12) |
| R 254 S | 2 | TTATTGAATTCATGTCAACG GACGTC | (SEQ. ID. NO. 13) |
| D 242 S | 1 | AATAATTCATGCCGTCGCTC C | (SEQ. ID. NO. 14) |
| R 241 S | 1 | AAGCTCAGGAAGGTACAACT C | (SEQ. ID. NO. 15) |
| R 231 S | 1 | AAATCGATGGCTGGGATCTG ATTC | (SEQ. ID. NO. 16) |
| R 230 S | 1 | GAGGCATTGTAGAGCTTTGT G | (SEQ. ID. NO. 17) |
| D 229 S | 1 | GATGTTGCACGGACAGCAAA TC | (SEQ. ID. NO. 18) |
| D 228 S | 1 | ATCTCCGATGCAATCGTTAA TAAC | (SEQ. ID. NO. 19) |
| D 227 B | 1 | TAATCCATTCTGTGGCGAGA G | (SEQ. ID. NO. 20) |
| R 218 B | 2 | AAGTGTGACCTTGGTCCAGT C | (SEQ. ID. NO. 21) |
| D 217 B | 2 | TTGCTCGTGCCACAATTCGC TAC | (SEQ. ID. NO. 22) |
| D 211 B | 1 | CATTTCACTGAGTCAGTGAA GZ | (SEQ. ID. NO. 23) |
| D 202 B | 2 | TAATTATAACACCACTGCTA G | (SEQ. ID. NO. 24) |
| R 201 B | 2 | GATTGCAATACCCTTATCCT G | (SEQ. ID. NO. 25) |
| R 200 S | 1 | ATTAAACCTGTATAGGGCAG AAC | (SEQ. ID. NO. 26) |
| R 199 S | 1 | AAGTTCGATAGCCAGATTTG C | (SEQ. ID. NO. 27) |
| R 198 S | 2 | TCATGTTGGTTGTCATAATC C | (SEQ. ID. NO. 28) |
| R 193 B | 1 | GATGACGCACTTCTCAGTGT G | (SEQ. ID. NO. 29) |
| R 192 B | 1 | AGAACAACGAACGGAGAAC | (SEQ. ID. NO. 30) |
| D 191 B | 1 | AGATCCCAGCCATCGACTTT G | (SEQ. ID. NO. 31) |
| R 190 S | 2 | TAGTAGTGTAGGTGGAAATA G | (SEQ. ID. NO. 32) |

-continued

HEV Primer List

| Primer | ORF Region | Sequence | |
|---|---|---|---|
| D 189 B | 2 | GTGTGGTTATTCAGGATTATG | (SEQ. ID. NO. 33) |
| D 188 B | 2 | ACTCTGTGACCTTGGTTAATG | (SEQ. ID. NO. 34) |
| R 187 S | 2 | AACTCAAGTTCGAGGGCAAAG | (SEQ. ID. NO. 35) |
| D 186 S | 2 | CGCTTACCCTGTTTAACCTTG | (SEQ. ID. NO. 36) |
| D 185 B | 2,3 | ATCCCCTATATTCATCCAACCAAC | (SEQ. ID. NO. 37) |
| D 184 S | 2,3 | CTCCTCATGTTTCTGCCTATG | (SEQ. ID. NO. 38) |
| R 181 S | 2 | GCCAGAACGAAATGGAGATAGC | (SEQ. ID. NO. 39) |
| R 180 B | 1 | CTCAGACATAAAACCTAAGTC | (SEQ. ID. NO. 40) |
| D 179 S | 1 | TGCCCTATACAGGTTTAATCG | (SEQ. ID. NO. 41) |
| D 178 B | 1 | ACCGGCATATACCAGGTGC | (SEQ. ID. NO. 42) |
| D 177 B | 2 | ACATGGCTCACTCGTAAATTC | (SEQ. ID. NO. 43) |
| R 174 B | 1 | AACATTAGACGCGTTAACGAG | (SEQ. ID. NO. 44) |
| D 173 S | 1 | CTCTTTTGATGCCAGTCAGAG | (SEQ. ID. NO. 45) |
| D 172 B | 1 | ACCTACCCGGATGGCTCTAAGG | (SEQ. ID. NO. 46) |
| R 166 B | 2 | TATGGGAATTCGTGCCGTCCTGAAG (EcoRI) | (SEQ. ID. NO. 47) |
| R 143 B | 1 | AGTGGGAGCAGTATACCAGCG | (SEQ. ID. NO. 48) |
| D 141 B | 1 | CTGCTATTGAGCAGGCTGCTC | (SEQ. ID. NO. 49) |
| R 142 S | 1 | GGGCCATTAGTCTCTAAAACC | (SEQ. ID. NO. 50) |
| D 135 B | 1 | GAGGTTTTCTGGAATCATC | (SEQ. ID. NO. 51) |
| R 134 B | 1 | GCATAGGTGAGACTG | (SEQ. ID. NO. 52) |
| R 133 B | 1 | AGTTACAGCCAGAAAACC | (SEQ. ID. NO. 53) |
| D 132 S | 2,3 | CCATGGATCCTCGGCCTATTTTGCTGTTGCTCC (Bam HI) | (SEQ. ID. NO. 54) |
| D 131 B | 5'NC | AGGCAGACCACATATGTG | (SEQ. ID. NO. 55) |
| R 119 B | 1 | GGTGCACTCCTGACCAAGCC | (SEQ. ID. NO. 56) |
| D 118 B | 1 | ATTGGCTGCCACTTTGTTC | (SEQ. ID. NO. 57) |
| R 117 B | 1 | ACCCTCATACGTCACCACAAC | (SEQ. ID. NO. 58) |
| R 116 B | 1 | GCGGTGGACCACATTAGGATTATC | (SEQ. ID. NO. 59) |
| D 115 B | 1 | CATGATATGTCACCATCTG | (SEQ. ID. NO. 60) |
| D 114 B | 1 | GTCATCCATAACGAGCTGG | (SEQ. ID. NO. 61) |
| R 112 B | 2 | AGCGGAATTCGAGGGCGGCATAAAGAACCAGG (EcoRI) | (SEQ. ID. NO. 62) |
| R 111 B | 2 | GCGCTGAATTCGGATCACAAGCTCAGAGGCTATGCC (EcoRI) | (SEQ. ID. NO. 63) |
| D 110 B | 2 | GTATAACGGATCCACATCTCCCCTTACCTC (Bam HI) | (SEQ. ID. NO. 64) |
| D 109 B | 2 | TAACCTGGATCCTTATGCCGCCCCTCTTAG (Bam HI) | (SEQ. ID. NO. 65) |
| D 108 B | 1 | AAATTGGATCCTGTGTCGGGTGGAATGAATAACATGTC (BamHI) | (SEQ. ID. NO. 66) |
| R 107 B | 1 | ATCGGCAGATCTGATAGAGCGGGGACTTGCCGGATCC | (SEQ. ID. NO. 67) |
| D 101 B | 2 | TACCCTGCCCGCGCCCATACTTTTGATG | (SEQ. ID. NO. 68) |
| R 100 B | 1 | GGCTGAGATCTGGTTCGGGTCGCCAAGAAGGTG (Bgl II) | (SEQ. ID. NO. 69) |
| R 99 B | 2 | TACAGATCTATACAACTTAACAGTCGG (Bgl II) | (SEQ. ID. NO. 70) |
| R 98 B | 2 | GCGGCAGATCTCACCGACACCATTAGTAC (Bgl II) | (SEQ. ID. NO. 71) |
| D 97 S | 1 | CCGTCGGATCCCAGGGGCTGCTGTCCTG (Bam HI) | (SEQ. ID. NO. 72) |
| R 96 B | 2 | AAAGGAATTCAAGACCAGAGGTAGCCTCCTC (EcoRI) | (SEQ. ID. NO. 73) |
| D 95 B | 2 | GTTGATATGAATTCAATAACCTCGACGG | (SEQ. ID. NO. 74) |
| R 94 B | 3'NC | TTTGGATCCTCAGGGAGCGCGGAACGCAGAAATGAG (BamHI) | (SEQ. ID. NO. 75) |
| D 90 B | 2 | TCACTCGTGAATTCCTATACTAATAC (EcoRI) | (SEQ. ID. NO. 76) |
| R 89 B | 3'NC | TTTGGATCCTCAGGGAGCGCGGAACGCAGAAATG (BamHI) | (SEQ. ID. NO. 77) |
| R 88 B | 1 | TGATAGAGCGGGACTTGCCGGATCC (BamHI) | (SEQ. ID. NO. 78) |
| R 87 B | 1 | TTGCATTAGGTTAATGAGGATCTC | (SEQ. ID. NO. 79) |
| D 86 B | 1 | ACCTGCTTCCTTCAGCCTGCAGAAG | (SEQ. ID. NO. 80) |
| R 81 B | 1 | GCGGTGGATCCGCTCCCAGGCGTCAAAAC (BamHI) | (SEQ. ID. NO. 81) |
| D 80 B | 1 | GGGCGGATCGAATTCGAGACCCTTCTTGG (EcoRI) | (SEQ. ID. NO. 82) |
| R 79 B | 1 | AGGATGGATCCATAAGTTACCGATCAG (BamHI) | (SEQ. ID. NO. 83) |
| D 78 B | 1 | GGCTGGAATTCCTCTGAGGACGCCCTCAC (EcoRI) | (SEQ. ID. NO. 84) |
| R 77 B | 1 | GCCGAAGATCTATCGGACATAGACCTC (Bgl II) | (SEQ. ID. NO. 85) |
| R 76 B | 2 | CAGACGACGGATCCCCCTTGGATATAGCCTG (BamHI) | (SEQ. ID. NO. 86) |
| D 75 B | 5'NC | GGCCGAATTCAGGCAGACCACATATGTGGTCGATGCCATG (EcoRI) | (SEQ. ID. NO. 87) |
| D 72 B | 1 | GCAGGTGTGCCTGGATCCGGCAAGT (BamHI) | (SEQ. ID. NO. 88) |
| R 71 B | 1 | GTTAGAATTCCGGCCCAGCTGTGGTAGGTC (EcoRI) | (SEQ. ID. NO. 89) |
| D 63 B | 1 | CCGTCCGATTGGTCTGTATGCAGG | (SEQ. ID. NO. 90) |
| D 61 B | 1 | TACCAGTTTACTGCAGGTGTGC | (SEQ. ID. NO. 91) |
| D 60 B | 1 | CAAGCCGATGTGGACGTTGTCG | (SEQ. ID. NO. 92) |
| R 59 B | 2,3 | GGCGCTGGGCCTGGTCACGCCAAG | (SEQ. ID. NO. 93) |
| D 50 B | 1 | GCAGAAACTAGTGTTGACCCAG | (SEQ. ID. NO. 94) |
| R 49 B | 2 | TAGGTCTACGACGTGAGGCAAC | (SEQ. ID. NO. 95) |
| R 48 B | 1 | TACAATCTTTCAGGAAGAAGG | (SEQ. ID. NO. 96) |
| R 47 B | 1 | CCCACACTCCTCCATAATAGC | (SEQ. ID. NO. 97) |
| D 46 B | 1 | GATAGTGCTTTGCAGTGAGTACCG | (SEQ. ID. NO. 98) |

The abbreviations to the left of the sequences represent the following: R and D refer to reverse and forward primers, respectively; B and S refer to sequences derived from the Burma-121 Strain of Hepatitis E and the SAR-55 Strain of Hepatitis E, respectively; 5'NC and 3'NC refer to 5 prime and 3 prime non-coding regions of the HEV genome, respectively; and 1, 2 and 3 refer to sequence derived from open reading frames 1, 2 or 3, respectively. The symbol ( ) to the right of some sequences shown indicates insertion of an artificial restriction site into these sequences.

For cloning of PCR fragments, EcoRI, BamHI, or BglII restriction sites preceded by 3–7 nt were added to the 5' end of primers.

RT-PCR. The usual 100-µl RT-PCR mixture contained template, 10 mM Tris-HCL (ph 8.4), 50 mM KCl, 2.5 mM $MgCl_2$, all four dNTPs (each at 0.2 mM), 50 pmol of direct primer, 50 pmol of reverse primer, 40 units of RNasin (Promega), 16 units of avian myeloblastosis virus reverse transcriptase (Promega), 4 units of AmpliTaq (Cetus), under 100 µl of light mineral oil. The mixture was incubated 1 h at 42° C. and then amplified by 35 PCR cycles; 1 min at 94° C., 1 min at 45° C., and 1 min at 72° C. The PCR products were analyzed on 1% agarose gels.

Cloning of PCR Fragments. PCR fragments containing restriction sites at the ends were digested with EcoRI and BamHI or EcoRI and BglII restriction enzymes and cloned in EcoRI/BamHI-digested pBR322 or PGEM-3Z (Promega). Alternatively, PCR fragments were cloned into pCR1000 (Invitrogen) using the TA cloning kit (Invitrogen).

Sequencing of PCR Fragments and Plasmids. PCR fragments were excised from 1% agarose gels and purified by Geneclean (Bio 101, La Jolla, Calif.). Double-stranded PCR fragments were sequenced by using Sequenase (United States Biochemical) as described in Winship, P. R. (1984), *Nucleic Acids Rev.*, 17:1266. Double-stranded plasmids purified through CsCl gradients were sequenced with a Sequenase kit (United States Biochemical).

Computer Analysis of Sequences. Nucleotide sequences of HEV strains were compared using the Genetics Computer Group (Madison, Wis.) software package (Devereaux, J. et al. (1984), *Nucleic Acids Rev.*, 12:387–395, version 7.5, on a VAX 8650 computer (at the National Cancer Institute, Frederick, Md.)).

EXAMPLE 2

Construction of a Recombinant Expression Vector, P63-2

A plasmid containing the complete ORF-2 of the genome of HEV strain SAR-55, Tsarev, S. A. et al. (1992), *Proc. Natl. Acad. Sci. USA*, 89:559–563), was used to obtain a restriction fragment NruI-BglII. NruI cut the HEV cDNA five nucleotides upstream of the ATG initiation codon of ORF-2. An artificial Bgl II site previously had been placed at the 3' end of HEV genome just before the poly A sequence (Tsarev, S. A. et al. (1992), *Proc. Natl. Acad. Sci. USA*, 89:559–563). To insert this fragment into pBlueBac-Transfer vector (Invitrogen) a synthetic polylinker was introduced into the unique NheI site in the vector. This polylinker contained Bln I and Bgl II sites which are absent in both HEV cDNA and pBlueBac sequences. The NruI-BglII ORF-2 fragment was inserted in Bln I-BglII pBlueBac using an adapter as shown in FIG. 1.

EXAMPLE 3

Expression of P63-2 in SF9 Insect Cells p63-2 and AcMNPV baculovirus DNA (Invitrogen) were cotransfected into SF9 cells (Invitrogen) by the Ca precipitation method according to the Invitrogen protocol—By following this protocol; the ACMNPV baculovirus DNA can produce a live intact baculovirus which can package p63-2 to form a recombinant baculovirus. This recombinant baculovirus was plaque-purified 4 times. The resulting recombinant baculovirus 63-2-IV-2 was used to infect SF9 cells.

SDS-PAGE and Western blot. Insect cells were resuspended in loading buffer (50 mM Tris-HCl, pH 6.8, 100 mM DTT, 2% SDS, 0.1% bromphenol blue and 10% glycerol) and SDS-polyacrylamide gel electrophoresis was performed as described, Laemmli, U. K. (1970), *Nature*, 227:680. Gels were stained with coomassie blue or proteins were electroblotted onto BA-85 nitrocellulose filters (Schleicher & Schuell). After transfer, nitrocellulose membranes were blocked in PBS containing 10% fetal calf serum and 0.5% gelatin. As a primary antibody, hyperimmune serum of chimpanzee-1313 diluted 1:1000 was used. As a secondary antibody, phosphatase-labeled affinity-purified goat antibody to human IgG (Kirkegaard & Perry Laboratories, Inc.) diluted 1:2000 was used. Filters were developed in Western blue stabilized substrate for alkaline phosphatase (Promega). All incubations were performed in blocking solution, and washes were with PBS with 0.05% Tween-20 (Sigma).

Expression of HEV ORF-2. The major protein synthesized in SF9 cells infected with recombinant baculovirus 63-2-IV-2 was a protein with an apparent molecular weight of 74 KD (FIG. 2A, lane 3). This size is a little larger than that predicted for the entire ORF-2 (71 KD). The size difference could be due to glycosylation of the protein since there is at least one potential site of glycosylation (Asn-Leu-Ser) in the N-terminal part. This protein was not detected in noninfected cells (FIG. 2A, lane 1) or in cells infected with wild-type nonrecombinant baculovirus (FIG. 2A, lane 2). In the latter case, the major protein detected was a polyhedron protein. When the same lysates were analyzed by Western blot (FIG. 2B) with serum of chimp-1313 (hyperimmunized with HEV), only proteins in the recombinant cell lysate reacted (lane 3) and the major band was again represented by a 74 KD protein (FIG. 2B). Minor bands of about, 25, 29, 35, 40–45 and 55–70 kDa present in the Coomassie-stained gel (FIG. 2A, lane 3) also reacted with serum in the Western blot (FIG. 2B, lane 3). Some of the bands having molecular weights higher than 74 KD result from different extents of glycosylation while the lower molecular weight bands could reflect processing and/or degradation. Serum drawn from Chimp-1313 prior to inoculation with HEV did not react with any of the proteins by Western blot.

EXAMPLE 4

Figure 3B:
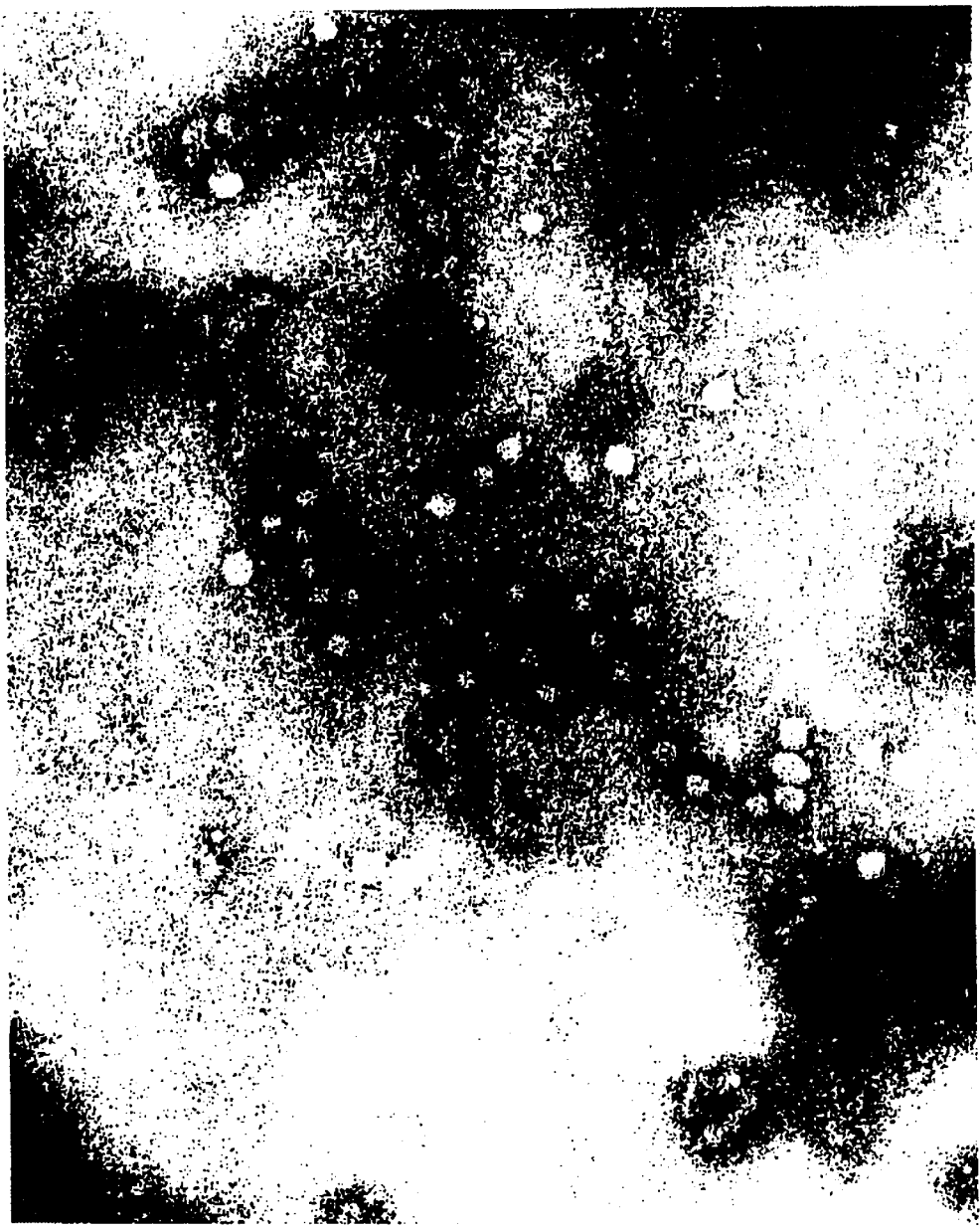
FIGS. 3A–3A''' and 3B show immunoelectron micrographs (IEM) of 30 and 20 nm virus-like particles respectively, which are formed as a result of the expression of ORF-2 protein in recombinant infected insect cells.

Immunoelectron Microscopy of Recombinant Infected SF9 Cells $5×10^6$ recombinant infected SF9 cells were sonicated in CsCl (1.30 g/ml) containing 10 mM Tris-HCl, pH 7.4, 0.3% sarcosyl and centrifuged 68 h, at 40,000 rpm (SW60Ti). 50 ul of the fraction, which had the highest ELISA response and a buoyant density of 1.30 g/ml was diluted in 1 ml PBS and 5 ul of chimp-1313 hyperimmune serum was added. The hyperimmune serum was prepared by rechallenging a previously infected chimp with a second strain of hepatitis E (Mexican HEV). Samples were incubated 1 h at room temperature and then overnight at 4° C. Immune complexes were precipitated using a SW60Ti rotor at 30,000 rpm, 4° C., 2 h. Pellets were resuspended in distilled water, negatively stained with 3% PTA, placed on carbon grids and examined at a magnification of 40,000 in an electron microscope EM-10, Carl Zeiss, Oberkochen, Germany.

Detection of VLPs. Cell lysates from insect cells infected with wild-type or recombinant baculovirus 63-2-IV-2 were fractionated by CsCl density centrifugation. When fractions of the CsCl gradient from the recombinant infected insect cells were incubated with Chimp-1313 hyperimmune serum, two kinds of virus-like particles (VLP) covered with antibody were observed in the fraction with buoyant density of 1.30 g/ml: first (FIG. 3A–3A'''), antibody covered individual particles that had a size (30 nm) and morphological structure suggestive of HEV, second (FIG. 3B), antibody-coated aggregates of particles smaller than HEV (about 20 nm) but which otherwise resembled HEV. Direct EM showed the presence of a very heterogenous population of objects including some of 30 and 20 nm in diameter respectively, which looked like virus particles but, in the absence of bound antibody, could not be confirmed as HEV. A number of IEM experiments suggested that at least some of the protein(s) synthesized from the ORF-2 region of the HEV genome, had assembled into a particulate structure. It was observed that insect cells at a later stage of infection, when the proportion of smaller proteins was higher, consistently gave better results in ELISA. Therefore, unfractionated lysates of recombinant insect cells from a later stage of infection were used as antigen in ELISA in subsequent tests.

EXAMPLE 5

Detection by ELISA Based on Antigen from Insect Cells Expressing Complete ORF-2 of Anti-HEV Following Infection with Different Strains of HEV $5 \times 10^6$ SF9 cells infected with 63-2-IV-2 virus were resuspended in 1 ml of 10 mM Tris-HCl, pH 7.5, 0.15M NaCl then were frozen and thawed 3 times. 10 ul of this suspension was dissolved in 10 ml of carbonate buffer (pH 9.6) and used to cover one flexible microtiter assay plate (Falcon). Serum samples were diluted 1:20, 1:400 and 1:8000, or 1:100, 1:1000 and 1:10000. The same blocking and washing solutions as described for the Western blot were used in ELISA. As a secondary antibody, peroxidase-conjugated goat IgG fraction to human IgG or horse radish peroxidase-labelled goat anti-Old or anti-New World monkey immunoglobulin was used. The results were determined by measuring the optical density (O.D.) at 405 nm.

Figure 4:
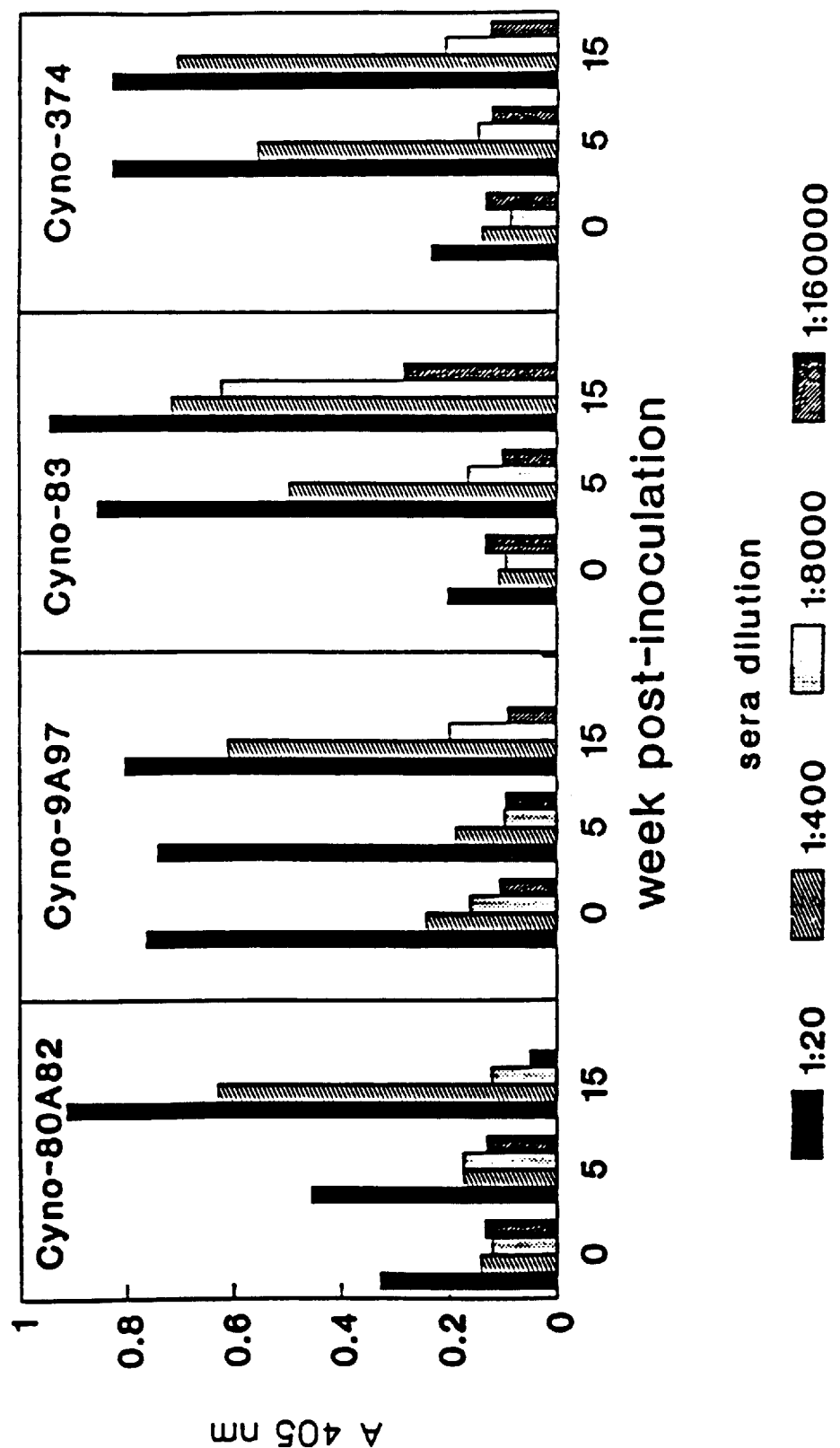
FIG. 4 shows the results of an ELISA using as the antigen, recombinant ORF-2 which was expressed from insect cells containing the gene encoding the complete ORF-2. Serum anti-HEV antibody levels were determined at various times following inoculation of cynomolgus monkeys with either the Mexican (Cyno-80A82, Cyno-9A97 and Cyno 83) or Pakistani (Cyno-374) strains of HEV.

To determine if insect cell-derived antigen representing a Pakistani strain of HEV could detect anti-HEV antibody in cynomolgus monkeys infected with the Mexican strain of HEV, 3 monkeys were examined (FIG. 4). Two monkeys cyno-80A82 and cyno-9A97, were infected with feces containing the Mexico '86 HEV strain (Ticehurst, J. et al. (1992), *J. Infect. Dis.*, 165:835–845) and the third monkey cyno-83 was infected with a second passage of the same strain. As a control, serum samples from cyno-374, infected with the Pakistani HEV strain SAR-55, were tested in the same experiment. All 3 monkeys infected with the Mexican strain seroconverted to anti-HEV. Animals from the first passage seroconverted by week 15 and from the second passage by week 5. Interestingly, the highest anti-HEV titer among the 4 animals, was found in cyno-83, inoculated with the second passage of the Mexican strain. Cynos inoculated with the first passage of the Mexican strain developed the lowest titers while those inoculated with the first passage of the Pakistani strain developed intermediate titers.

EXAMPLE 6

Specificity of Anti-HEV ELISA Based on Antigen from Insect Cells Expressig Complete ORF-2

To estimate if the ELISA described here specifically detected anti-HEV to the exclusion of any other type of hepatitis related antibody, serum samples of chimps were analyzed, in sets of four, infected with the other known hepatitis viruses (Garci, P. et al. (1992), *J. Infect. Dis.*, 165:1006–1011; Farci, P. et al. (1992), *Science* (in press); Ponzetto, A. et al. (1987) *J Infect. Dis.*, 155: 72–77; Rizzetto; m.et al. (1981) Hepatology 1: 567–574; reference for chimps—1413, 1373, 1442, 1551 (HAV); and for chimps—982, 1442, 1420, 1410 (HBV); is unpublished data from Purcell et al) (Table 1). Samples of pre-inoculation and 5 week and 15 week post-inoculation sera were analyzed in HEV ELISA at serum dilutions of 1:100, 1:1000 and 1:10000. None of the sera from animals infected with HAV, HBV, HCV and HDV reacted in the ELISA for HEV antibody, but all 4 chimps inoculated with HEV developed the IgM and IgG classes of anti-HEV.

TABLE 1

Serological assay of anti-HEV antibody in chimpanzees infected with different hepatitis viruses (Hepatitis A, B, C, D, E)

| chimp | inoculated virus | week of seroconversion for inoculated virus | preserum | | 5 | | 15 | | 20/25 | |
|---|---|---|---|---|---|---|---|---|---|---|
| | | | IgG | IgM | IgG | IgM | IgG | IgM | IgG | IgM |
| Chimp-1413 | HAV | 5 | — | — | — | — | — | — | | |
| Chimp-1373 | HAV | 7 | — | — | — | — | — | — | | |
| Chimp-1442 | HAV | 5 | — | — | — | — | — | — | — | — |
| Chimp-1451 | HAV | 5 | — | — | — | — | — | — | | |
| Chimp-982 | HBV | 3 | — | — | — | — | — | — | | |
| Chimp-1442 | HBV | 7 | — | — | — | — | — | — | | |
| Chimp-1420 | HBV | 9 | — | — | — | — | — | — | | |
| Chimp-1410 | HBV | 5 | — | — | — | — | — | — | | |
| Chimp-51 | HCV | 10 | — | — | — | — | — | — | | |
| Chimp-502 | HCV | 12 | — | — | — | — | — | — | | |
| Chimp-105 | HCV | 28 | — | — | — | — | — | — | | |
| Chimp-793 | HCV | 13 | — | — | — | — | — | — | | |
| Chimp-904 | HDV | 8 | — | — | — | — | — | — | | |
| Chimp-814 | HDV | 7 | — | — | — | — | — | — | | |
| Chimp-800 | HDV | 10 | — | — | — | — | — | — | | |
| Chimp-29 | HDV | 10 | — | — | — | — | — | — | — | — |
| Chimp-1310 | HEV | 5 | — | — | 1:10,000 | 1:100 | 1:10,000 | — | | |
| Chimp-1374 | HEV | 3 | — | — | 1:8000 | —* | 1:8000 | — | | |

TABLE 1-continued

Serological assay of anti-HEV antibody in chimpanzees infected with different hepatitis viruses (Hepatitis A, B, C, D, E)

| chimp | inoculated virus | week of seroconversion for inoculated virus | preserum IgG | preserum IgM | weeks post-inoculation 5 IgG | 5 IgM | 15 IgG | 15 IgM | 20/25 IgG | 20/25 IgM |
|---|---|---|---|---|---|---|---|---|---|---|
| Chimp-1375 | HEV | 3 | — | — | 1:8000 | 1:400 | 1:400 | — | | |
| Chimp-1313 | HEV1st*** | 5 | — | — | 1:10,000 | 1:100 | 1:1000 | — | | |
| Chimp-1313 | HEV2nd*** | 0.5 | 1:100 | — | 1:10,000 | — | 1:10,000 | — | | |

*Chimp-1374 was positive for IgM anti-HEV three and four weeks post-inoculation (see FIG. 5)
***Chimp-1313 was inoculated with HEV twice. 1st inoculation with pooled samples of 7 Pakistani patients. 2nd inoculation 45 months later with Mexican strain of HEV.

EXAMPLE 7

Determination of the Host Range of the SAR-55 Strain of HEV in Non-Human Primates Different primate species were inoculated intravenously with a standard stool suspension of HEV and serial serum samples were collected to monitor for infection. Serum ALT levels were determined as an indicator of hepatitis while seroconversion was defined as a rise in anti-HEV. The results were compared with those obtained in cynomolgus monkeys and chimpanzees.

Both rhesus monkeys inoculated with HEV (Table 2) demonstrated very prominent peaks of alanine aminotransferase activity as well as a strong anti-HEV response. The peak of alanine aminotransferase activity was observed on day 35 for both animals, and seroconversion occurred on day 21. The maximum titer of anti-HEV was reached on day 29. Both African green monkeys used in this study (Table 2) developed increased alanine aminotransferase activity and anti-HEV. Although African green money 230 died 7 weeks after inoculation, proof of infection was obtained before that time. Peak alanine aminotransferase activity for monkey 74 exceeded the mean value of preinoculation sera by about three times and for monkey 230 by about five times. Peaks of alanine aminotransferase activity and seroconversion appeared simultaneously on days 28 and 21 in monkeys 74 and 230, respectively.

TABLE 2

Biochemical and serologic profiles of HEV infection in eight primate species.

| Animal | Alanine aminotransferase (units/L) Preinoculation, mean (SD) | Day | Value | Anti-HEV IgG Day first detected (titer) | Maximum titer |
|---|---|---|---|---|---|
| Chimpanzee | | | | | |
| 1374 | 51(12) | 27 | 114 | 27(1:400) | 1:8000 |
| 1375 | 41(14) | 27 | 89 | 27(1:400) | 1:8000 |
| Cynomolgus monkey | | | | | |
| 374* | 46(20) | 26 | 608 | 19(1:400) | 1:8000 |
| 381* | 94(19) | 35 | 180 | 28(1:20) | 1:8000 |
| Rhesus monkey | | | | | |
| 726 | 43(6) | 35 | 428 | 21(1:20) | 1:8000 |
| 938 | 29(10) | 35 | 189 | 21(1:20) | 1:8000 |
| African green monkey | | | | | |
| 74 | 72(21) | 28 | 141 | 28(1:400) | 1:8000 |
| 230 | 102(45) | 21 | 334 | 21(1:8000) | 1:8000 |
| Pigtail macaque | | | | | |
| 98 | 37(8) | 21 | 47 | 21(1:400) | 1:8000 |
| 99 | 41(6) | 28 | 59 | 21(1:400) | 1:8000 |
| Tamarin | | | | | |
| 616 | 28(7) | 70 | 41 | — | |
| 636 | 19(4) | 7, 56 | 30 | — | |

TABLE 2-continued

Biochemical and serologic profiles of HEV infection in eight primate species.

| Animal | Alanine aminotransferase (units/L) | | | Anti-HEV IgG | |
|---|---|---|---|---|---|
| | Preinoculation, mean (SD) | Day | Value | Day first detected (titer) | Maximum titer |
| Squirrel monkey | | | | | |
| 868 | 90(35) | 40 | 355 | 41(1:20) | 1:20 |
| 869 | 127(63) | 42 | 679 | 35(1:20) | 1:20 |
| Owl monkey | | | | | |
| 924 | 41(7) | 35 | 97 | 21(1:20) | 1:8000 |
| 925 | 59(6) | 49, 91† | 78,199† | 21(1:20) | 1:8000 |

NOTE
—no anti-HEV detected.
*Previously studied using fragments of HEV proteins expressed in bacteria as antigen [18].
†Biomodol elevation of alanine aminotransferase.
SD standard deviation.

Pigtail macaque 99 demonstrated an increase in alanine aminotransferase activity >3 SD above the mean value of preinoculation sera, while pigtail macaque 98 did not. However, both monkeys seroconverted on day 21 and the anti-HEV titers were equivalent to those of the chimpanzees and Old World monkeys. Because of the low peak alanine aminotransferase values in the pigtail macaques, the possibility of immunization instead of infection with HEV cannot be completely ruled out. However, immunization is unlikely for several reasons. First, immunization in either of 2 tamarins, which are only one-fourth as large as the pigtail macaques but received the same amount of inoculum was not observed. Second, it is well known that the amount of HEV excreted in feces is usually very small, and 0.5 mL of the 10% suspension of feces used in this study is unlikely to contain an amount of antigen sufficient to immunize an animal, especially when inoculated intraveneously.

Neither tamarin inoculated in this study had a significant rise in alanine aminotransferase activity or development of anti-HEV (Table 2). Therefore, these animals did not appear to be infected. The squirrel monkeys did develop anti-HEV, but at significantly lower levels than chimpanzees or Old World monkeys (Table 2). In addition, seroconversion occured later in other animals. Squirrel monkey 868 seroconverted on day 41 and 869 on day 35. The anti-HEV titer was not >1:20 at any time during >3 months of monitoring and clearly was waning in both animals after reaching a peak value on days 47–54. However, the increases in alanine aminotransferase activity were rather prominent in both animals and were temporally related to the time of seroconversion.

The owl monkeys responded to HEV infection about as well as the Old World monkey species (Table 2). Both owl monkeys seroconverted on day 21 and by day 28 the anti-HEV titer had reached a value of 1:8000. Alanine amino-transferase activity raked on day 35 in owl monkey 924 but not until day 49 in monkey 925.

EXAMPLE 8

Detection of IgM and IgG Anti-HEV in Chimps

Figure 5A:
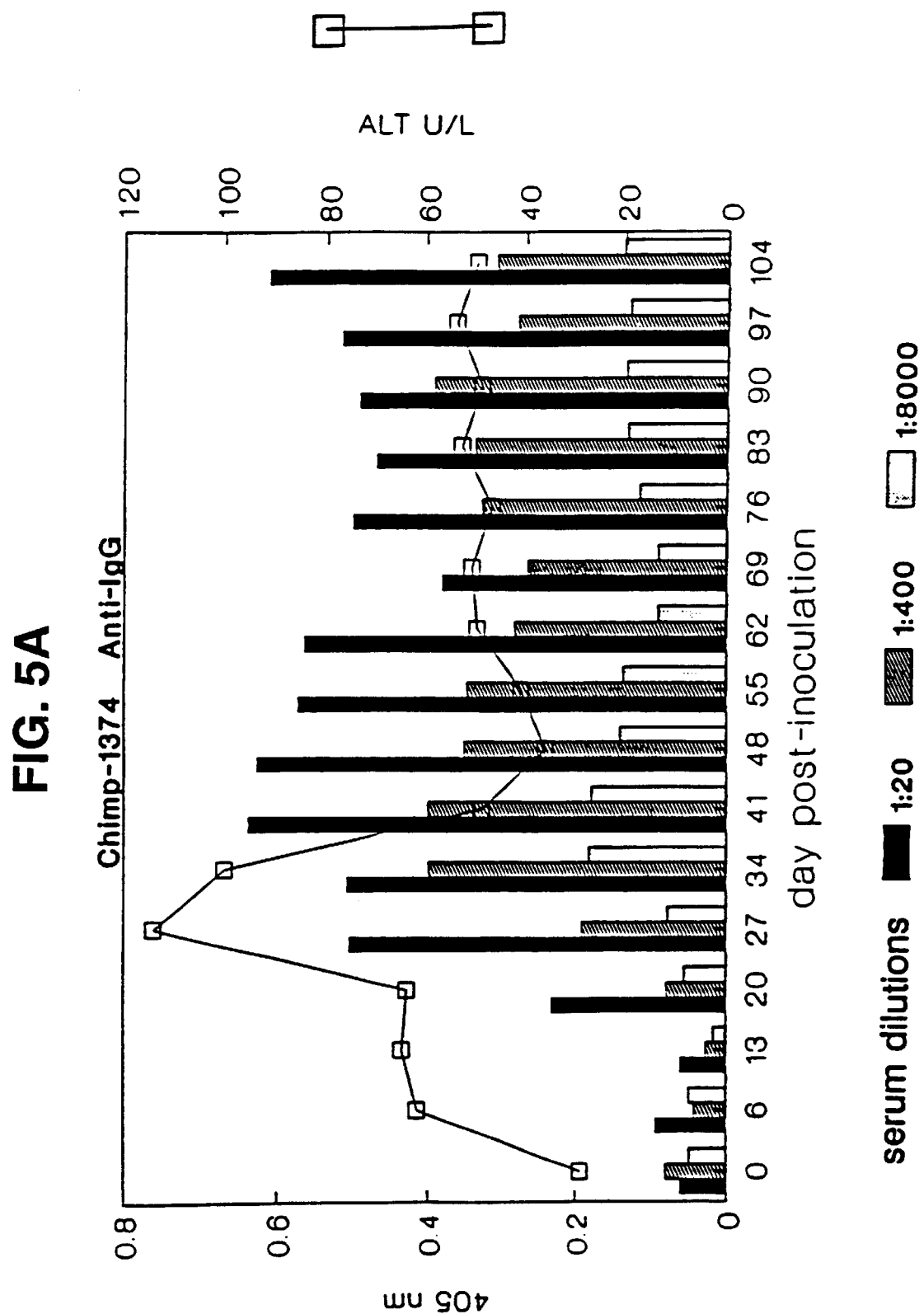
Figure 5B:
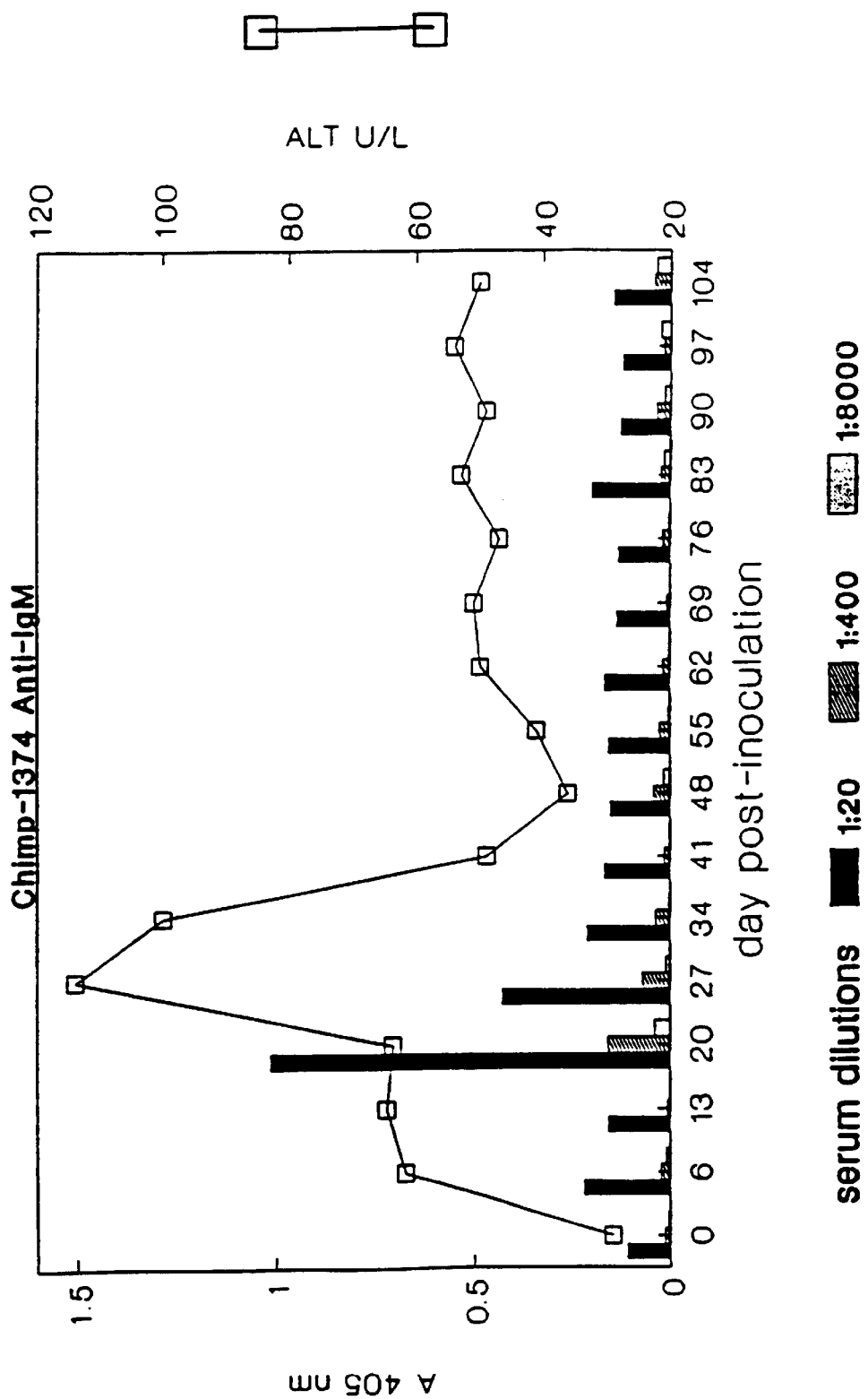
Figure 5C:
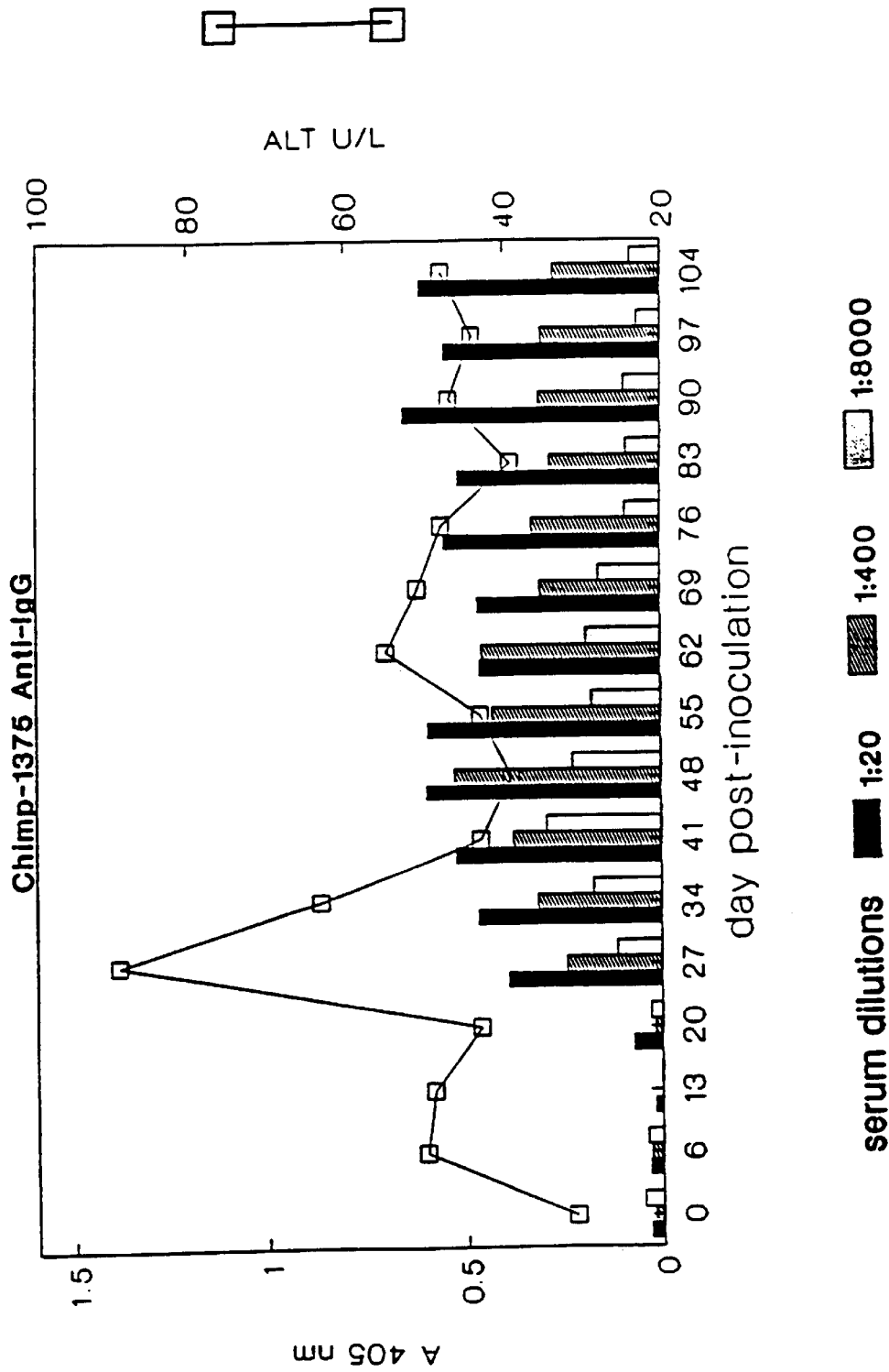
Figure 6A:
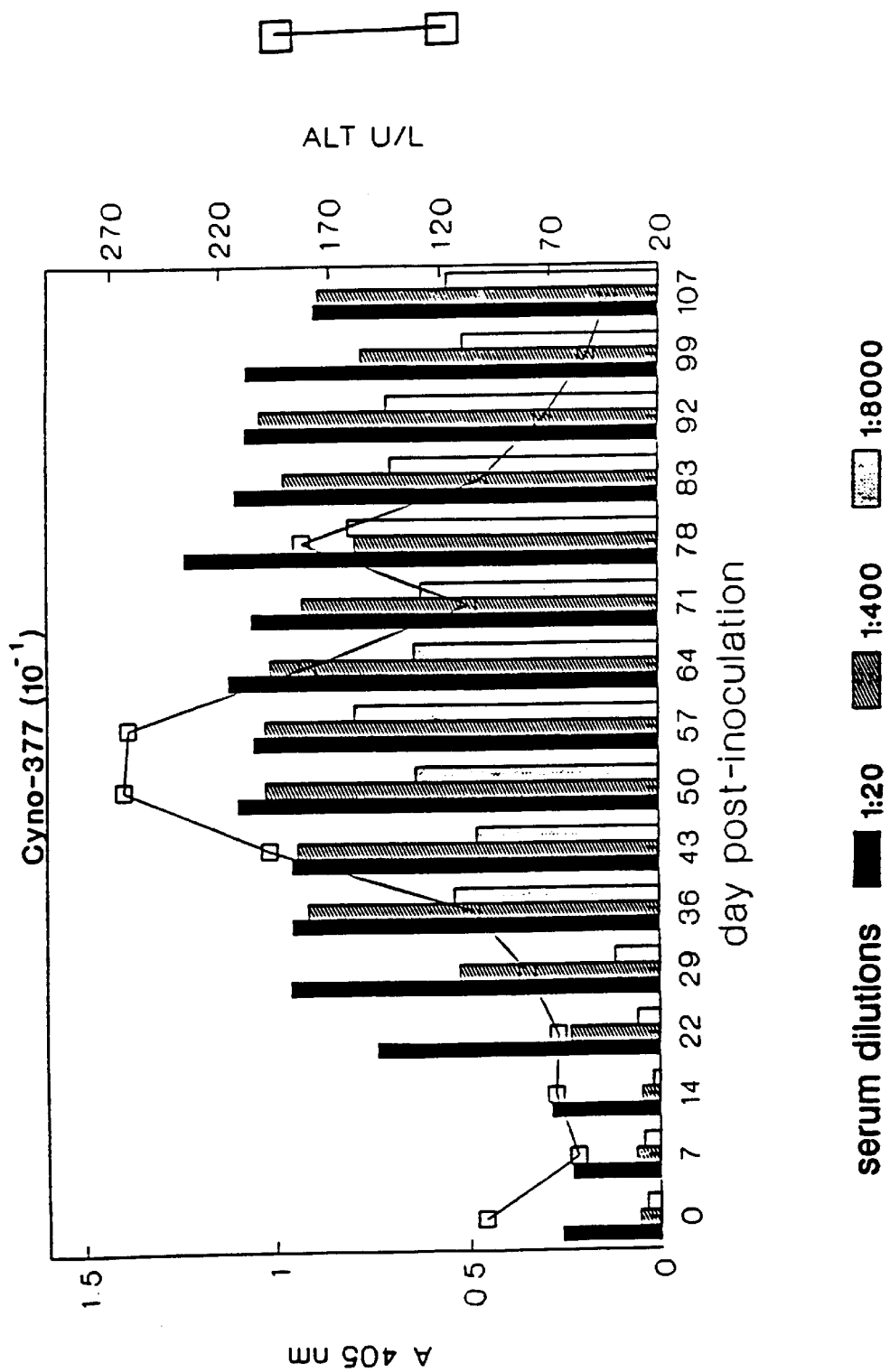
Figure 6C:
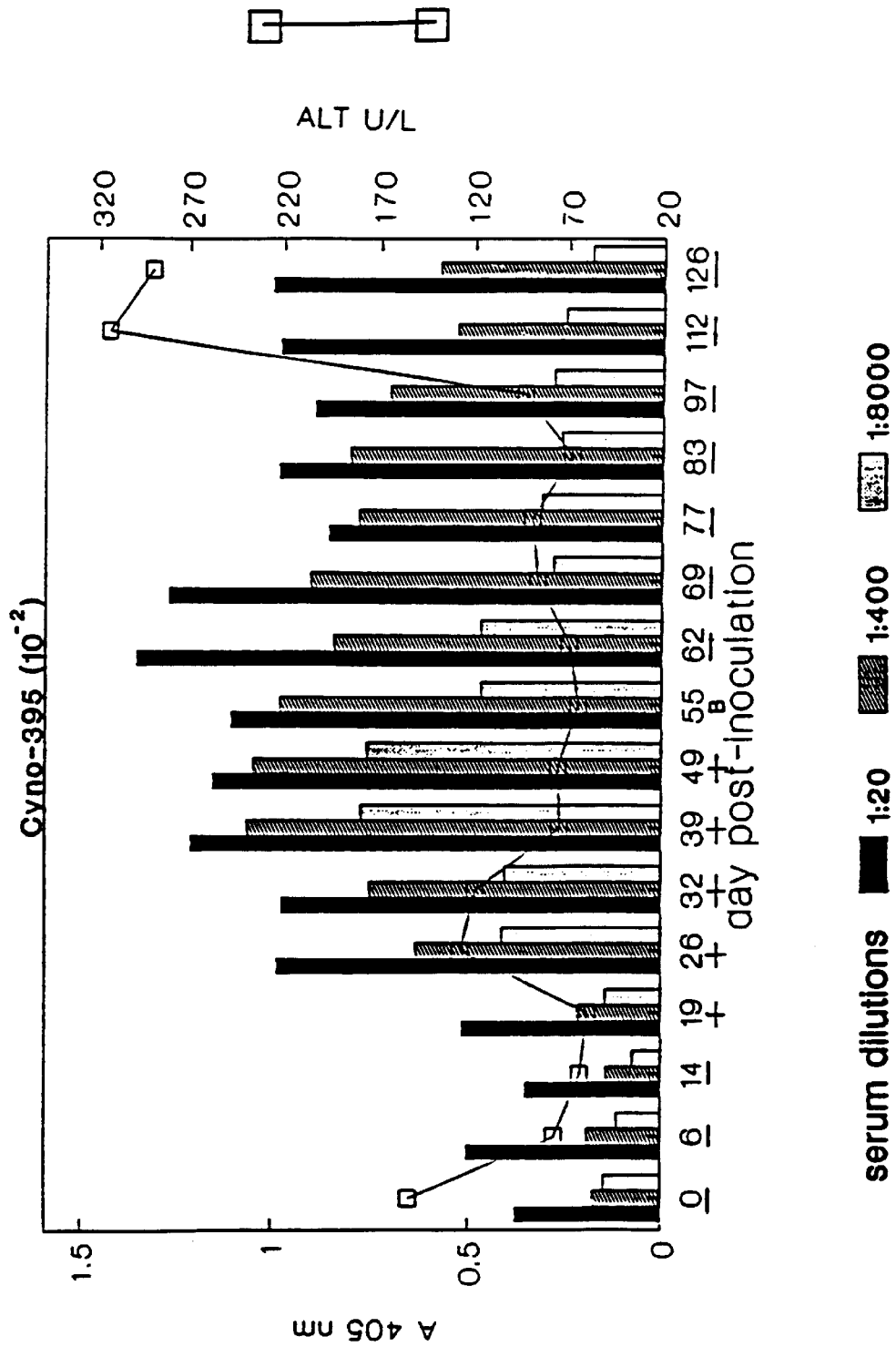
Figure 6D:
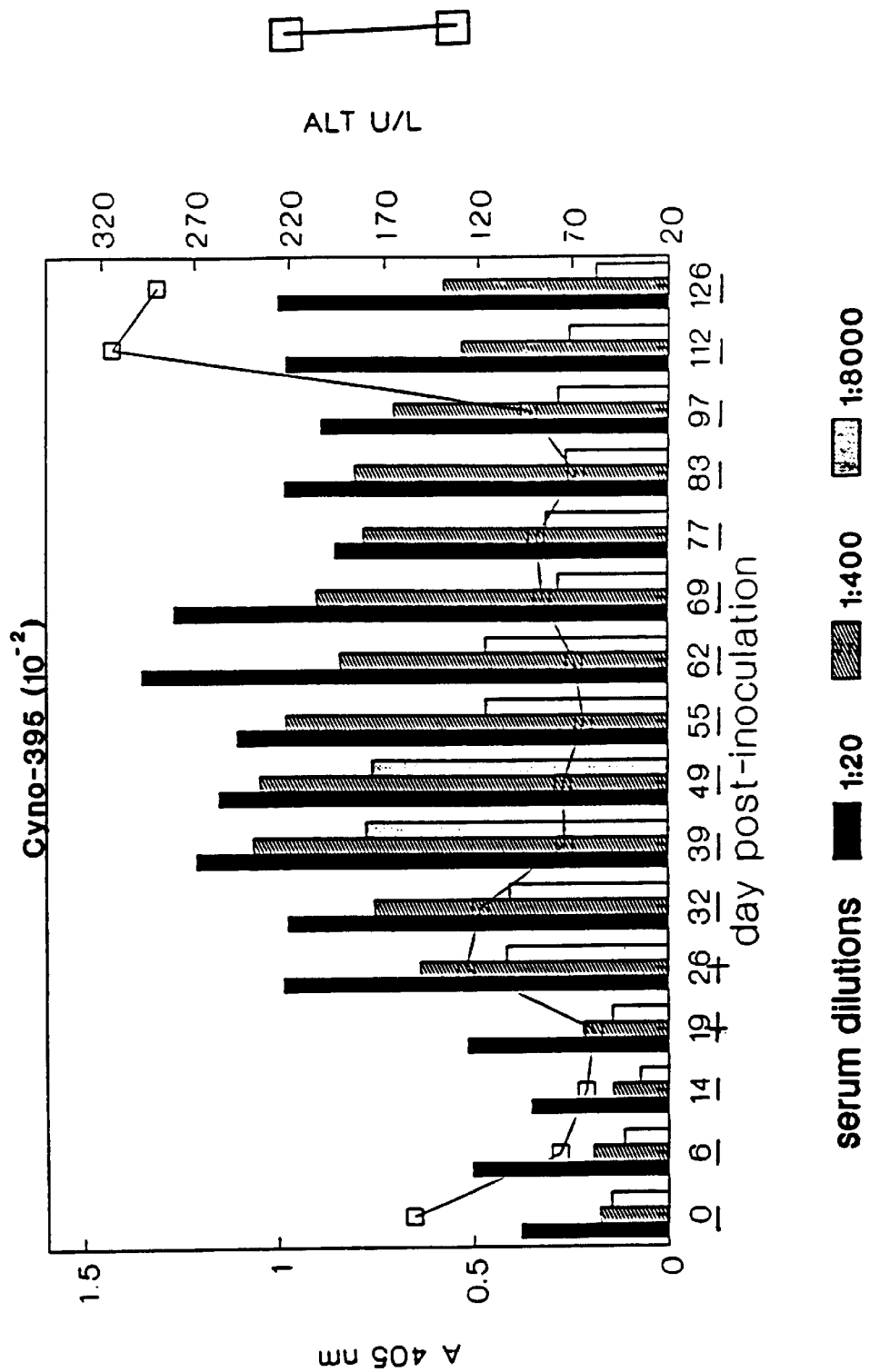
Figure 6E:
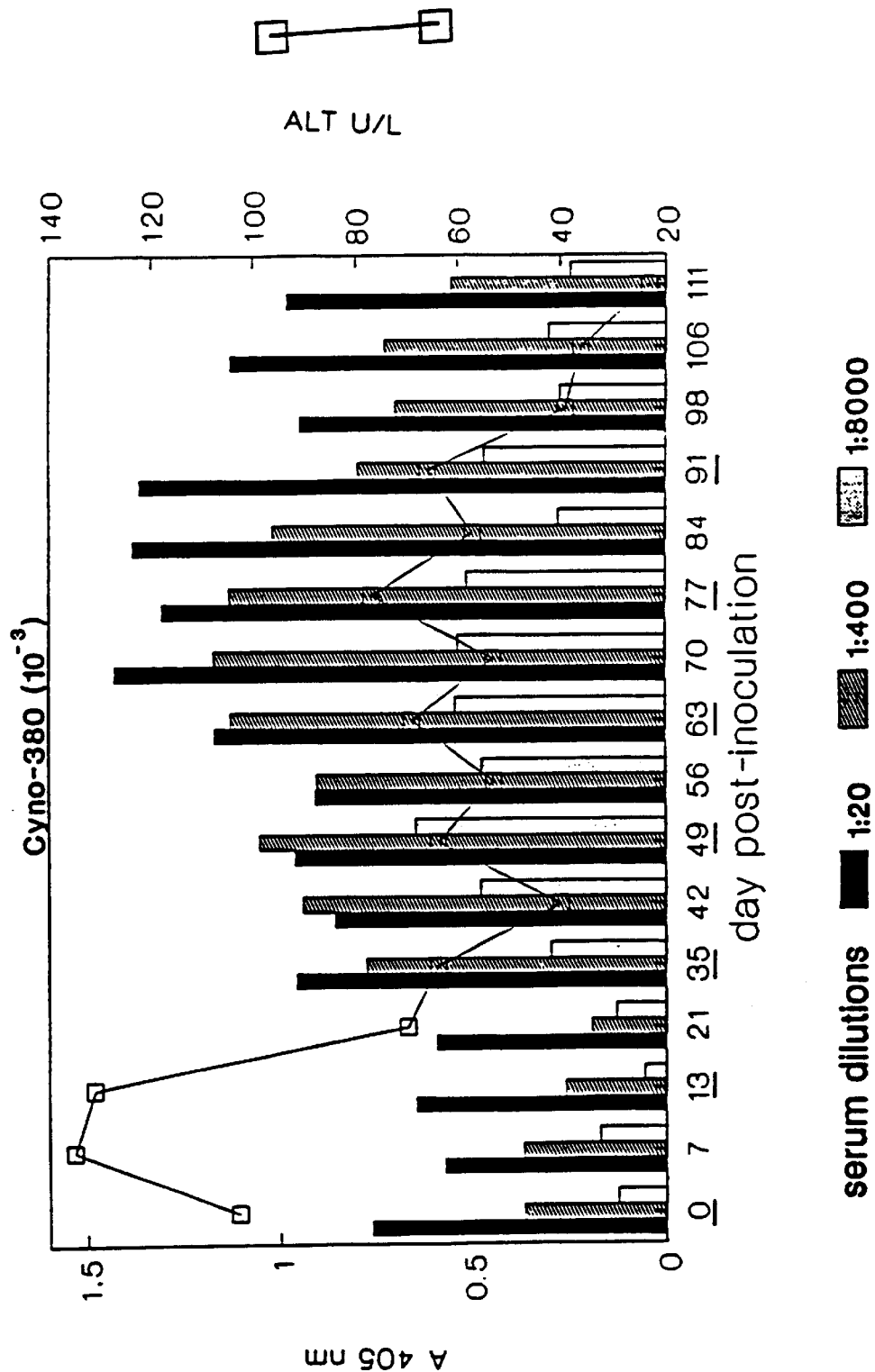
Figure 6F:
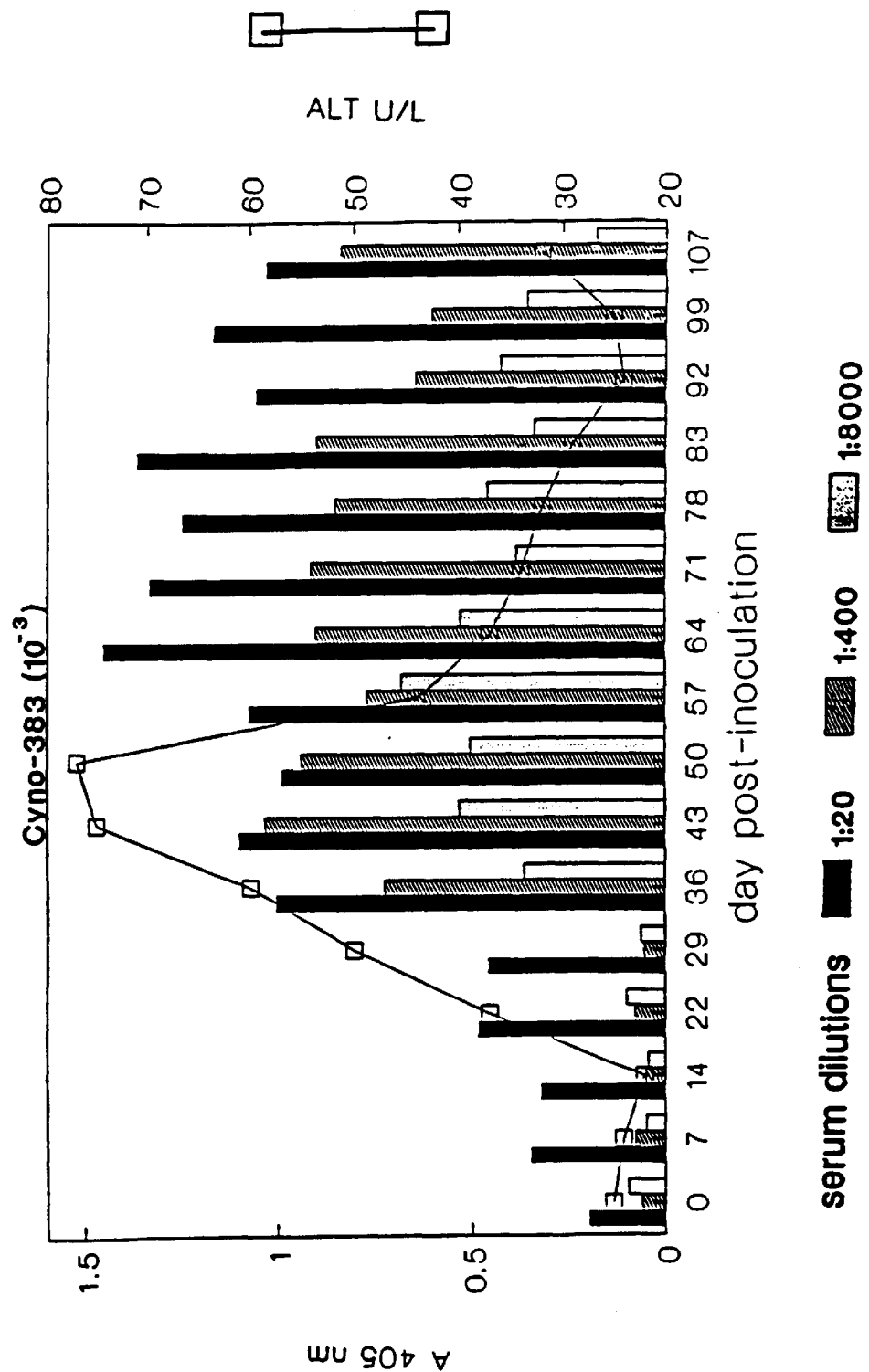
Figure 6G:
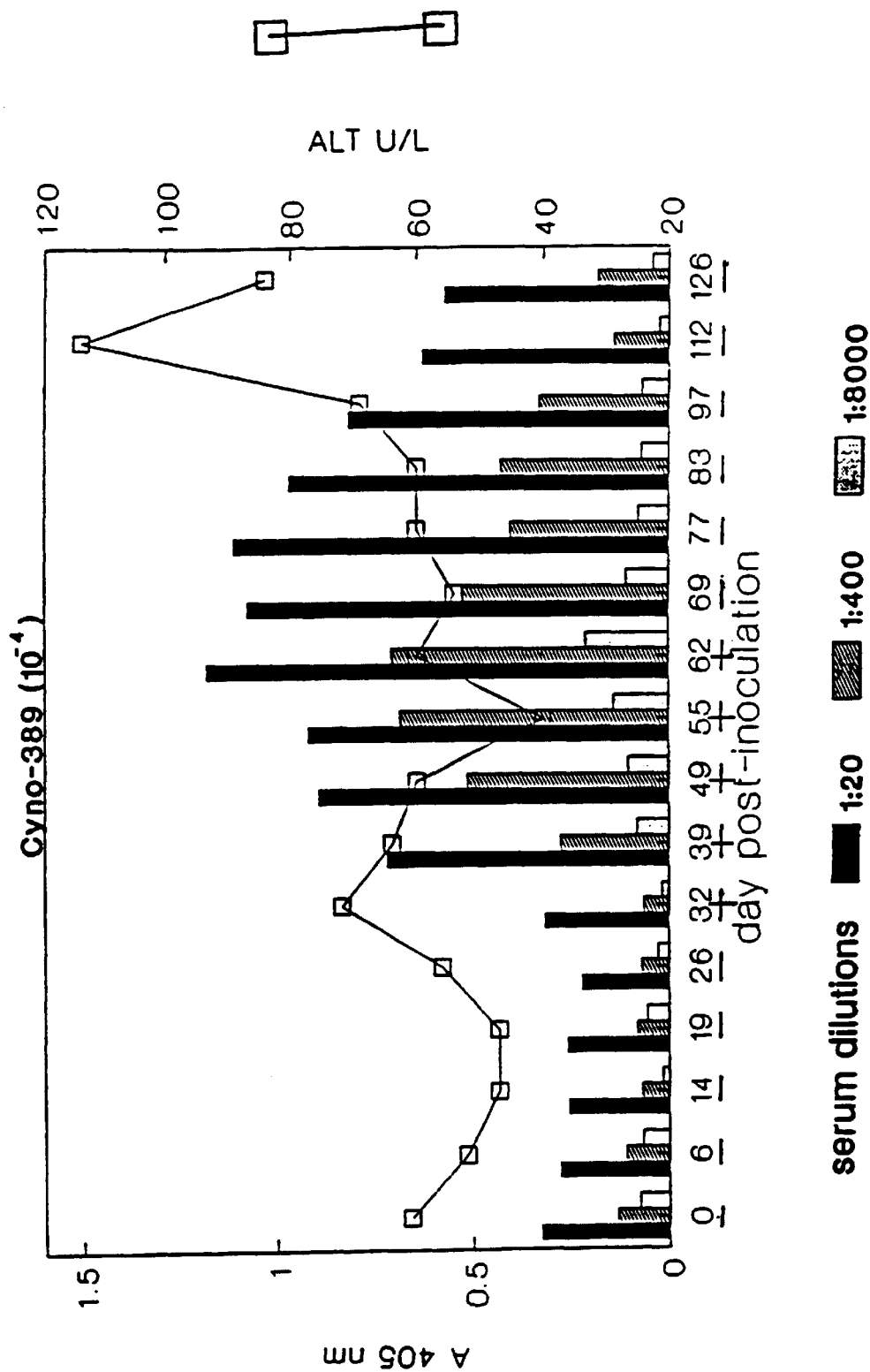
Figure 6I:
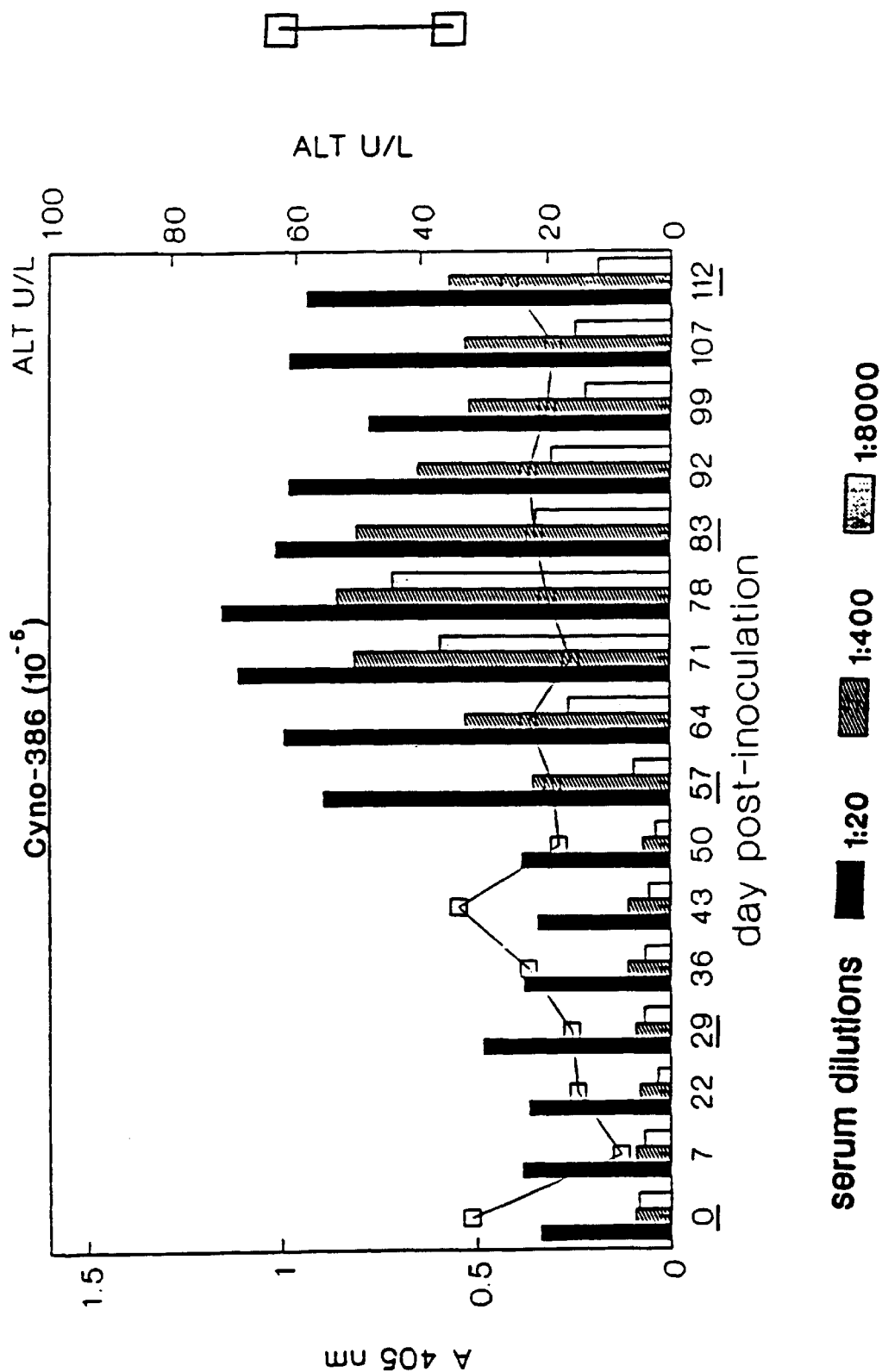
Figure 6J:
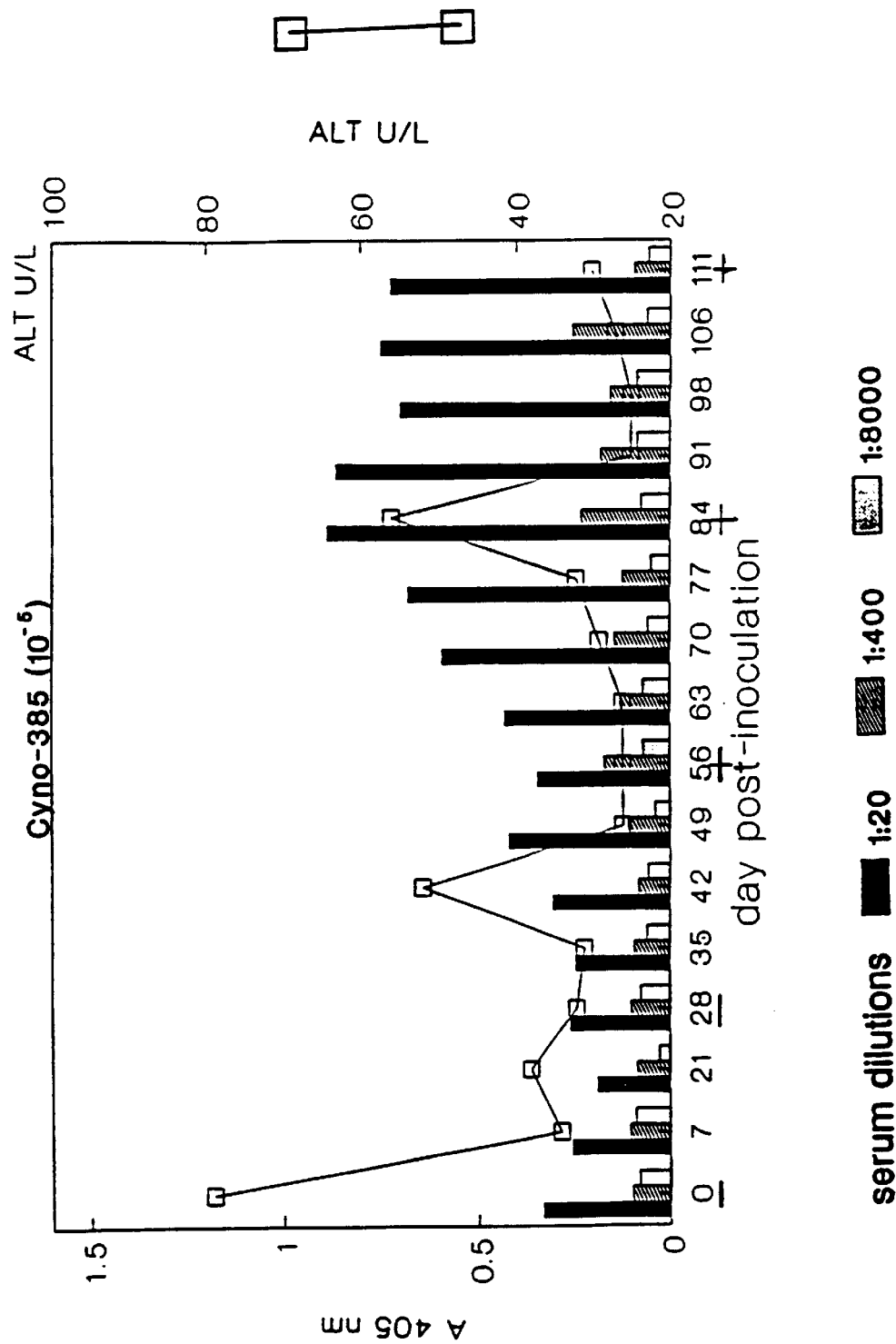

In both chimps, the serum ALT levels increased about 4 weeks post-inoculation (Table 2, FIG. 5). Both chimps seroconverted at the time of ALT enzyme elevation or earlier (FIG. 5A, 5C). Levels of IgM anti-HEV also were determined for the chimps. In chimp-1374, the titer of IgM anti-HEV (FIG. 5B) was not as high as the IgG titer (FIG. 5A) and waned over two weeks. Although both IgG and IgM antibodies were first detected for this animal on day 20, the titer of IgM anti-HEV was the highest while the titer of IgG was the lowest on that day, but then rose and stayed approximately at the same level for more than three months. In chimp-1375, only IgM anti-HEV was detected on day 20 (FIG. 5D). The titer was higher than in chimp-1374 and IgM anti-HEV was detected during the entire period of monitoring. IgG anti-HEV was first observed in this animal on day 27 (FIG. 5C) and remained at approximately the same level throughout the experiment.

EXAMPLE 9

Comparison of ELISA Based on Complete ORF-2 Protein Expressed in Insect Cells with that Based on Fragments of Structural Proteins Expressed in E. coli To estimate if expression of the complete ORF-2 region of the HEV genome in eukaryotic cells had any advantage over expression of fragments of structural proteins in E. coli, we used the former antigen in ELISA to retest cynomolgus monkey sera that had been analyzed earlier (Tsarev, S. A. et al. (1992), Proc. Natl. Acad. Sci USA, 99:559–563; and Tsarev, S. A. et al. (1993) J. Infect. Dis. (167:1302–1306)), using the antigen fragments expressed in bacteria (Table 3).

TABLE 3

Comparison of ELISA based on antigen from insect cells expressing complete ORF-2 with that based on antigen from E.coli expressing fragments of structural proteins

| | antigen derived from bacterial cells (Portion of ORF-2)[a] | antigen derived from insect cells (Complete ORF-2) anti-HEV | | |
|---|---|---|---|---|
| Cyno # | day anti-HEV first detected | first detected day | max. titer | titer |
| Cyno-376 | 28 | 21 | 1:400 | 1:8000 |
| Cyno-369 | 54 | 40 | 1:100 | 1:8000 |
| Cyno-374 | 19 | 19 | 1:400 | 1:8000 |

TABLE 3-continued

Comparison of ELISA based on antigen from insect cells expressing complete ORF-2 with that based on antigen from E.coli expressing fragments of structural proteins

| | antigen derived from bacterial cells (Portion of ORF-2)[a] | antigen derived from insect cells (Complete ORF-2) anti-HEV | | |
|---|---|---|---|---|
| Cyno # | day anti-HEV first detected | first detected day | max. titer | titer |
| Cyno-375 | 26 | 26 | 1:400 | 1:8000 |
| Cyno-379 | 21 | 19 | 1:100 | 1:6000 |
| Cyno-381 | 28 | 28 | 1:400 | 1:8000 |

[a]The sera were also tested with less sensitive ORF-3 antigen [..].
Tsarev, S. A. et al. (1993), J. Infect. Dis. (167:1302–1306)

For 3 of the 6 monkeys examined by ELISA, the antigen expressed in insect cells detected seroconversion earlier than the antigen expressed in E. coli. Using the insect cell-derived antigen, we were able to detect anti-HEV antibody in sera from all six monkeys at the highest dilution tested (1:8000). With E. coli-cell derived antigen (Burma Strain) no information about anti-HEV titers were obtained, since all sera were tested only at a dilution of 1:100 (Tsarev, S A et al (1992) Proc. Nat. Acad. Sci. USA; 89:559–563; Tsarev et al. (1993) J. Infect. Dis. (167:1302–1306)).

In another study, hepatitis E virus, strain SAR-55 was serially diluted in 10-fold increments and the $10^{-1}$ through $10^{-5}$ dilutions were inoculated into pairs of cyno-molgus monkeys to titer the virus. The serum ALT levels were measured to determine hepatitis and serum antibody to HEV was determined by the ELISA method of the present invention (data in figures) or by Genelab's ELISA (three ELISAS, each based on one of the antigens designated 4-2, 3-2 and 612 in Yarbrough et al. (*J. Virol*., (1991) 65:5790–5797) (data shown as positive (+) or negative (−) test at bottom of FIGS. 6*a*–*g*). All samples were tested under code.

The ELISA method of the present invention detected seroconversion to IgG anti-HEV in all cynos inoculated and all dilutions of virus.

In contrast, Genelab's results were strikingly variable, as summarized below.

TABLE 4

| Dilution of Virus | Genelab's ELISA | ELISA of Present Invention |
|---|---|---|
| $10^{-1}$ | did not test | positive |
| $10^{-2}$ | positive for both animals, limited duration | positive |
| $10^{-3}$ | negative for both animals | positive |
| $10^{-4}$ | Cyno 389: positive for IgM and IgG | positive |
| | Cyno 383: negative | positive |
| $10^{-5}$ | Cyno 366: negative | positive |
| | Cyno 385: positive | positive |

Since Cyno 385 ($10^{-5}$) was positive in ELISA tests both by Genelabs and the present invention, the $10^{-4}$ (ten times more virus inoculated) and $10^{-3}$ (100 times more virus inoculated) would also have been expected to be positive. The present invention scored them as positive in contrast to Genelab's ELISA test which missed both positives at $10^{-3}$ and one at $10^{-4}$ even though the ALT levels of Cyno 383 and 393 suggested active hepatitis. Therefore, the data support the advantages of the present ELISA method over the prior art methods of detecting antibodies to HEV.

EXAMPLE 10

Comparison of ELISAs Based on Recombinant ORF-2 Antigens Consisting of Either a 55 kDa Protein Expressed from the Complete ORF-2 Region of the Pakistani SAR-55 Strain of HEV or of Shorter Regions of ORF-2 Expressed as Fusion Proteins in Bacteria As described in Example 3 and as shown in FIGS. 2A and 2B, a number of proteins of varying molecular weights are expressed in insect cells infected with the recombinant baculovirus containing the complete ORF-2. A protein with a molecular weight of approximately 55 kDa was partially purified from $5\times10^8$ SF-9 cells harvested seven days post-inoculation as follows: The infected cells were centrifuged, resuspended in 10 ml of 10 mM Tris-HCl (pH 8.0), 50 mM NaCl, containing 40 μg/ml of phenylmethylsulfonyl fluoride (Sigma, St. Louis, Mo.), sonicated to disrupt the cells and the lysate was centrifuged at 90,000×g at 4° C. for 30 min. The supernatant was loaded onto a DEAE-sepharose CL-6B (Pharmacia, Uppsala, Sweden) column equilibrated with 10 mM Tris-HCl (pH 8.0), 50 mM NaCl. The column was washed with loading buffer and the 55 kDa protein was eluted in 10 mM Tris-HCl (pH 8.0) 250 mM NaCl. Fractions containing the 55 kDa protein were combined and the protein was precipitated by addition of 3 g of $(NH_4)_2SO_4$ to 10 ml of the protein solution. The protein pellet was dissolved in 10 mM Tris-HCl (pH 8.0), 50 mM NaCl. The 55 kDa protein was then used as the insect cell-expressed HEV antigen in ELISA in comparison testing against ELISAs based on either one of two HEV antigens expressed in bacteria, (3-2 (Mexico) (Goldsmith et al., (1992) *Lancet*, 339:328–331) or SG3 (Burma) (Yarbough et al., (1993) Assay development of diagnostics tests for hepatitis E. In "International Symposium on Viral Hepatitis and Liver Disease. Scientific program and abstract volume." Tokyo:VHFL, p 87, Abstract # 687). These bacterial antigens were fusion proteins of the 26 kDa glutathione-S-transferase (GST) and either the antigenic sequence 3-2 (M) consisting of 42 amino acids located 6 amino acids upstream of the C-terminus of ORF-2 (Yarbough et al., (1991) *J. Virol*., 65:5790–5797) or the 327 C-terminal amino acids of ORF-2 (Yarbough et al., (1993)). The ELISAs were carried out as follows.

Sixty ng per well of the 55 kDa protein or 200 ng per well of the fusion antigens in carbonate buffer (pH 9.6) were incubated in wells of a polystyrene microtiter assay plate (Dynateck, S. Windham, Me.) for 2 h at 37° C. Plates were blocked with PBS containing 10% fetal calf serum and 0.5% gelatin. Serum samples from cynomolgus monkeys inoculated intravenously (note: cynos 387 and 392 were inoculated orally) with a dilution of feces containing the SAR-55 strain of HEV ranging from $10^{-1}$ through $10^{-8}$ as indicated in Table 5 and FIGS. 7A–7J and 8A–8D were diluted 1:100 in blocking solution. Peroxidase-conjugated goat anti-human IgM (Zymed, San Francisco, Calif.) diluted 1:1000 or 1:2000, or peroxidase-labelled goat anti-human immunoglobulin diluted 1:1000 was used as the detector antibody.

In all of the ELISA tests except those for the two orally inoculated monkeys, cyno-387 and cyno-392, the 55 kDa and the fusion antigens were tested concurrently in the same laboratory so that the only variable was the antigen used. Criteria for scoring positive reactions in anti-HEV ELISA with the 55 kDa antigen were an optical density value $\geq 0.2$ and greater than twice that of a pre-inoculation serum sample for the same animal. In addition, since both antigens expressed in bacteria were fusion proteins with GST, the optical density of a sample tested with these antigens had to be 3 times higher than that obtained with non-fused GST in order to be considered positive (Goldsmith et al., (1992)).

Results

Figure 7A:
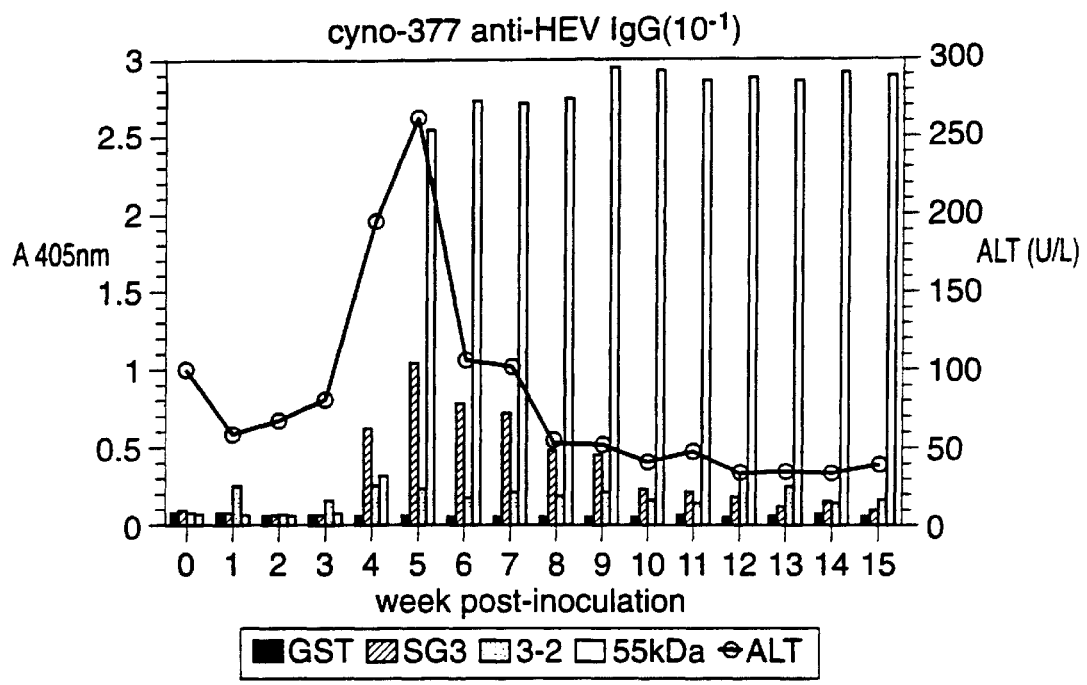
FIGS. 7A–J show anti-HEV IgG ELISA and alanine aminotransferase (ALT) values for cynomolgus monkeys inoculated with ten-fold serial dilutions (indicated in parenthesis at the top of each panel) of a 10% fecal suspension of SAR-55 HEV. Recombinant antigens used in ELISA were: glutathione-S-transferase (GST); 3-2(M), a fusion of the 3-2 epitope [Yarbough et al., (1991) *J. Virol*, 65:5790–5797] and GST; SG3 (B), a fusion of 327 C-terminal amino acids of ORF-2 and GST [Yarbough et al., (1993): Assay Development of diagnostic tests for Hepatitis E in "International Symposium on Viral Hepatitis and Liver Disease. Scientific Program and Abstract Volume." Tokyo:VHFL p. 87]; and a 55 kDa ORF-2 product directly expressed in insect cells.
Figure 7B:
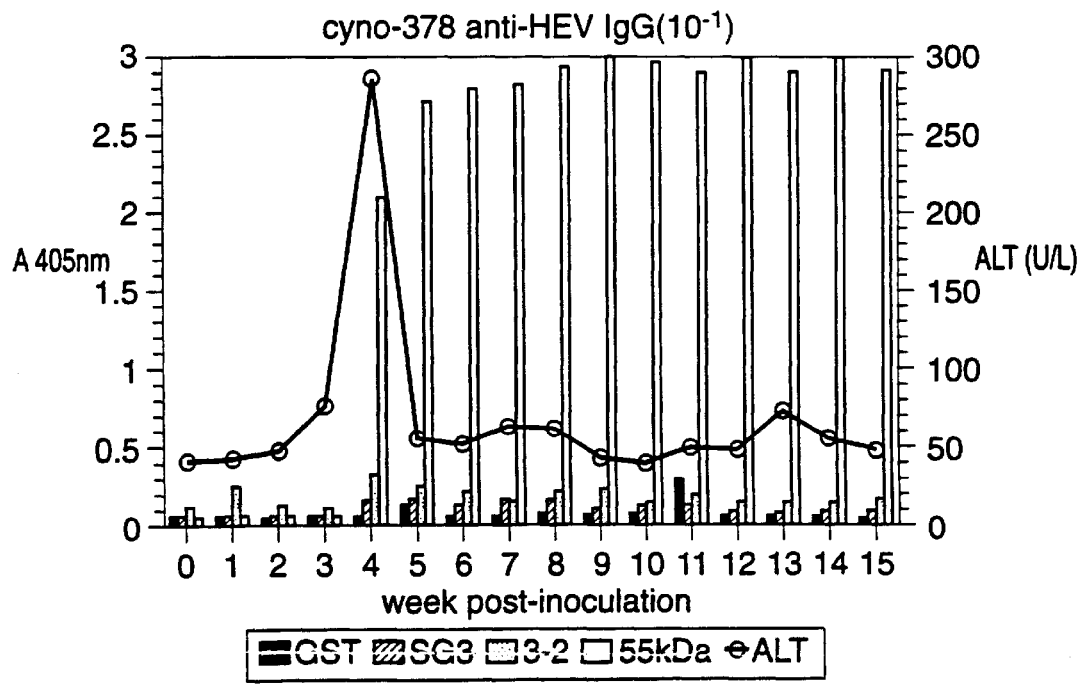

Both cynomolgus monkeys (377, 378) inoculated with the $10^{-1}$ dilution of the standard HEV fecal suspension had a pronounced increase in ALT activity at 4–5 weeks post-inoculation, indicative of hepatitis (Table 5, FIGS. 7A and 7B).

positive signal reached a maximum shortly after seroconversion and remained at approximately the same high level throughout the experiment (15 weeks).

Figure 7C:
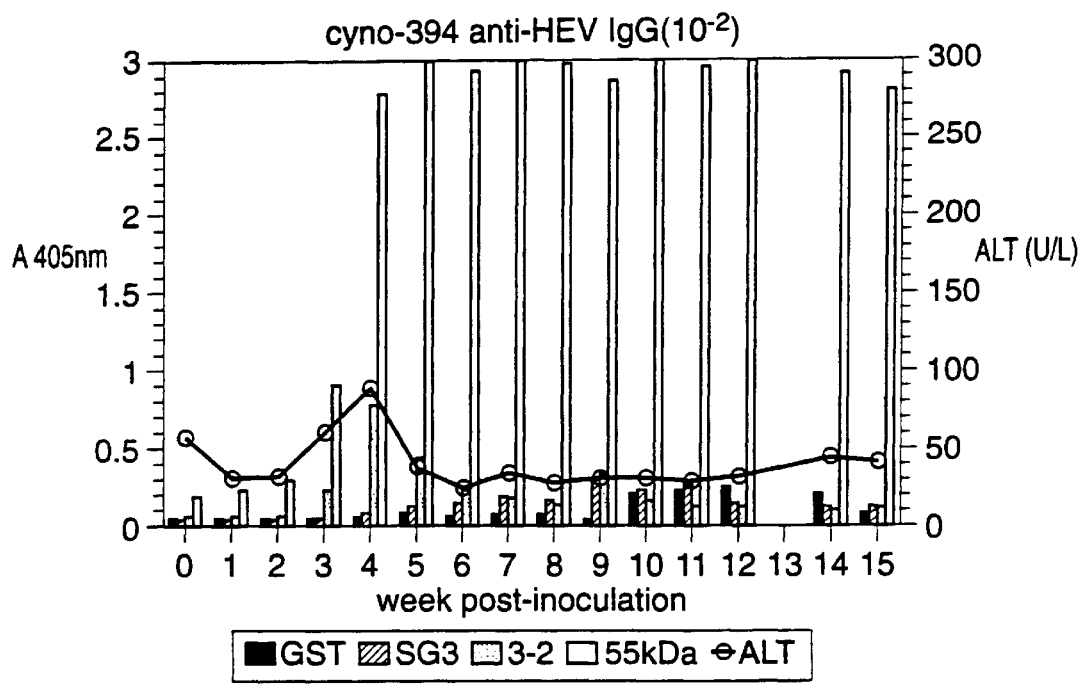
Figure 7D:
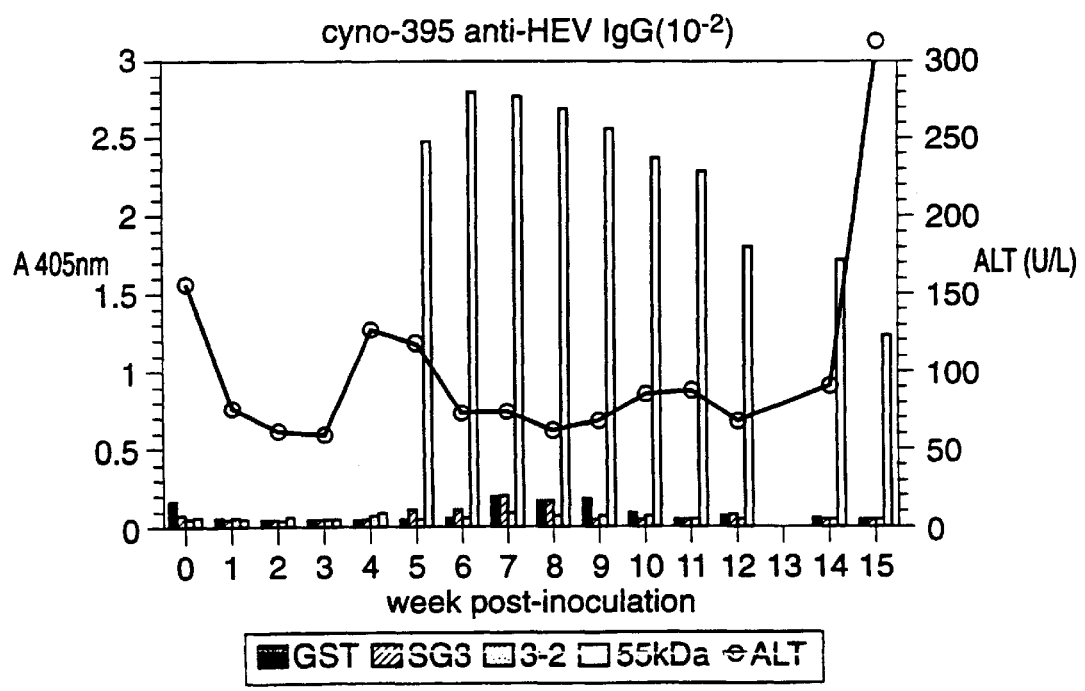
Figure 8A:
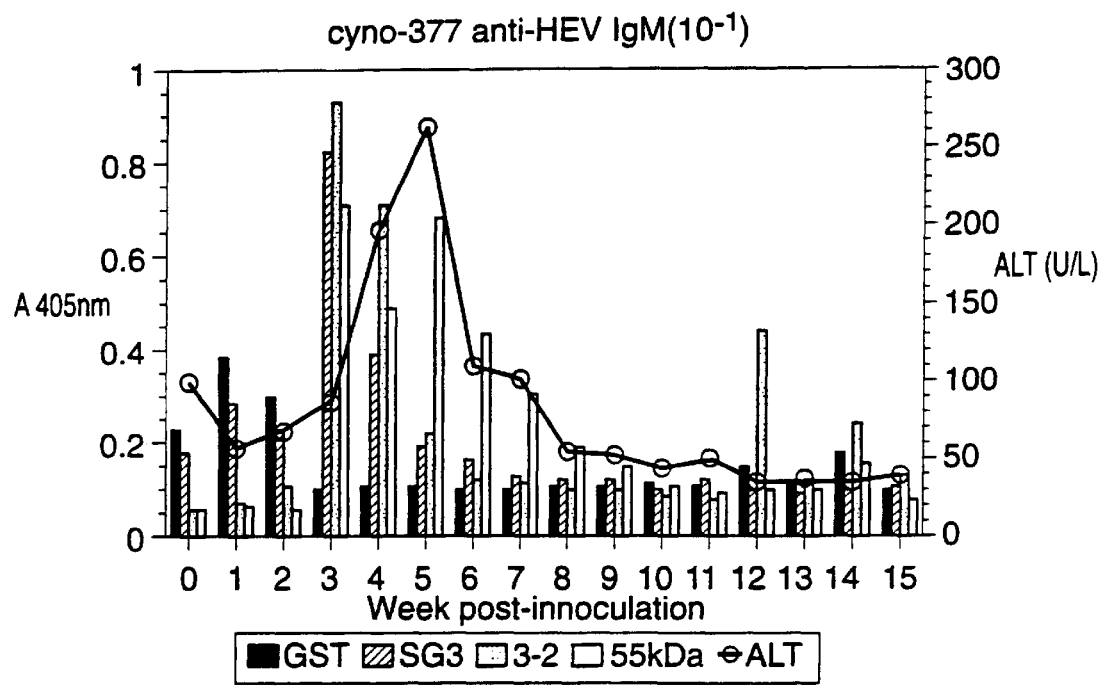
Figure 8B:
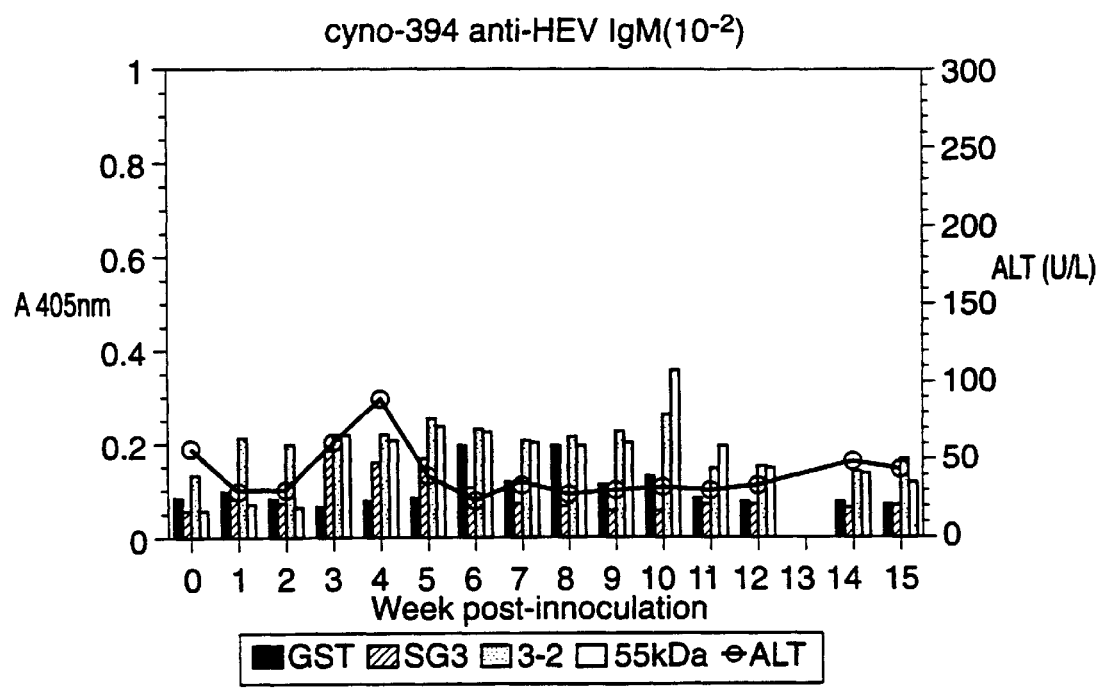

Elevation in ALT activities in both monkeys (394 and 395) inoculated with a $10^{-2}$ dilution of the standard HEV stool suspension was significantly less pronounced at the expected time of hepatitis than in animals inoculated with the ten-fold higher dose ( Table 5, FIGS. 7C and 7D). Cyno-395 actually had higher ALT activities prior to inoculation as well as at 15 weeks post-inoculation. The latter was probably not related to HEV infection. Weakly positive IgM anti-HEV was detected only in cyno-394 (FIG. 8B) and only with ELISA based on the 55 kDa antigen. Both animals were infected, however, since IgG anti-HEV seroconversion was detected in both animals. In cyno-394, anti-HEV IgG was

TABLE 5

Summary of biochemical and serological events occurring in cynomolgus monkeys after inoculation with $10^{-1}$ to $10^{-8}$ dilutions of the standard stock of the SAR-55 HEV inoculum.

| Cyno | Dilution of viral stock inoculum | ALT pre-inoculation mean (SD)¶ | ALT peak week | ALT peak value (U/L) | weeks post-inoculation anti-HEV peak was detected with 55 kDa antigen IgG | weeks post-inoculation anti-HEV peak was detected with 55 kDa antigen IgM | weeks post-inoculation anti-HEV was detected with fusion antigen IgG SG3 | weeks post-inoculation anti-HEV was detected with fusion antigen IgG 3-2(M) | weeks post-inoculation anti-HEV was detected with fusion antigen IgM SG3 | weeks post-inoculation anti-HEV was detected with fusion antigen IgM 3-2(M) |
|---|---|---|---|---|---|---|---|---|---|---|
| 377 | $10^{-1}$ | 76 (39) | 5 | 264 | 4–15† | 3–7 | 4–10 | 4–5 | 3–4 | 3–5 |
| 378 | $10^{-1}$ | 50 (9) | 4 | 285 | 4–15 | — | — | — | — | — |
| 394 | $10^{-2}$ | 62 (14) | 4 | 89 | 3–15 | 3–10 | — | 4–6 | — | — |
| 395 | $10^{-2}$ | 121 (21) | 15 | 314 | 5–15 | — | — | — | — | — |
| 380 | $10^{-3}$ | 89 (20) | 1 | 135 | 5–15* | — | 6–15 | — | — | — |
| 383 | $10^{-3}$ | 29 (8) | 4 | 77 | 5–15 | 5–13 | — | — | — | — |
| 389 | $10^{-4}$ | 60 (7) | 15 | 114 | 6–15 | 6–8 | — | — | — | — |
| 393 | $10^{-4}$ | 41 (4) | 5 | 87 | 6–15 | — | — | — | — | — |
| 385 | $10^{-5}$ | 59 (32) | 7 | 56 | 11–15 | — | — | 7–15 | — | — |
| 386 | $10^{-5}$ | 31 (4) | 4 | 34 | 8–15 | 8–13 | — | — | — | — |
| 397 | $10^{-6}$ | 60 (4) | 8 | 94 | — | — | — | — | — | — |
| 398 | $10^{-6}$ | 36 (3) | 2 | 55 | — | — | — | — | — | — |
| 399 | $10^{-7}$ | 102 (16) | 2 | 93 | — | — | — | — | — | — |
| 400 | $10^{-7}$ | 57 (4) | 9 | 188 | — | — | — | — | — | — |
| 403 | $10^{-8}$ | 33 (3) | 2–3 | 49 | — | — | — | — | — | — |
| 406 | $10^{-8}$ | 56 (4) | 2 | 73 | — | — | — | — | — | — |
| 387 | $10^{-1}$ (oral)§ | 32 (4) | 4 | 38 | — | — | ND | — | ND | — |
| 392 | $10^{-1}$ (oral)§ | 49 (6) | 3 | 70 | — | — | ND | — | ND | — |

¶ALT mean and standard deviation (SD) values of pre-inoculation sera.
†The experiment was terminated after 15 weeks.
*The OD values of pre-inoculation sera of Cyno-380, when tested by ELISA with 55 kDa antigen, were twice as high as the mean value of pre-inoculation sera for other cynomolgus monkeys.
§All ELISA tests except for Cyno-387 and Cyno-392 were performed in the same experiments.
—not detected.
ND not done.

All 3 antigens tested detected IgM anti-HEV in samples taken from cyno-377 3 weeks post-inoculation ( Table 5, FIG. 8A), but IgM anti-HEV was not detected in any samples from the second animal, cyno-378. IgG anti-HEV was detected in both animals with the 55 kda-based ELISA, but only in cyno-377 with the ELISA based on fusion antigens. Values of OD for IgG anti-HEV were significantly higher than those for IgM anti-HEV. ELISA values obtained with the 55 kDa antigen were also significantly higher than those obtained with either of the two fusion antigens (FIGS. 7A and 7B). The patterns of the OD values observed in ELISA with antigens from the two sources also differed significantly. In the case of ELISA based on the fusion antigens, positive signals reached a maximum shortly after seroconversion and then waned during the 15 weeks of the experiment. In ELISA based on the 55 kDa antigen, the first detected by the 55 kDa antigen at week 3 and one week later with the 3-2(M) antigen. The SG3 (B) antigen did not detect seroconversion in cyno-395 and anti-HEV IgG was detected only with the 55 kDa antigen. Anti-HEV tended to diminish in titer with time in this animal.

Figure 7E:
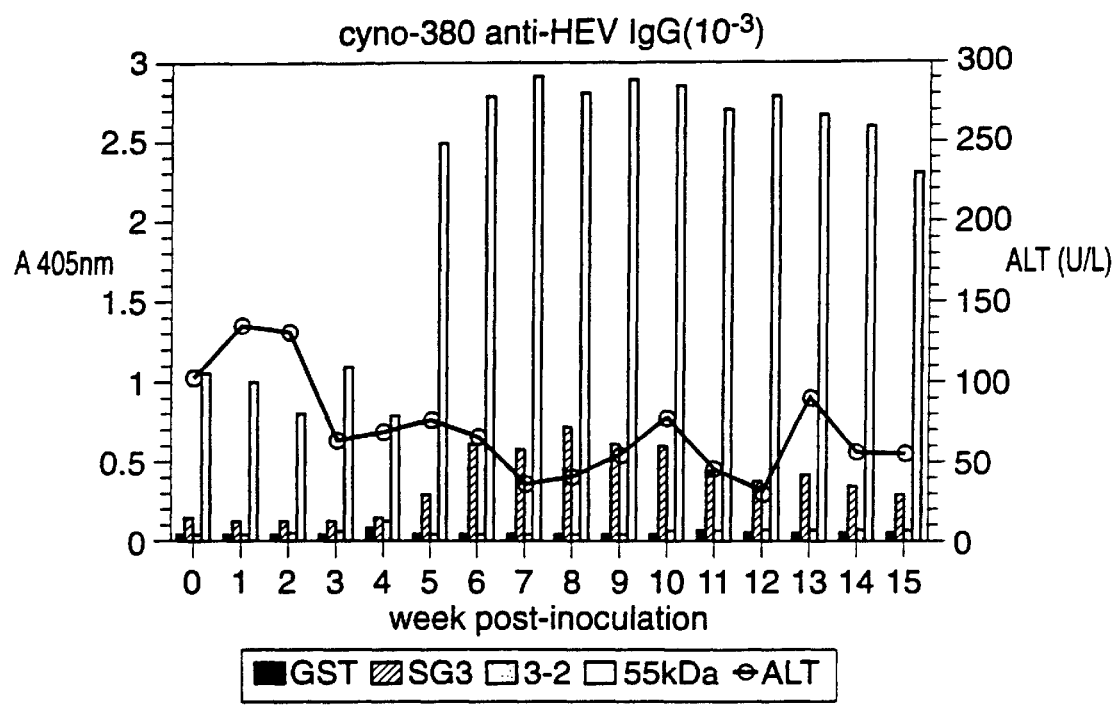
Figure 7F:
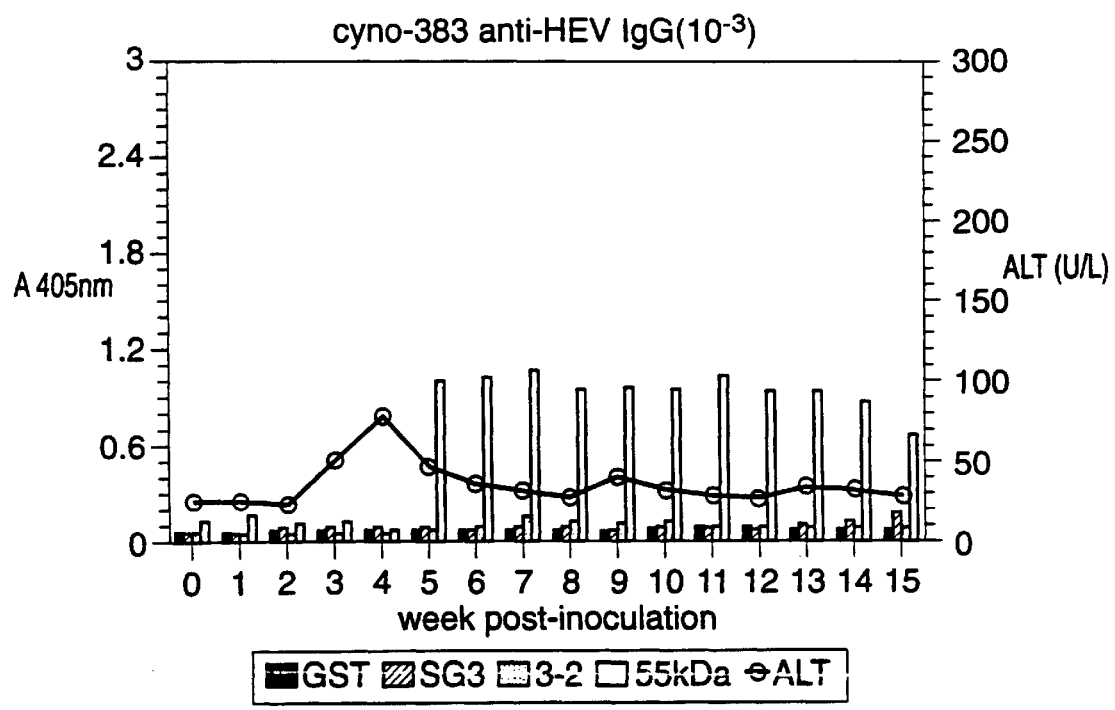
Figure 8C:
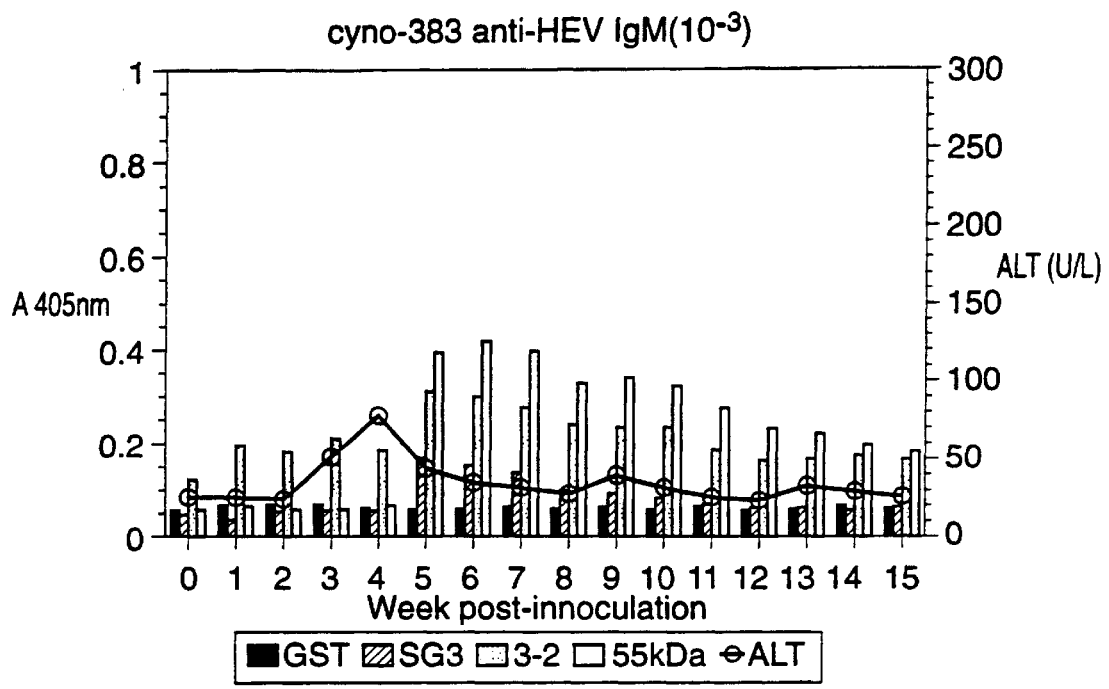

Cyno-380 and cyno-383 were inoculated with a $10^{-3}$ dilution of the standard HEV fecal suspension (Table 5, FIGS. 7E 7F, 8C). Cyno-380 had fluctuating ALT activities before and after inoculation; therefore, ALT levels could not be used to document hepatitis E in this animal. In Cyno-383, a slight rise of ALT activities was observed (FIG. 7F), which was coincident with seroconversion and, therefore, might be due to mild hepatitis E. IgM Anti-HEV was not detected in sera from cyno-380 with any of the three antigens. Cyno-380 seroconverted for IgG anti-HEV when tested by ELISA with SG3 (B) but not with 3-2(M) antigen. This animal had preexisting IgG anti-HEV when tested with the 55 kDa antigen, but there was a large increase in IgG anti-HEV starting at week 5 (FIG. 7E). Identification of preexisting antibody was reported earlier in sera from another cynomolgus monkey [Ticehurst et al., (1992) *J. Infect Dis.*, 165:835–845; Tsarev et al., (1993) *J. Infect. Dis.*, 168:369–378]. Seroconversion occured at the expected time but the levels of IgG anti-HEV in samples from cyno-383 remained low and detectable only with the 55 kDa antigen.

Figure 7G:
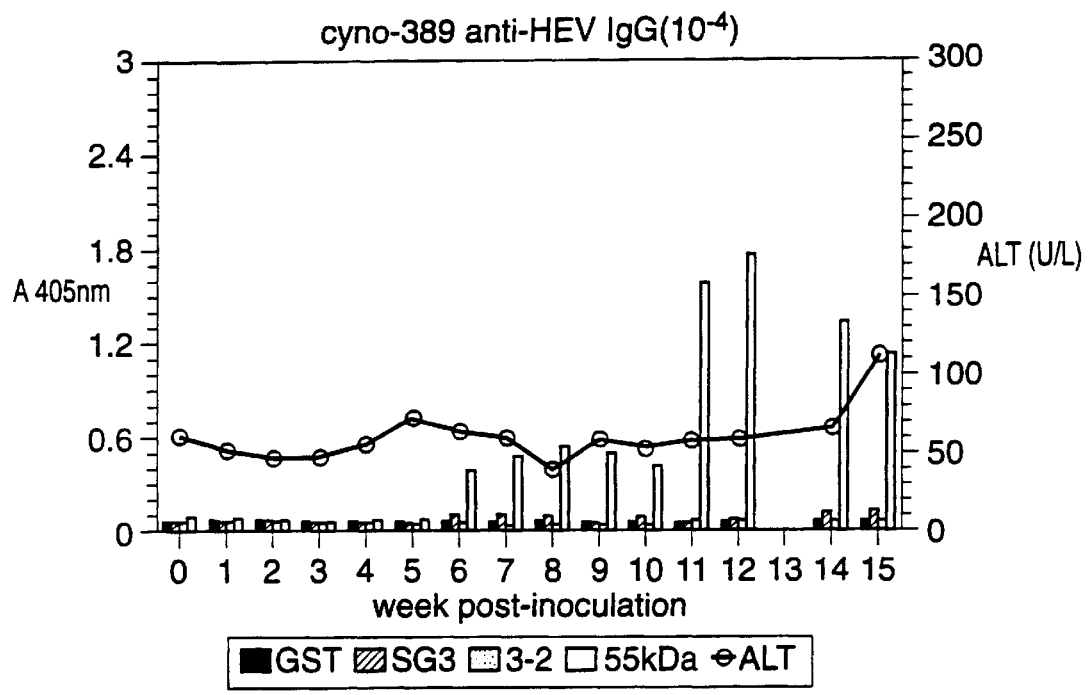
Figure 7H:
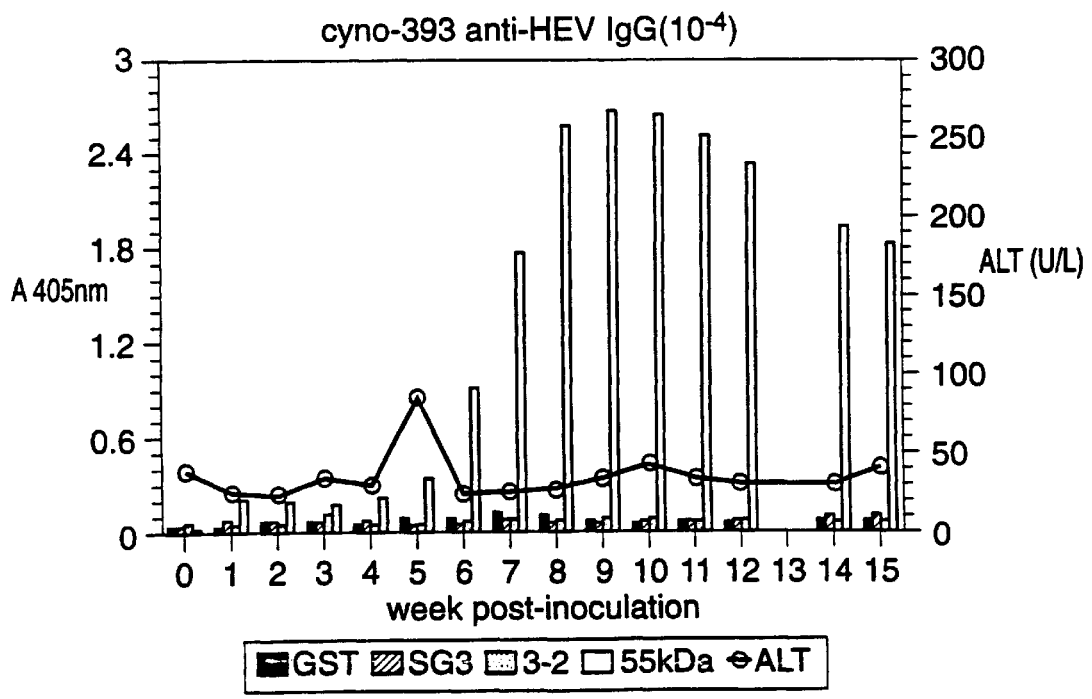
Figure 8D:
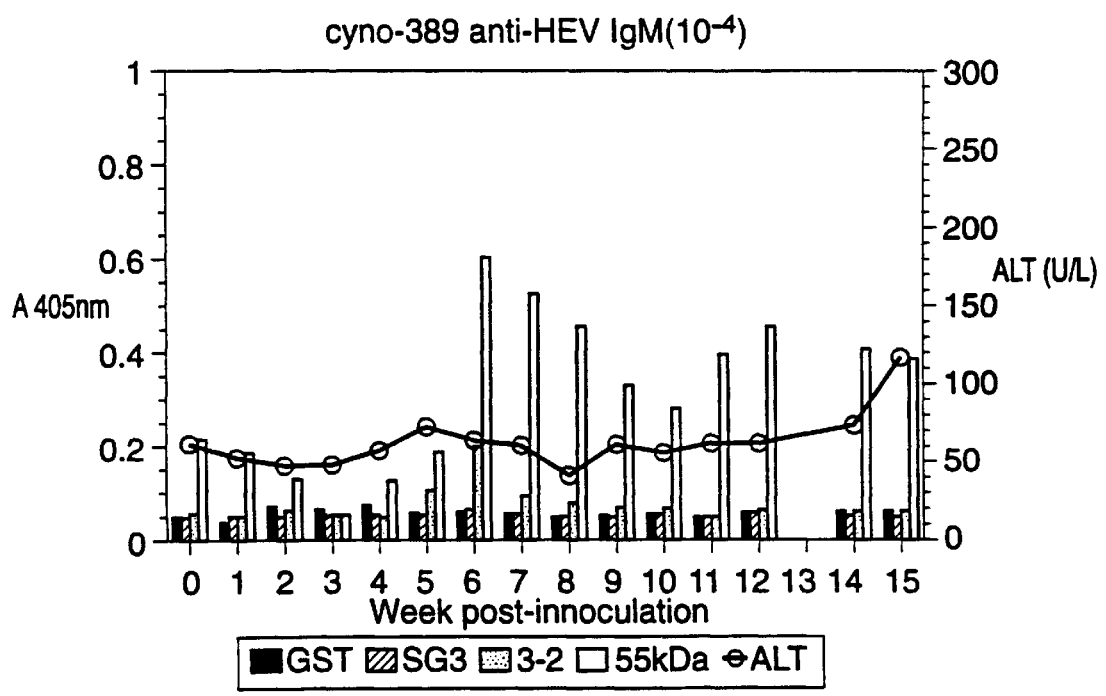

Cyno-389 and cyno-393 were inoculated with a $10^{-4}$ dilution of the standard HEV fecal suspension (FIGS. 7G, 7H, 8D, Table 5). Neither animal had a significant rise in ALT activities, although the timing of a small but distinct ALT peak in sera of cyno-393 at week 5 (FIG. 7H) suggested borderline hepatitis. ELISA based on the SG3 (B) or 3-2(M) antigens scored both animals as negative for HEV infection. In contrast, the 55 kDa antigen detected IgM anti-HEV in sera of cyno-389 at weeks 6–8 post-inoculation (FIG. 8D) and IgG anti-HEV from week 6 through week 15 in both animals.

Figure 7I:
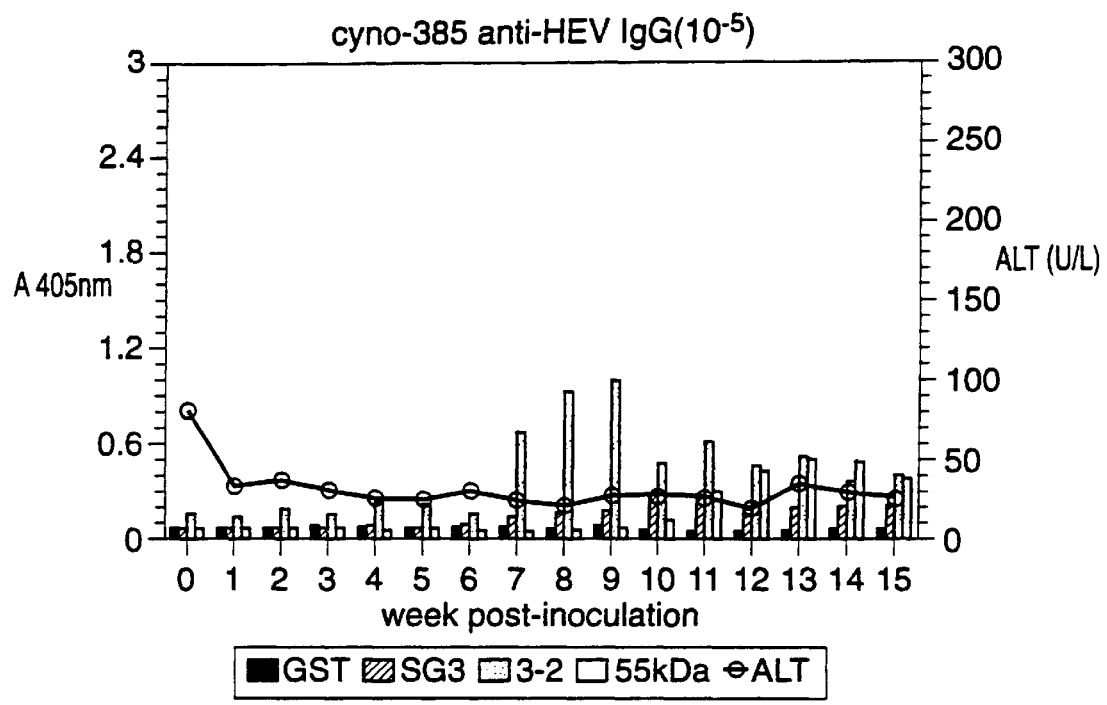
Figure 7J:
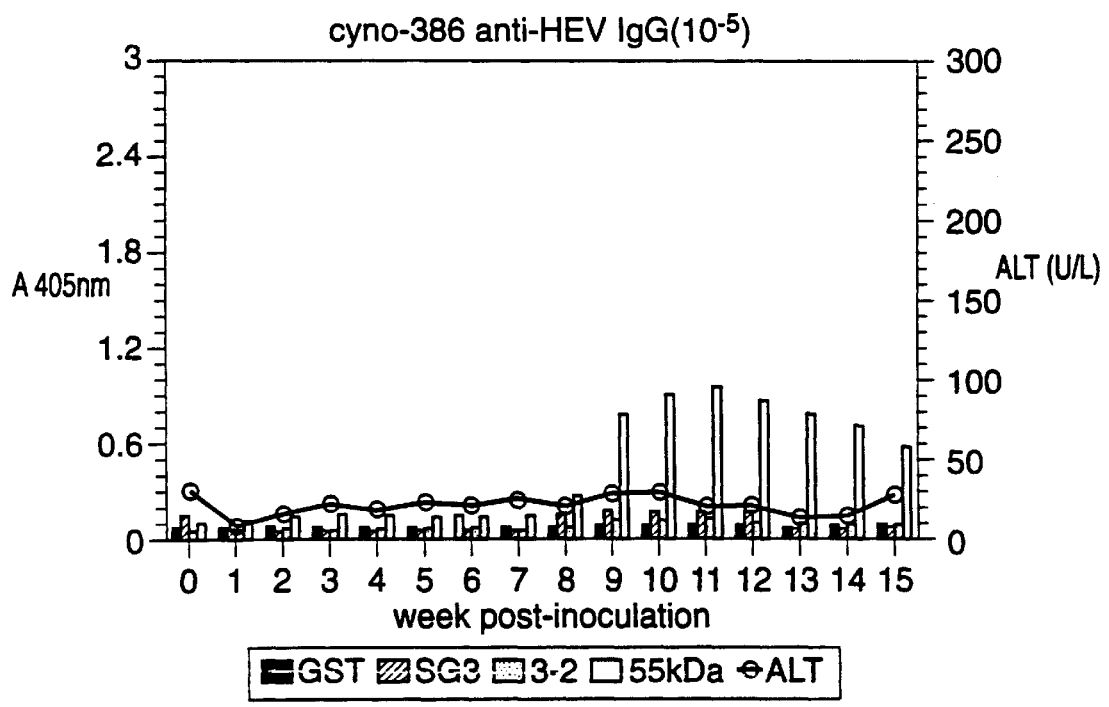

Neither animal inoculated with the $10^{-5}$ dilution of the standard fecal suspension developed a noticeable rise in ALT activities (FIG. 7I, 7J, Table 5), but, in cyno-386, IgM and IgG anti-HEV were detected at weeks 8–13 and 8–15 respectively with the 55 kDa antigen (FIG. 7J, 8E). Cyno-385 anti-HEV IgG was detected with the 55 kDa and the 3-2(M) antigen but not with SG3 (B) antigen. In contrast to previous patterns, IgG anti-HEV was detected with a fusion antigen four weeks earlier and at higher levels than with the 55 kDa antigen.

None of the animals inoculated with dilutions of the standard HEV fecal suspension in the range of $10^{-6}$–$10^{-8}$ developed antibody to any of the three HEV antigens. Increased ALT activities were not observed in those animals, except for one rather prominent peak of ALT activity at week 9 in cyno-400 (Table 5). However, the absence of seroconversion in this animal indicated that this peak probably was not related to HEV infection.

With respect to the two cynomolgus monkeys (387 and 392) inoculated orally with the $10^{-1}$ dilution of the 10% fecal suspension, neither monkey was infected since ALT levels did not rise and ELISA performed with the 3-2(M) and 55 kDa antigens did not detect seroconversion to HEV (Table 5).

Finally, serological evidence for HEV infection was found in all animals inoculated with decimal dilutions of the fecal suspension through $10^{-5}$; none of the animals receiving higher dilutions had such evidence. Prominent hepatitis, as defined by elevated ALT, was observed only in the two monkeys infected with the $10^{-1}$ dilution. Significantly lower elevations of ALT activities were observed in some animals inoculated with higher dilutions of the fecal suspension while, in others, elevations were not found. Considered alone, these low ALT rises were not diagnostic of hepatitis. However, the coincidence of seroconversion and appearance of these ALT peaks suggests the presence of mild hepatitis in these animals. Anti-HEV IgG seroconversion was detected in all animals inoculated with dilutions of fecal suspension ranging from $10^{-1}$–$10^{-5}$. A tendency toward lower levels of IgG anti-HEV and delayed seroconversion was observed in animals inoculated with higher dilutions of the stock.

In sum, the 55 kDa Pakistani ORF-2 antigen was more efficient than either the 3-2(M) or SG3 (B) antigen for detecting IgM and IgG anti-HEV in cynomolgus monkeys infected with the Pakistani strain of HEV. For example, for all animal sera except those from cyno-385, detection of IgG or IgM anti-HEV by ELISA was more efficient with the 55 kDa antigen than with either the 3-2(M) or SG3 antigen. ELISA with the 55 kDa antigen produced internally consistent and reproducible results, detecting IgG anti-HEV in all ten animals inoculated with a fecal dilution of $10^{-5}$ or lower. The magnitude of ELISA signals also decreased as the inoculum was diluted. The fusion antigens did not produce consistent results between the pairs of animals. Only one of each pair of animals inoculated with the $10^{-1}$, $10^{-2}$, $10^{-3}$, or $10^{-5}$ dilution showed seroconversion to IgG anti-HEV, and only a single seroconversion for IgM anti-HEV was detected with these antigens. Neither of the animals inoculated with the $10^{-4}$ dilution of the original inoculum seroconverted to either of the two fusion antigens even though sera from one animal (cyno-393) had sustained high levels of anti-HEV IgG when assayed with the 55 kDa antigen. Although, as discussed above, ELISA for IgM anti-HEV was significantly less sensitive than ELISA for cynomolgus IgG anti-HEV, the 55 kDa antigen was able to detect anti-HEV IgM in more animals than the 3-2(M) or SG3 (B) antigen. In sum, a definitive conclusion about the infectious titer of the Pakistani viral inoculum used in this study could not be made with the combined data from the 3-2(M) and SG3 (B) based ELISA but could be made with data obtained with the 55 kDa Pakistani ELISA alone.

With respect to cyno-385, the difference in anti-HEV IgG detection between the two test results was four weeks. These data suggest the presence of a distinct epitope in the 3-2(M) antigen recognized by this animal that is absent in the larger 55 kDa and SG3 (B) antigens. When total insect cell lysate, which contained both complete ORF-2 (75 kDa) and 55 kDa proteins, was used as antigen to retest these samples, the results were the same as when 55 kDa was used alone. This finding suggests that the 55 kDa protein may not lack 3-2 epitope amino acids but rather that the conformation of the 3-2 epitope sequence differed among all three antigens used in this study. Finally, it is interesting to note that despite the fact that antigen SG3 (B) contained a longer portion of ORF-2 and included the entire sequence of epitope 3-2, it did not detect more positive sera than the 3-2(M) antigen.

EXAMPLE 11

Determination of the Infectious Titer of the HEV SAR-55 Viral Stock BY RT-PCR

Knowledge of the infectious titer of inocula is critical for interpretation of much of the data obtained in experimental infections of animal models. However, until now the infectious titer of an HEV viral stock has not been reported. Ten-fold dilutions of the fecal suspension containing the SAR-55 strain of HEV were extracted and RT-PCR amplification was performed as follows to determine the highest dilution in which HEV genomes could be detected. 200 ul of fecal suspension was mixed with 0.4 ml of 1.5M NaCl plus 15% polyethylene glycol (PEG) 8000 and kept overnite at 4° C. Pellets were collected by centrifugation for 3 minutes in a microcentrifuge (Beckman, Palo Alto, Calif.) at 16,000 g and dissolved in 475 ul of solution containing 4.2M guanidine thiocyanate, 0.5% N-lauroylsarcosine, 0.25M TRIS-HCl (pH 8.0). 0.15 M dithiothreitol (DTT), and 10 $\mu$g of tRNA. Fifty microliters of 1M TRIS-HCl (pH 8.0), 100 mM EDTA, and 10% SDS was then added. The RNA was extracted twice with phenol-chloroform (1:1) at 65° C., followed by chloroform extraction at room temperature. To the upper phase, 250 $\mu$L of 7.5 M ammonium acetate was added, and nucleic acids were precipitated with 0.6 mL of 2-propanol, washed with 75% ethanol, washed with 100% ethanol, and used for reverse transcription (RT) PCR.

For detection of the HEV genome, two sets of nested primers were used that represented sequences from the 3' region (ORF-2) of the SAR-55 genome. Primers for reverse transcription and the first PCR are shown as SEQ ID NO:99: GTATAACGGATCCACATCTCCCCTTACCTC and SEQ ID NO:100: TACAGATCTATACAACTTAACAGTCGG respectively. Primers for the second PCR are shown as SEQ ID NO: 101: GCGGCAGATCTCACCGACACCATTAG-TAC and SEQ ID NO:102: TAACCTGGATCCTTATGC-CGCCCCTCTTAG respectively. The RNA pellet was dissolved in 20 μL of 0.05 M TRIS-HCl (pH 7.6), 0.06 M KCl, 0.01 M MgCl$_2$, 0.001 M DTT, 40 units of RNasin (Promega Biotec, Madison, Wis.), 16 units of avian myeloblastosis virus reverse transcriptase (Promega Biotec), and 10 pmol of reverse primer and incubated 1 hour at 42° C. To 20 μL of reverse transcriptase mixture was added 100 μL of 0.01 M TRIS-HCl (pH 8.4), 0.05 M KCl, 0.0025 M MgCl$_2$, 0.0002 M each dNTP, 50 pmol of direct primer, 50 pmol of reverse primer, and 4 units of AmpliTaq (Perkin-Elmer Cetus, Norwalk, Conn.) under 100 μL of light mineral oil. The HEV cDNA was amplified by 35 cycles of PCR:1 min at 94° C., 1 min at 55° C., 1 min at 72° C. The products of PCR were analyzed on 1% agarose gels. Then 5 μL of this mixture was used for the second round of amplification under the same conditions, except the extension time was increased to 3 min.

Figure 9:
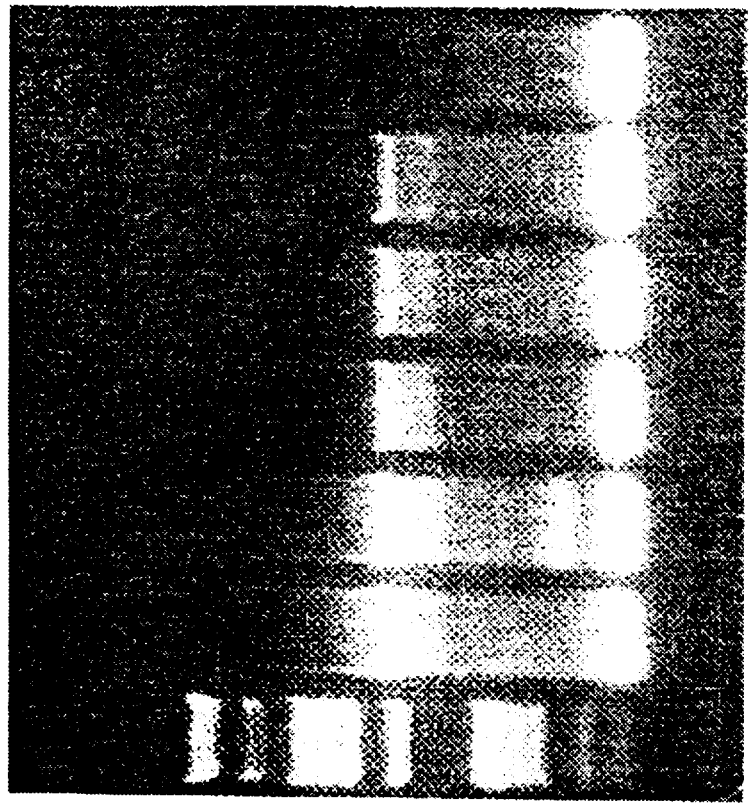
FIG. 9 shows an ethidium bromide stain of a 2% agarose gel on which PCR products produced from extracts of serial ten-fold dilutions (indicated at the top of each lane of the gel) of the 10% fecal suspension of the SAR-55 HEV were separated. The predicted length of the PCR products was about 640 base pairs and the column marked with an (M) contains DNA size markers.

The RT-PCR products produced in all dilutions of the standard HEV feces in the range from $10^{-1}$ to $10^{-5}$ (FIG. 9) were separated on a 2% agarose gel and were detected by ethiduim bromide staining of the gel. A decrease in the amount of the specific PCR product at higher dilutions was observed and the highest dilution of the 10% fecal suspension in which the HEV genome was detected was $10^{-5}$. Therefore, taking into account the dilution factor, the HEV genome titer was approximately $10^{6.7}$ per gram of feces.

In addition, only those dilutions that were shown by RT-PCR to contain the HEV genome were infectious for cynomolgus monkeys. Therefore, the infectivity titer of the standard fecal suspension and its genome titer as detected by RT-PCR were approximately the same. A similar correlation between RT-PCR and infectivity titer was found for one strain of hepatitis C virus [Cristiano et al., (1991) Hepatology, 14:51–55; Farci et al., (1991) N. Engl. J. Med., 25:98–104; Bukh et al., (1992); Proc. Natl. Acad. Sci U.S.A., 89:187–191).

EXAMPLE 12

Active Immunization Using the ORF-2 Protein as a Vaccine and Passive Immunization with Anti-HEV Positive Convalescent Plasma Cynomolgus monkeys (Macaca fascicularis) that were HEV antibody negative (<1:10) in an ELISA based on the 55 kDa ORF-2 protein were individually housed under BL-2 biohazard containment and a suspension (in fetal bovine serum) of feces containing the Pakistani HEV strain SAR-55, diluted to contain 10,000 or 1,000 CID$_{50}$, was used for intravenous inoculation of animals.

For active immunization studies, baculovirus recombinant-expressed 55 kDa ORF-2 protein was purified from 5×10$^8$ SF-9 cells harvested 7 days post-inoculation as described in Example 10. Three mg of the purified 55 kDa protein were precipitated with alum and eight cynomolgus monkeys were immunized by intramuscular injection with 0.5 ml of vaccine containing 50 μg of the alum-precipitated 55 kDa protein. Four monkeys received a single dose and four monkeys received two doses separated by four weeks. Primates were challenged intravenously with 1,000–10,000 CID$_{50}$ of HEV four weeks after the last immunization.

Four cynomolgus monkeys served as controls in the active immunization studies. Cyno-412 and 413 received one dose of placebo (0.5 ml of phosphate buffered saline) and cyno-397 and 849 received two doses of placebo. The control animals were challenged with 1,000–10,000 CID$_{50}$ of HEV.

For passive immunity studies, cyno-384 was infected with 0.5 ml of a 10% pooled stool suspension containing two Chinese HEV isolates, KS1-1987 and KS2-1987 and plasma was repeatedly collected from the animal during convalescence. (Yin et al. (1993) J. Med. Virol., 41:230–241;). Approximately 1% of the blood of cyno-396 and cyno-399 and 10% of the blood of cyno-401 and cyno-402 was replaced with convalescent plasma from cyno-384 having an antibody titer of 1:10,000. Animals were challenged with 1000 CID$_{50}$ of HEV two days after infusion of the plasma. As a control, 10% of the blood of cyno-405 was replaced with anti-HEV negative plasma obtained from cyno-prior to infection with HEV. Cyno-405 was then challenged with 1000 CID$_{50}$ of HEV.

For both the passive and active immunization studies, percutaneous needle biopsies of the liver and samples of serum and feces were collected prior to inoculation and weekly for 15 weeks after inoculation. Sera were assayed for levels of alanine amino transferase (ALT) with commercially available tests (Metpath Inc., Rockville, Md.) and biochemical evidence of hepatitis was defined as a two-fold or greater increase in ALT. Liver biopsies were examined under code and the anti-HEV ELISA utilized was described in Example 10. RNA extraction and RT-PCR were performed as in Example 11 except that RNA from 100 μl of serum or from 100 μl of 10% fecal suspension was extracted with TRIzol Reagent (Gibco BRL, Gaithersburg, Md.) according to the manufacturer's protocol. For quantification, PCR positive serial sera or feces from each animal were combined and serially diluted in ten-fold increments in calf serum. One hundred μl of each dilution were used for RNA extraction and RT-PCR as described earlier in this Example. The PCR protocol used in this study could detect as few as 10 CID$_{50}$ of HEV per ml of serum and as few as 100 CID$_{50}$ per gram of feces.

Peak ALT values of weekly serum samples for 5 weeks prior to inoculation and for 15 weeks post-inoculation were expressed as ratios (post/pre) for each animal. The geometric mean of the ratios from the control group of animals was compared with that from the passively or actively immunized animals using the Simes test (Simes, R. J. (1986) Biometrika, 73:751–754).

The durations of viremia and virus shedding in feces and the HEV genome titers in the control group of animals were compared with those in passively or actively immunized animals using the Wilcoxon test [Noether, G. (1967) in Elements of nonparametric statistics (John Wiley & Sons Inc., New York), pp. 31–36.]. The same test was used to compare the above parameters between passively and actively immunized animals.

For statistical analysis, serum samples that had <10 HEV genomes in 1 ml of serum were assigned a titer of 1:1 and fecal samples that had <100 HEV genomes in 1 g of feces were assigned a titer of 1:10.

Results

Course of hepatitis E infection in nonimmunized animals.

In 3 of 5 nonimmunized animals that were challenged with HEV, biochemical evidence of hepatitis was documented by at least a two-fold increase in serum ALT values. In two animals, significant increases in ALT activity were not found. However, histopathological data documented hepatitis in all 5 animals as shown in Table 6.

Passive immunization. Cyno-396 and 399, which had approximately 1% of their blood replaced with anti-HEV positive convalescent plasma, had an HEV antibody titer of 1:40 when it was determined two days post-transfusion (at the time of challenge) (Table 6). A two-fold fall in HEV antibody titer was observed in both animals 1 week post-transfusion and HEV antibodies fell below the detectable level (<1:10) by 2 weeks post-transfusion. Anti-HEV was

TABLE 6

Histopathological, biochemical, serological, and virological profiles of vaccinated and control animals challenged with HEV.

| Animal # and category | Anti-HEV positive plasma (%) or 55 kDA protein (μg) | Cumulative score of histopathology (number of weeks detected)* | Peak ALT value in U/L (week) pre-inoculation | Peak ALT value in U/L (week) post-inoculation | HEV antibody titer at the time of challenge | HEV genome serum week detected (duration) | HEV genome serum mean log$_{10}$ titer per ml | HEV genome feces week detected (duration) | HEV genome feces mean log$_{10}$ titer per gram |
|---|---|---|---|---|---|---|---|---|---|
| control | | | | | | | | | |
| 405 | 0 | 10+ (8) | 67(0) | 143(9) | <1:10 | 1–11(11) | 3 | 1–11(11) | 5.7 |
| 412 | 0 | 2+ (1) | 34(0) | 45(3) | <1:10 | 1–4(4) | 3 | 2–5(4) | 7 |
| 413 | 0 | 4+ (4) | 44(0) | 261(6) | <1:10 | 2–7(6) | 4.7 | 1–7(7) | 7 |
| 849 | 0 | 1+ (1) | 79(–2) | 133(2) | <1:10 | 1–4(4) | 3.7 | 1–4(4) | 7 |
| 397 | 0 | 3+ (3) | 52(–3) | 139(7) | <1:10 | 2–6(5) | 4.7 | 1–7(7) | 7 |
| passive IP† | | | | | | | | | |
| 396 | 1% | 1+ (1)‡ | 33(0) | 53(6) | 1:40 | 3–5(3) | 4 | 1–6(6) | 5.7 |
| 399 | 1% | 0(0) | 69(0) | 63(11) | 1:40 | 2–4(3) | 3 | 1–4(4) | 4 |
| 401 | 10% | 0(0) | 55(0) | 45(5) | 1:200 | 3(1) | 3.6 | 1–3(3) | 5.7 |
| 402 | 10% | 0(0) | 59(0) | 35(2) | 1:200 | 4–6(3) | 1 | 2–6(5) | 5.7 20 |
| active IP† | | | | | | | | | |
| 003 | 50 μg | 0(0) | 34(–3) | 50(6) | 1:10,000 | 0 | <1 | 24(3) | 3 |
| 009 | 50 μg | 0(0) | 34(–2) | 38(6) | 1:1,000 | 0 | <1 | 0 | <2 |
| 013§ | 50 μg | 0(0) | 44(–3) | 36(7) | 1:100 | 0 | <1 | 1–2(2) | 3 |
| 414 | 50 μg | 0(0) | 65(0) | 73(8) | 1:1,000 | 0 | <1 | 2(1) | 2 |
| 398 | 2 × 50 μg | 0(0) | 31(0) | 41(2) | 1:10,000 | 0 | <1 | 0 | <2 |
| 407 | 2 × 50 μg | 0(0) | 150(0) | 213(4) | 1:10,000 | 0 | <1 | 0 | <2 |

*Necro-inflammatory changes in the liver were rated as 1+, 2+, 3+, 4+ and the weekly scores were summed.
†Immunoprophylaxis
‡Necro-inflammatory changes rated 1+ were detected during two weeks in cyno-396, however, they were consistent with viral hepatitis only during one week.
§Cyno 013 died 9 weeks after challenge.

Necro-inflammatory changes ranged between 1+ and 2+ on a scale of 1+ to 4+ and were temporally associated with elevations of ALT activities in those animals with such elevations.

All control animals seroconverted to HEV 3–5 weeks post-challenge and developed maximum HEV antibody titers ranging from 1:1,000 to 1:32,000. There was a good correlation between the severity of infection, hepatitis, and the level of anti-HEV response. Cyno-405, which had the highest cumulative score for hepatitis, also had the longest period of viremia and viral excretion and the highest level of anti-HEV (Table 6). The duration of viral shedding in feces was the same as, or longer than, that of the viremia. For all of the control animals, titers of the HEV genome in serum were lower ($10^{-3}$–$10^{-4.7}$) than the titers in feces ($10^{-5.7}$–$10^{-7}$). In all five of these animals, viremia and virus shedding in feces were detected for 4–11 weeks and for an average of 4.2 weeks after seroconversion (range 2–9 weeks).

again detected 5 weeks post-challenge in cyno-396 and 4 weeks post-challenge in cyno-399, indicating that infection with HEV had occurred. The maximum HEV antibody titer (1:8,000) was reached 9–10 weeks post-challenge. Neither cynomolgus monkey demonstrated a significant elevation of ALT activity after challenge. However, histologic evidence of hepatitis was detected in cyno-396 and the HEV genome was detected in serum and feces from both animals (Table 6).

Cyno-401 and 402 had approximately 10% of their blood replaced with convalescent plasma. Two days post-transfusion, at the time of challenge, the HEV antibody titer in both cynomolgus monkeys was 1:200 (Table 7).

TABLE 7

HEV antibody profiles in control and immunized cynomolgus monkeys.

| Control animals | HEV antibody titer (week first detected) | HEV antibody max. titer (week) | Passively immunized animals | HEV antibody titer at the time of challenge | HEV antibody max. titer (week after challenge) | Actively immunized animals | HEV antibody max. titer (week after 1st immunization) | HEV antibody max. titer (week after 2nd immunization) | HEV antibody max. titer (week after challenge) |
|---|---|---|---|---|---|---|---|---|---|
| cyno-405 | 1:80 (3) | 1:32,000 (9) | cyno-396 | 1:40 | 1:8,000 (10) | cyno-003 | 1:10,000 (3) | | 1:10,000 (5) |
| cyno-412 | 1:100 (5) | 1:10,000 (7) | cyno-399 | 1:40 | 1:8,000 (9) | cyno-009 | 1:10,000 (3) | | 1:10,000 (1) |
| cyno-413 | 1:100 (5) | 1:10,000 (7) | cyno-401 | 1:200 | 1:4,000 (6) | cyno-013 | 1:100 (2) | | 1:10,000 (3) |
| cyno-849 | 1:100 (3) | 1:1,000 (5) | cyno-402 | 1:200 | 1:80 (12) | cyno-414 | 1:1,000 (3) | | 1:1,000 (0) |
| cyno-397 | 1:100 (3) | 1:10,000 (7) | | | | cyno-398 | 1:1,000 (3) | 1:10,000 (5) | 1:10,000 (0) |
| | | | | | | cyno-407 | 1:1,000 (4) | 1:10,000 (5) | 1:10,000 (0) |

Anti-HEV was detected continuously in both animals during the 15 weeks after challenge and reached a maximum titer of 1:4,000 in cyno-401 but only 1:80 in cyno-402.

of 1:4,000 in cyno-401 but only 1:80 in cyno-402. Biochemical and histologic analyses did not reveal hepatitis in either animal. However, in both animals, HEV viremia and fecal shedding of virus were observed indicating that infection had occurred (Table 6). Thus, passive immunoprophylaxis that achieved a higher titer of antibody protected cynomolgus monkeys against hepatitis after challenge with HEV.

Active immunization. Four primates immunized with one 50 μg dose of the 55 kDa protein developed antibody to the recombinant protein ranging in titer from 1:100 to 1:10,000 (Table 7). One (cyno 013) died of an anesthesia accident 9 weeks after challenge and is included in the analyses (Table 6). The four animals that received two doses of the antigen developed HEV antibodies with titers of 1:10,000. Two of the four monkeys died following intravenous challenge with HEV. This may have also been the result of an anesthesia accident but the exact etiology could not be determined. These two monkeys were deleted from further analyses. None of the 6 remaining animals developed abnormal ALT levels or histologic evidence of hepatitis following challenge (Table 6). Cynomolgus monkeys immunized with either 1 or 2 doses of the 55 kDa protein did not develop viremia. However, 3 of 4 animals that received one dose of the immunogen excreted virus in their feces. In contrast, virus shedding was not observed in either of the two challenged animals that had received two doses of the vaccine.

Most of the actively immunized animals developed higher HEV antibody titers than did passively immunized animals. However, cyno-013 had an HEV antibody titer of 1:100 at the time of challenge, compared with a titer of 1:200 in two animals immunized passively with anti-HEV plasma. Cyno-013, however, demonstrated greater protection against HEV infection than the passively immunized animals. Cyno-009, which had an HEV antibody titer of 1:1,000 at the time of challenge, was completely protected against hepatitis and HEV infection (Table 6). In contrast, cyno-003 was infected and shed HEV in feces, even though it had an HEV antibody titer of 1:10,000 at the time of challenge. However, neither hepatitis nor viremia was detected in this animal or in other cynomolgus monkeys that received one dose of immunogen and had HEV antibody titers of 1:10,000 or greater.

Comparison of course of HEV infection in control and immunized animals.

As measured by histopathology, all immunized animals, with the exception of one of the passively immunized monkeys, were protected against hepatitis after intravenous challenge with HEV. Comparison of mean values for severity of hepatitis and level of viral replication between the control group and the passively and actively immunized animals indicated that, in general, the severity of infection was inversely related to the HEV antibody titer at the time of challenge and diminished in the order: unimmunized>passive immunization (1%) >passive immunization (10%) >active immunization (1 dose) >active immunization (2 doses) (Tables 6,8). However, the number of animals in each of the two subgroups of passively and actively immunized animals was not sufficient to permit statistical analysis. Therefore, statistical analysis was performed for combined passively immunized and combined actively immunized groups respectively in comparison with the combined control groups. The results of this analysis are presented in Table 8.

TABLE 3

Summary of mean values of HEV infection in control and immunized animals.

| Category (number) of animals | Histopathology Mean of cumulative score | Weeks | GM* of peak ALT U/L Pre-inoculation | Post-inoculation | Ratio | HEV antibody titer at the time of challenge | HEV genome Serum mean number of weeks | mean log₁₀ titer | Feces mean number of weeks | mean log₁₀ titer |
|---|---|---|---|---|---|---|---|---|---|---|
| Control (5) | 4+ | 3.4 | 53 | 125 | 2.4 | <1:10 | 6 | 3.8 | 6.6 | 6.7 |
| Passive 1% (2)† | 0.5+ β | 0.5 β | 48 | 58 | 1.2 β | 1:40 | 3 β | 3.5 γ | 5 γ | 4.9 β |
| Passive 10% (2)† | 0 α | 0 α | α 57 | 40 | 0.7 | β 1:200 | 2 α | 2.3 α | α 4 | α 5.7 α |
| Active 1 dose (4)† | 0 γ | 0 γ | 43 | 47 | 1.1 γ | 1:3,025 | 0 α | <1 α | β 1.5 | 2 α |
| Active 2 dose (4)† | 0 | 0 | 68 | 93 | 1.4 | 1:10,000 | 0 | <1 | 0 | <2 |

*Geometric mean
†Passive and active immunoprophylaxis
α - P < 0.01
β - P < 0.05
γ - not significant and they show that the histopathology scores and duration of histologic changes in the control group were statistically different from those of passively or actively immunized animals. The higher post-/pre-inoculation ratios of peak ALT values in the control group were statistically significant when compared with those of the passively or actively immunized animals, indicating protection against biochemical manifestations of hepatitis in both groups of immunized animals. The duration of viremia and the titer of HEV in the feces were significantly lower in both groups of immunized animals than in the control group. Differences in the duration of virus shedding and titer of HEV in the serum, however, were not statistically different between the control group and the passively immunized group, although these parameters were significantly different when the control group was compared with the actively immunized group. Significant differences were also found between passively and actively immunized groups of animals for duration of viremia and fecal shedding as well as for HEV titers.

In sum, the results presented in Tables 6–8 show that both passively and actively acquired HEV antibodies protected cynomolgus monkeys against hepatitis following challenge with virulent HEV. Although all 5 nonimmunized cynomolgus monkeys developed histologic evidence of hepatitis when challenged with 1,000–10,000 CID₅₀ of SAR-55, both animals with passively acquired antibody titers of 1:200 were protected from hepatitis and one of two animals with an antibody titer as low as 1:40 also did not develop hepatitis.

However, it should be noted that actively immunized animals demonstrated complete protection against hepatitis and more effective resistance to HEV infection than did passively immunized animals. For example, in contrast to results obtained from the passively immunized animals, viremia was not detected in actively immunized animals after challenge with HEV. An HEV antibody titer as high as 1:10,000 could be achieved in cynomolgus monkeys after one or two immunizations with the recombinant 55 kDa protein. Although one monkey (013) developed a titer of 1:100 after active immunization, this level still prevented hepatitis and viremia.

The active immunization studies also demonstrated that while a single dose of vaccine prevented HEV viremia, viral shedding in feces was still detected. However, two doses of vaccine were observed to prevent all signs of hepatitis and REV infection. These results thus suggest that a single dose of vaccine administered, for example, to individuals before foreign travel would protect them from hepatitis E in high risk environments.

Finally, it is noted that the results presented are very similar to results reported previously for passive and active immunoprophylaxis of nonhuman primates against hepatitis A: passive immunoprophylaxis prevented hepatitis but not infection whereas vaccination prevented not only hepatitis but infection with HAV as well (Purcell, R. H. et al. (1992) *Vaccine*, 10:5148–5149). It is of interest that the study of immunoprophylaxis for HEV presented herein parallels the previous study of immunoprophylaxis against HAV, both in determination of the titer of antibody that protected (<1:100) and in outcome following intravenous challenge with virulent virus. Since other studies have demonstrated efficacy of comparable titers of passively and actively acquired anti-HAV in humans and have confirmed the predictive value of studies of primates in hepatitis research (Stapleton, J., et al. (1985) *Gastroenterology* 89:637–642; Innis, B. L., et al. (1992) *Vaccine*, 10: S159), it is therefore highly likely that these results in cynomolgus monkeys will be predictive of protection in humans.

EXAMPLE 13

Direct Expression in Yeast of Complete ORF-2 Protein and Lower Molecular Weight Fragments Four cDNA ORF-2 fragments coding for:
1. complete ORF-2 protein (aa 1-660, MW 70979), fragment 1778-1703. (where the fragment numbers refer to the primer numbers given below)
2. ORF-2 protein starting from 34th aa (aa 34-660, MW 67206), fragment 1779-1703.
3. ORF-2 protein starting from 96th aa (aa 96-660, MW 60782), fragment 1780-1703.
4. ORF-2 protein starting from 124th aa (aa 124-660, MW 58050), fragment 1781-1703.

were obtained using PCR by using plasmid P63-2 as template and the synthetic oligonucleotides shown below: SEQ ID NO.:103 (reverse primer #1703) GCACAACCTAGGTTACTATAACTCCCGAGTTTTACC, SEQ ID NO.:104 (direct primer #1778) GGGTTCCCTAGGATGCGCCCTCGGCCTATTTTG, SEQ ID NO.:105 (direct primer #1779) CGTGGGCCTAGGAGCGGCGGTTCCGGCGGTGGT, SEQ ID NO.:106 (direct primer #1780) GCTTGGCCTAG- GCAGGCCCAGCGCCCCGCCGCT and SEQ ID NO.:107 (direct primer #1781) CCGCCACCTAGGGATGT- TGACTCCCGCGGCGCC.

Figure 10:
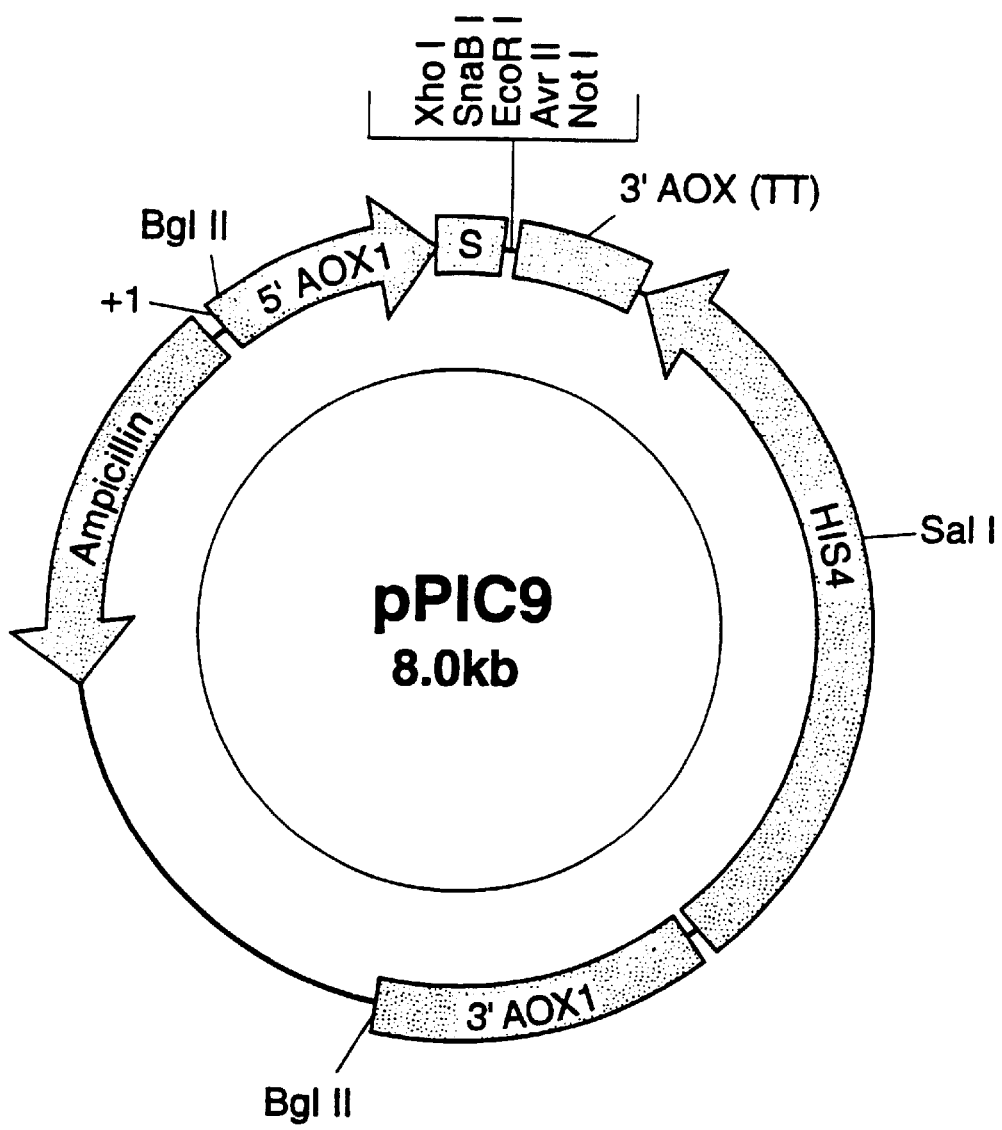
FIG. 10 shows the pPIC9 vector used to express the complete ORF-2 protein or lower molecular weight fragments in yeast.

All sequences shown in SEQ ID NOs: 103–107 contain artificial sequence CCTAGG at their 5' ends preceded by 4 nucleotides. The artificial sequence was a recognition site for Avr II (Bln I) restriction enzyme. Synthesized PCR fragments were cleaved with BlnI and cloned in the AvrII site of pPIC9 vector (FIG. 10) (Invitrogen). Correct orientation of the fragments was confirmed by restriction analysis, using asymmetric EcoRI site present in ORF-2 sequences and in the vector. Purified recombinant plasmids pPIC9-1778 (containing fragment 1778-1703); pPIC9-1779 (containing fragment 1779-1703); pPIC9-1780 (containing fragment 1780-1703) and pPIC9-1781 (containing fragment 1781-1730) were used for transformation of yeast spheroplast (Picha strain) according to Invitrogen protocol. Screening of recombinant clones and analysis of expression were performed using the same protocol. These expressed proteins may be used as immunogens in vaccines and as antigens in immunoassays as described in the present application. Finally, those of skill in the art would recognize that the vector and strain of yeast used in the above example could be replaced by other vectors (e.g. pHIL-F1; Invitrogen) or strains of yeast (e.g. *Saccharomyces Cerevisiae*).

EXAMPLE 14

Purification and Amino Terminal Sequence Analysis of HEV ORF-2 Gene Products Synthesized in SF-9 Insect Cells Infected with Recombinant Baculovirus 63-2-IV-2

As described in Example 10, SF-9 cells were infected with recombinant baculovirus 63-2-IV-2 and harvested seven days post-inoculation. The predominant protein band present on SDS-PAGE of the insect cell lysate was approximately 55 kDa in molecular weight. Further purification of this 55 kDa band was accomplished by ion-exchange column chromatography using DEAE-sepharose with a 150–450 mM NaCl gradient. DEAE fractions were assayed for the presence of the 55 kDa band by SDS-PAGE followed by Coomassie blue staining. The peak fraction was then resolved by polyacrylamide gel electrophoresis in the absence of SDS into three bands of 55 kDa, 61 kDa and a band of intermediate molecular weight. Analysis of each protein band from the polyacrylamide gel by amino-terminal microprotein sequencing revealed that the 55 and 61 kDa proteins shared a unique N-terminus at Ala-112 of SEQ ID NO:2. It is believed that the size differences in the two ORF-2 cleavage products may reflect either different glycosylation patterns or a COOH-terminal cleavage of the larger product.

The third intermediate protein on the polyacrylamide gel was shown to be a baculovirus chitinase protein. The 55 and 61 kDa ORF-2 proteins were resolved into a single symmetrical peak fraction devoid of any chitinase by subjecting peak DEAE fractions to reverse phase HPLC using a micropore system with NaCl and acetonitrile solvents.

EXAMPLE 15

Direct Expression of 55 and 61 kDa Cleavage Products

A cDNA ORF-2 fragment coding for ORF-2 protein starting from the 112th amino acid (amino acids 112–660 of ORF-2) was obtained by PCR using plasmid p63-2 as the template. The cDNA fragment was then inserted into a PBlueBac-3Transfer vector at the BamHI-PstI site in the vector. SF9 insect cells are infected with the recombinant baculovirus generated from this vector and insect cell lysates are analyzed for the presence of the 55 and 61 kDa ORF-2 proteins by Coomassie blue staining of polyacrylamide gels. The directly expressed protein(s) may be used as immunogens in vaccines and as antigens in immunoassays as described herein.

What is claimed is:

1. A purified and isolated hepatitis E virus open-reading frame 2 protein which has its amino terminus at amino acid 112 of a hepatitis E virus open reading frame 2 protein and is characterized by a molecular weight of 55 kilodaltons as determined by polyacrylamide gel electrophoresis, where said protein is produced by a method comprising:

(a) culturing a host cell containing a nucleic acid molecule consisting of nucleotides which encode amino acids 112–660 of a hepatitis E virus open reading frame 2 protein under conditions appropriate to cause expression of said protein; and (b) obtaining said expressed protein from the host cell.

2. A purified and isolated hepatitis E virus open-reading frame 2 protein which has its amino terminus at amino acid 112 of SEQ ID No: 2 and is characterized by a molecular weight of 55 kilodaltons as determined by polyacrylamide gel electrophoresis, where said protein is produced by a method comprising:

(a) culturing a host cell containing a nucleic acid molecule consisting of nucleotides which encode amino acids 112–660 of SEQ ID No: 2 under conditions appropriate to cause expression of said protein; and (b) obtaining said expressed protein from the host cell.

3. A purified and isolated hepatitis E virus open reading frame 2 protein which has its amino terminus at amino acid 112 of a hepatitis E virus open-reading frame 2 protein and is characterized by a molecular weight of 55 kilodaltons as determined by polyacrylamide gel electrophoresis.

4. A purified and isolated hepatitis E virus open-reading frame 2 protein which has its amino terminus at amino acid 112 of SEQ ID No: 2 and is characterized by a molecular weight of 55 kilodaltons as determined by polyacrylamide gel electrophoresis.

5. A kit comprising the protein of claim 1.

6. A kit comprising the protein of claim 2.

7. A kit comprising the protein of claim 3.

8. A kit comprising the protein of claim 4.

9. A pharmaceutical composition comprising the protein of claim 1.

10. A pharmaceutical composition comprising the protein of claim 2.

11. A pharmaceutical composition comprising the protein of claim 3.

12. A pharmaceutical composition comprising the protein of claim 4.

13. A vaccine for immunizing a mammal against hepatitis E, said vaccine comprising the protein of claim 1 in an amount effective to stimulate the production of protective antibodies against hepatitis E in said mammal.

14. A vaccine for immunizing a mammal against hepatitis E, said vaccine comprising the protein of claim 2 in an amount effective to stimulate the production of protective antibodies against hepatitis E in said mammal.

15. A vaccine for immunizing a mammal against hepatitis E, said vaccine comprising the protein of claim 3 in an amount effective to stimulate the production of protective antibodies against hepatitis E in said mammal.

16. A vaccine for immunizing a mammal against hepatitis E, said vaccine comprising the protein of claim 4 in an amount effective to stimulate the production of protective antibodies against hepatitis E in said mammal.

* * * * *

SEQUENCE LISTING (1) GENERAL INFORMATION:

(iii) NUMBER OF SEQUENCES: 107

(2) INFORMATION FOR SEQ ID NO: 1

(i) SEQUENCE CHARACTERISTICS:
        (A) LENGTH: 1693 AMINO ACID RESIDUES
        (B) TYPE: AMINO ACID
        (C) STRANDEDNESS: UNKNOWN
        (D) TOPOLOGY: UNKNOWN (xi) SEQUENCE DESCRIPTION: SEQ ID NO: 1:

```
Met Glu Ala His Gln Phe Ile Lys Ala Pro Gly Ile Thr Thr Ala
1               5                   10                  15

Ile Glu Gln Ala Ala Leu Ala Ala Ala Asn Ser Ala Leu Ala Asn
                20                  25                  30

Ala Val Val Val Arg Pro Phe Leu Ser His Gln Gln Ile Glu Ile
                35                  40                  45
```

-continued

```
Leu Ile Asn Leu Met Gln Pro Arg Gln Leu Val Phe Arg Pro Glu
             50                  55                  60

Val Phe Trp Asn His Pro Ile Gln Arg Val Ile His Asn Glu Leu
             65                  70                  75

Glu Leu Tyr Cys Arg Ala Arg Ser Gly Arg Cys Leu Glu Ile Gly
             80                  85                  90

Ala His Pro Arg Ser Ile Asn Asp Asn Pro Asn Val Val His Arg
             95                 100                 105

Cys Phe Leu Arg Pro Ala Gly Arg Asp Val Gln Arg Trp Tyr Thr
            110                 115                 120

Ala Pro Thr Arg Gly Pro Ala Ala Asn Cys Arg Arg Ser Ala Leu
            125                 130                 135

Arg Gly Leu Pro Ala Ala Asp Arg Thr Tyr Cys Phe Asp Gly Phe
            140                 145                 150

Ser Gly Cys Asn Phe Pro Ala Glu Thr Gly Ile Ala Leu Tyr Ser
            155                 160                 165

Leu His Asp Met Ser Pro Ser Asp Val Ala Glu Ala Met Phe Arg
            170                 175                 180

His Gly Met Thr Arg Leu Tyr Ala Ala Leu His Leu Pro Pro Glu
            185                 190                 195

Val Leu Leu Pro Pro Gly Thr Tyr Arg Thr Ala Ser Tyr Leu Leu
            200                 205                 210

Ile His Asp Gly Arg Arg Val Val Thr Tyr Glu Gly Asp Thr
            215                 220                 225

Ser Ala Gly Tyr Asn His Asp Val Ser Asn Leu Arg Ser Trp Ile
            230                 235                 240

Arg Thr Thr Lys Val Thr Gly Asp His Pro Leu Val Ile Glu Arg
            245                 250                 255

Val Arg Ala Ile Gly Cys His Phe Val Leu Leu Thr Ala Ala
            260                 265                 270

Pro Glu Pro Ser Pro Met Pro Tyr Val Pro Tyr Pro Arg Ser Thr
            275                 280                 285

Glu Val Tyr Val Arg Ser Ile Phe Gly Pro Gly Thr Pro Ser
            290                 295                 300

Leu Phe Pro Thr Ser Cys Ser Thr Lys Ser Thr Phe His Ala Val
            305                 310                 315

Pro Ala His Ile Trp Asp Arg Leu Met Leu Phe Gly Ala Thr Leu
            320                 325                 330

Asp Asp Gln Ala Phe Cys Cys Ser Arg Leu Met Thr Tyr Leu Arg
            335                 340                 345

Gly Ile Ser Tyr Lys Val Thr Val Gly Thr Leu Val Ala Asn Glu
            350                 355                 360

Gly Trp Asn Ala Ser Glu Asp Ala Leu Thr Ala Val Ile Thr Ala
            365                 370                 375

Ala Tyr Leu Thr Ile Cys His Gln Arg Tyr Leu Arg Thr Gln Ala
            380                 385                 390

Ile Ser Lys Gly Met Arg Arg Leu Glu Arg Glu His Ala Gln Lys
            395                 400                 405

Phe Ile Thr Arg Leu Tyr Ser Trp Leu Phe Glu Lys Ser Gly Arg
            410                 415                 420

Asp Tyr Ile Pro Gly Arg Gln Leu Glu Phe Tyr Ala Gln Cys Arg
            425                 430                 435
```

```
Arg Trp Leu Ser Ala Gly Phe His Leu Asp Pro Arg Val Leu Val
                440                 445                 450

Phe Asp Glu Ser Ala Pro Cys His Cys Arg Thr Ala Ile Arg Lys
                455                 460                 465

Ala Val Ser Lys Phe Cys Cys Phe Met Lys Trp Leu Gly Gln Glu
                470                 475                 480

Cys Thr Cys Phe Leu Gln Pro Ala Glu Gly Val Val Gly Asp Gln
                485                 490                 495

Gly His Asp Asn Glu Ala Tyr Glu Gly Ser Asp Val Asp Pro Ala
                500                 505                 510

Glu Ser Ala Ile Ser Asp Ile Ser Gly Ser Tyr Val Val Pro Gly
                515                 520                 525

Thr Ala Leu Gln Pro Leu Tyr Gln Ala Leu Asp Leu Pro Ala Glu
                530                 535                 540

Ile Val Ala Arg Ala Gly Arg Leu Thr Ala Thr Val Lys Val Ser
                545                 550                 555

Gln Val Asp Gly Arg Ile Asp Cys Glu Thr Leu Leu Gly Asn Lys
                560                 565                 570

Thr Phe Arg Thr Ser Phe Val Asp Gly Ala Val Leu Glu Thr Asn
                575                 580                 585

Gly Pro Glu Arg His Asn Leu Ser Phe Asp Ala Ser Gln Ser Thr
                590                 595                 600

Met Ala Ala Gly Pro Phe Ser Leu Thr Tyr Ala Ala Ser Ala Ala
                605                 610                 615

Gly Leu Glu Val Arg Tyr Val Ala Ala Gly Leu Asp His Arg Ala
                620                 625                 630

Val Phe Ala Pro Gly Val Ser Pro Arg Ser Ala Pro Gly Glu Val
                635                 640                 645

Thr Ala Phe Cys Ser Ala Leu Tyr Arg Phe Asn Arg Glu Ala Gln
                650                 655                 660

Arg Leu Ser Leu Thr Gly Asn Phe Trp Phe His Pro Glu Gly Leu
                665                 670                 675

Leu Gly Pro Phe Ala Pro Phe Ser Pro Gly His Val Trp Glu Ser
                680                 685                 690

Ala Asn Pro Phe Cys Gly Glu Ser Thr Leu Tyr Thr Arg Thr Trp
                695                 700                 705

Ser Glu Val Asp Ala Val Pro Ser Pro Ala Gln Pro Asp Leu Gly
                710                 715                 720

Phe Thr Ser Glu Pro Ser Ile Pro Ser Arg Ala Ala Thr Pro Thr
                725                 730                 735

Pro Ala Ala Pro Leu Pro Pro Ala Pro Asp Pro Ser Pro Thr
                740                 745                 750

Leu Ser Ala Pro Ala Arg Gly Glu Pro Ala Pro Gly Ala Thr Ala
                755                 760                 765

Arg Ala Pro Ala Ile Thr His Gln Thr Ala Arg His Arg Arg Leu
                770                 775                 780

Leu Phe Thr Tyr Pro Asp Gly Ser Lys Val Phe Ala Gly Ser Leu
                785                 790                 795

Phe Glu Ser Thr Cys Thr Trp Leu Val Asn Ala Ser Asn Val Asp
                800                 805                 810

His Arg Pro Gly Gly Gly Leu Cys His Ala Phe Tyr Gln Arg Tyr
                815                 820                 825

Pro Ala Ser Phe Asp Ala Ala Ser Phe Val Met Arg Asp Gly Ala
```

-continued

```
                830               835               840
Ala Ala Tyr Thr Leu Thr Pro Arg Pro Ile Ile His Ala Val Ala
                845               850               855
Pro Asp Tyr Arg Leu Glu His Asn Pro Lys Arg Leu Glu Ala Ala
                860               865               870
Tyr Arg Glu Thr Cys Ser Arg Leu Gly Thr Ala Ala Tyr Pro Leu
                875               880               885
Leu Gly Thr Gly Ile Tyr Gln Val Pro Ile Gly Pro Ser Phe Asp
                890               895               900
Ala Trp Glu Arg Asn His Arg Pro Gly Asp Glu Leu Tyr Leu Pro
                905               910               915
Glu Leu Ala Ala Arg Trp Phe Glu Ala Asn Arg Pro Thr Cys Pro
                920               925               930
Thr Leu Thr Ile Thr Glu Asp Val Ala Arg Thr Ala Asn Leu Ala
                935               940               945
Ile Glu Leu Asp Ser Ala Thr Asp Val Gly Arg Ala Cys Ala Gly
                950               955               960
Cys Arg Val Thr Pro Gly Val Val Gln Tyr Gln Phe Thr Ala Gly
                965               970               975
Val Pro Gly Ser Gly Lys Ser Arg Ser Ile Thr Gln Ala Asp Val
                980               985               990
Asp Val Val Val Pro Thr Arg Glu Leu Arg Asn Ala Trp Arg
                995              1000              1005
Arg Arg Gly Phe Ala Ala Phe Thr Pro His Thr Ala Ala Arg Val
               1010              1015              1020
Thr Gln Gly Arg Arg Val Val Ile Asp Glu Ala Pro Ser Leu Pro
               1025              1030              1035
Pro His Leu Leu Leu Leu His Met Gln Arg Ala Ala Thr Val His
               1040              1045              1050
Leu Leu Gly Asp Pro Asn Gln Ile Pro Ala Ile Asp Phe Glu His
               1055              1060              1065
Ala Gly Leu Val Pro Ala Ile Arg Pro Asp Leu Ala Pro Thr Ser
               1070              1075              1080
Trp Trp His Val Thr His Arg Cys Pro Ala Asp Val Cys Glu Leu
               1085              1090              1095
Ile Arg Gly Ala Tyr Pro Met Ile Gln Thr Thr Ser Arg Val Leu
               1100              1105              1110
Arg Ser Leu Phe Trp Gly Glu Pro Ala Val Gly Gln Lys Leu Val
               1115              1120              1125
Phe Thr Gln Ala Ala Lys Ala Ala Asn Pro Gly Ser Val Thr Val
               1130              1135              1140
His Glu Ala Gln Gly Ala Thr Tyr Thr Glu Thr Thr Ile Ile Ala
               1145              1150              1155
Thr Ala Asp Ala Arg Gly Leu Ile Gln Ser Ser Arg Ala His Ala
               1160              1165              1170
Ile Val Ala Leu Thr Arg His Thr Glu Lys Cys Val Ile Ile Asp
               1175              1180              1185
Ala Pro Gly Leu Leu Arg Glu Val Gly Ile Ser Asp Ala Ile Val
               1190              1195              1200
Asn Asn Phe Phe Leu Ala Gly Gly Glu Ile Gly His Gln Arg Pro
               1205              1210              1215
Ser Val Ile Pro Arg Gly Asn Pro Asp Ala Asn Val Asp Thr Leu
               1220              1225              1230
```

-continued

Ala Ala Phe Pro Pro Ser Cys Glu Ile Ser Ala Phe His Glu Leu
            1235                1240                1245

Ala Glu Glu Leu Gly His Arg Pro Ala Pro Val Ala Ala Val Leu
        1250                1255                1260

Pro Pro Cys Pro Glu Leu Glu Gln Gly Leu Leu Tyr Leu Pro Gln
        1265                1270                1275

Glu Leu Thr Thr Cys Asp Ser Val Thr Phe Glu Leu Thr Asp
        1280                1285                1290

Ile Val His Cys Arg Met Ala Ala Pro Ser Gln Arg Lys Ala Val
        1295                1300                1305

Leu Ser Thr Leu Val Gly Arg Tyr Gly Arg Arg Thr Lys Leu Tyr
        1310                1315                1320

Asn Ala Ser His Ser Asp Val Arg Asp Ser Leu Ala Arg Phe Ile
        1325                1330                1335

Pro Ala Ile Gly Pro Val Gln Val Thr Thr Cys Glu Leu Tyr Glu
        1340                1345                1350

Leu Glu Glu Ala Met Val Glu Lys Gly Gln Asp Gly Ser Ala Val
        1355                1360                1365

Leu Glu Leu Asp Leu Cys Ser Arg Asp Val Ser Arg Ile Thr Phe
        1370                1375                1380

Phe Gln Lys Asp Cys Asn Lys Phe Thr Thr Gly Glu Thr Ile Ala
        1385                1390                1395

His Gly Lys Val Gly Gln Gly Ile Ser Ala Trp Ser Lys Thr Phe
        1400                1405                1410

Cys Ala Leu Phe Gly Pro Trp Phe Arg Ala Ile Glu Lys Ala Ile
        1415                1420                1425

Leu Ala Leu Leu Pro Gln Gly Val Phe Tyr Gly Asp Ala Phe Asp
        1430                1435                1440

Asp Thr Val Phe Ser Ala Ala Val Ala Ala Ala Lys Ala Ser Met
        1445                1450                1455

Val Phe Glu Asn Asp Phe Ser Glu Phe Asp Ser Thr Gln Asn Asn
        1460                1465                1470

Phe Ser Leu Gly Leu Glu Cys Ala Ile Met Glu Glu Cys Gly Met
        1475                1480                1485

Pro Gln Trp Leu Ile Arg Leu Tyr His Leu Ile Arg Ser Ala Trp
        1490                1495                1500

Ile Leu Gln Ala Pro Lys Glu Ser Leu Arg Gly Phe Trp Lys Lys
        1505                1510                1515

His Ser Gly Glu Pro Gly Thr Leu Leu Trp Asn Thr Val Trp Asn
        1520                1525                1530

Met Ala Val Ile Thr His Cys Tyr Asp Phe Arg Asp Leu Gln Val
        1535                1540                1545

Ala Ala Phe Lys Gly Asp Asp Ser Ile Val Leu Cys Ser Glu Tyr
        1550                1555                1560

Arg Gln Ser Pro Gly Ala Ala Val Leu Ile Ala Gly Cys Gly Leu
        1565                1570                1575

Lys Leu Lys Val Asp Phe Arg Pro Ile Gly Leu Tyr Ala Gly Val
        1580                1585                1590

Val Val Ala Pro Gly Leu Gly Ala Leu Pro Asp Val Val Arg Phe
        1595                1600                1605

Ala Gly Arg Leu Thr Glu Lys Asn Trp Gly Pro Gly Pro Glu Arg
        1610                1615                1620

```
Ala Glu Gln Leu Arg Leu Ala Val Ser Asp Phe Leu Arg Lys Leu
            1625                1630                1635

Thr Asn Val Ala Gln Met Cys Val Asp Val Val Ser Arg Val Tyr
            1640                1645                1650

Gly Val Ser Pro Gly Leu Val His Asn Leu Ile Glu Met Leu Gln
            1655                1660                1665

Ala Val Ala Asp Gly Lys Ala His Phe Thr Glu Ser Val Lys Pro
            1670                1675                1680

Val Leu Asp Leu Thr Asn Ser Ile Leu Cys Arg Val Glu
            1685                1690

(2) INFORMATION FOR SEQ ID NO: 2:

(i) SEQUENCE CHARACTERISTICS:
        (A) LENGTH: 660 amino acid residues
        (B) TYPE: amino acid
        (C) STRANDEDNESS: unknown
        (D) TOPOLOGY: unknown (xi) SEQUENCE DESCRIPTION: SEQ ID NO: 2:

Met Arg Pro Arg Pro Ile Leu Leu Leu Leu Met Phe Leu Pro
1               5                   10                  15

Met Leu Pro Ala Pro Pro Gly Gln Pro Ser Gly Arg Arg Arg
            20                  25                  30

Gly Arg Arg Ser Gly Gly Ser Gly Gly Gly Phe Trp Gly Asp Arg
            35                  40                  45

Val Asp Ser Gln Pro Phe Ala Ile Pro Tyr Ile His Pro Thr Asn
            50                  55                  60

Pro Phe Ala Pro Asp Val Thr Ala Ala Gly Ala Gly Pro Arg
            65                  70                  75

Val Arg Gln Pro Ala Arg Pro Leu Gly Ser Ala Trp Arg Asp Gln
            80                  85                  90

Ala Gln Arg Pro Ala Ala Ala Ser Arg Arg Pro Thr Thr Ala
            95                  100                 105

Gly Ala Ala Pro Leu Thr Ala Val Ala Pro Ala His Asp Thr Pro
            110                 115                 120

Pro Val Pro Asp Val Asp Ser Arg Gly Ala Ile Leu Arg Arg Gln
            125                 130                 135

Tyr Asn Leu Ser Thr Ser Pro Leu Thr Ser Ser Val Ala Thr Gly
            140                 145                 150

Thr Asn Leu Val Leu Tyr Ala Ala Pro Leu Ser Pro Leu Leu Pro
            155                 160                 165

Leu Gln Asp Gly Thr Asn Thr His Ile Met Ala Thr Glu Ala Ser
            170                 175                 180

Asn Tyr Ala Gln Tyr Arg Val Ala Arg Ala Thr Ile Arg Tyr Arg
            185                 190                 195

Pro Leu Val Pro Asn Ala Val Gly Gly Tyr Ala Ile Ser Ile Ser
            200                 205                 210

Phe Tyr Pro Gln Thr Thr Thr Pro Thr Ser Val Asp Met Asn
            215                 220                 225

Ser Ile Thr Ser Thr Asp Val Arg Ile Leu Val Gln Pro Gly Ile
            230                 235                 240

Ala Ser Glu Leu Val Ile Pro Ser Glu Arg Leu His Tyr Arg Asn
            245                 250                 255

Gln Gly Trp Arg Ser Val Glu Thr Ser Gly Val Ala Glu Glu Glu
            260                 265                 270
```

```
Ala Thr Ser Gly Leu Val Met Leu Cys Ile His Gly Ser Pro Val
            275                 280                 285

Asn Ser Tyr Thr Asn Thr Pro Tyr Thr Gly Ala Leu Gly Leu Leu
            290                 295                 300

Asp Phe Ala Leu Glu Leu Glu Phe Arg Asn Leu Thr Pro Gly Asn
            305                 310                 315

Thr Asn Thr Arg Val Ser Arg Tyr Ser Thr Ala Arg His Arg
            320                 325                 330

Leu Arg Arg Gly Ala Asp Gly Thr Ala Glu Leu Thr Thr Ala
            335                 340                 345

Ala Thr Arg Phe Met Lys Asp Leu Tyr Phe Thr Ser Thr Asn Gly
            350                 355                 360

Val Gly Glu Ile Gly Arg Gly Ile Ala Leu Thr Leu Phe Asn Leu
            365                 370                 375

Ala Asp Thr Leu Leu Gly Gly Leu Pro Thr Glu Leu Ile Ser Ser
            380                 385                 390

Ala Gly Gly Gln Leu Phe Tyr Ser Arg Pro Val Val Ser Ala Asn
            395                 400                 405

Gly Glu Pro Thr Val Lys Leu Tyr Thr Ser Val Glu Asn Ala Gln
            410                 415                 420

Gln Asp Lys Gly Ile Ala Ile Pro His Asp Ile Asp Leu Gly Glu
            425                 430                 435

Ser Arg Val Val Ile Gln Asp Tyr Asp Asn Gln His Glu Gln Asp
            440                 445                 450

Arg Pro Thr Pro Ser Pro Ala Pro Ser Arg Pro Phe Ser Val Leu
            455                 460                 465

Arg Ala Asn Asp Val Leu Trp Leu Ser Leu Thr Ala Ala Glu Tyr
            470                 475                 480

Asp Gln Ser Thr Tyr Gly Ser Ser Thr Gly Pro Val Tyr Val Ser
            485                 490                 495

Asp Ser Val Thr Leu Val Asn Val Ala Thr Gly Ala Gln Ala Val
            500                 505                 510

Ala Arg Ser Leu Asp Trp Thr Lys Val Thr Leu Asp Gly Arg Pro
            515                 520                 525

Leu Ser Thr Ile Gln Gln Tyr Ser Lys Thr Phe Phe Val Leu Pro
            530                 535                 540

Leu Arg Gly Lys Leu Ser Phe Trp Glu Ala Gly Thr Thr Lys Ala
            545                 550                 555

Gly Tyr Pro Tyr Asn Tyr Asn Thr Thr Ala Ser Asp Gln Leu Leu
            560                 565                 570

Val Glu Asn Ala Ala Gly His Arg Val Ala Ile Ser Thr Tyr Thr
            575                 580                 585

Thr Ser Leu Gly Ala Gly Pro Val Ser Ile Ser Ala Val Ala Val
            590                 595                 600

Leu Ala Pro His Ser Val Leu Ala Leu Leu Glu Asp Thr Met Asp
            605                 610                 615

Tyr Pro Ala Arg Ala His Thr Phe Asp Asp Phe Cys Pro Glu Cys
            620                 625                 630

Arg Pro Leu Gly Leu Gln Gly Cys Ala Phe Gln Ser Thr Val Ala
            635                 640                 645

Glu Leu Gln Arg Leu Lys Met Lys Val Gly Lys Thr Arg Glu Leu
            650                 655                 660
```

(2) INFORMATION FOR SEQ ID NO: 3:

(i) SEQUENCE CHARACTERISTICS:
        (A) LENGTH: 123 amino acid residues
        (B) TYPE: amino acid
        (C) STRANDEDNESS: unknown
        (D) TOPOLOGY: unknown (xi) SEQUENCE DESCRIPTION: SEQ ID NO: 3:

```
Met Asn Asn Met Ser Phe Ala Ala Pro Met Gly Ser Arg Pro Cys
1               5                   10                  15

Ala Leu Gly Leu Phe Cys Cys Cys Ser Ser Cys Phe Cys Leu Cys
                20                  25                  30

Cys Pro Arg His Arg Pro Val Ser Arg Leu Ala Ala Val Val Gly
                35                  40                  45

Gly Ala Ala Ala Val Pro Ala Val Val Ser Gly Val Thr Gly Leu
                50                  55                  60

Ile Leu Ser Pro Ser Gln Ser Pro Ile Phe Ile Gln Pro Thr Pro
                65                  70                  75

Ser Pro Pro Met Ser Pro Leu Arg Pro Gly Leu Asp Leu Val Phe
                80                  85                  90

Ala Asn Pro Pro Asp His Ser Ala Pro Leu Gly Val Thr Arg Pro
                95                  100                 105

Ser Ala Pro Pro Leu Pro His Val Val Asp Leu Pro Gln Leu Gly
                110                 115                 120

Pro Arg Arg
```

(2) INFORMATION FOR SEQ ID NO: 4:

(i) SEQUENCE CHARACTERISTICS:
        (A) LENGTH: 7168 base pairs
        (B) TYPE: nucleic acid
        (C) STRANDEDNESS: single
        (D) TOPOLOGY: linear (xi) SEQUENCE DESCRIPTION: SEQ ID NO: 4:

```
AGGCAGACCA CATATGTGGT CGATGCCATG GAGGCCCATC AGTTTATCAA          50
GGCTCCTGGC ATCACTACTG CTATTGAGCA GGCTGCTCTA GCAGCGGCCA         100
ACTCTGCCCT TGCGAATGCT GTGGTAGTTA GGCCTTTTCT CTCTCACCAG         150
CAGATTGAGA TCCTTATTAA CCTAATGCAA CCTCGCCAGC TTGTTTTCCG         200
CCCCGAGGTT TTCTGGAACC ATCCCATCCA GCGTGTTATC CATAATGAGC         250
TGGAGCTTTA CTGTCGCGCC CGCTCCGGCC GCTGCCTCGA AATTGGTGCC         300
CACCCCCGCT CAATAAATGA CAATCCTAAT GTGGTCCACC GTTGCTTCCT         350
CCGTCCTGCC GGGCGTGATG TTCAGCGTTG GTATACTGCC CCTACCCGCG         400
GGCCGGCTGC TAATTGCCGG CGTTCCGCGC TGCGCGGGCT CCCCGCTGCT         450
GACCGCACTT ACTGCTTCGA CGGGTTTTCT GGCTGTAACT TTCCCGCCGA         500
GACGGGCATC GCCCTCTATT CTCTCCATGA TATGTCACCA TCTGATGTCG         550
CCGAGGCTAT GTTCCGCCAT GGTATGACGC GGCTTTACGC TGCCCTCCAC         600
CTCCCGCCTG AGGTCCTGTT GCCCCCTGGC ACATACCGCA CCGCGTCGTA         650
CTTGCTGATC CATGACGGCA GGCGCGTTGT GGTGACGTAT GAGGGTGACA         700
CTAGTGCTGG TTATAACCAC GATGTTTCCA ACCTGCGCTC CTGGATTAGA         750
ACCACTAAGG TTACCGGAGA CCACCCTCTC GTCATCGAGC GGGTTAGGGC         800
```

```
CATTGGCTGC CACTTTGTCC TTTTACTCAC GGCTGCTCCG GAGCCATCAC          850

CTATGCCCTA TGTCCCTTAC CCCCGGTCTA CCGAGGTCTA TGTCCGATCG          900

ATCTTCGGCC CGGGTGGCAC CCCCTCCCTA TTTCCAACCT CATGCTCCAC          950

CAAGTCGACC TTCCATGCTG TCCCTGCCCA TATCTGGAC CGTCTCATGT          1000

TGTTCGGGGC CACCCTAGAT GACCAAGCCT TTTGCTGCTC CCGCCTAATG          1050

ACTTACCTCC GCGGCATTAG CTACAAGGTT ACTGTGGGCA CCCTTGTTGC          1100

CAATGAAGGC TGGAACGCCT CTGAGGACGC TCTTACAGCT GTCATCACTG          1150

CCGCCTACCT TACCATCTGC CACCAGCGGT ACCTCCGCAC TCAGGCTATA          1200

TCTAAGGGGA TGCGTCGCCT GGAGCGGGAG CATGCTCAGA AGTTTATAAC          1250

ACGCCTCTAC AGTTGGCTCT TTGAGAAGTC CGGCCGTGAT TATATCCCCG          1300

GCCGTCAGTT GGAGTTCTAC GCTCAGTGTA GGCGCTGGCT CTCGGCCGGC          1350

TTTCATCTTG ACCCACGGGT GTTGGTTTTT GATGAGTCGG CCCCCTGCCA          1400

CTGTAGGACT GCGATTCGTA AGGCGGTCTC AAAGTTTTGC TGCTTTATGA          1450

AGTGGCTGGG CCAGGAGTGC ACCTGTTTTC TACAACCTGC AGAAGGCGTC          1500

GTTGGCGACC AGGGCCATGA CAACGAGGCC TATGAGGGGT CTGATGTTGA          1550

CCCTGCTGAA TCCGCTATTA GTGACATATC TGGGTCCTAC GTAGTCCCTG          1600

GCACTGCCCT CCAACCGCTT TACCAAGCCC TTGACCTCCC CGCTGAGATT          1650

GTGGCTCGTG CAGGCCGGCT GACCGCCACA GTAAAGGTCT CCCAGGTCGA          1700

CGGGCGGATC GATTGTGAGA CCCTTCTCGG TAATAAAACC TTCCGCACGT          1750

CGTTTGTTGA CGGGGCGGTT TTAGAGACTA ATGGCCCAGA GCGCCACAAT          1800

CTCTCTTTTG ATGCCAGTCA GAGCACTATG GCCGCCGGCC CTTTCAGTCT          1850

CACCTATGCC GCCTCTGCTG CTGGGCTGGA GGTGCGCTAT GTCGCCGCCG          1900

GGCTTGACCA CCGGGCGGTT TTTGCCCCCG GCGTTTCACC CCGGTCAGCC          1950

CCTGGCGAGG TCACCGCCTT CTGTTCTGCC CTATACAGGT TTAATCGCGA          2000

GGCCCAGCGC CTTTCGCTGA CCGGTAATTT TTGGTTCCAT CCTGAGGGGC          2050

TCCTTGGCCC CTTTGCCCCG TTTTCCCCCG GGCATGTTTG GGAGTCGGCT          2100

AATCCATTCT GTGGCGAGAG CACACTTTAC ACCCGCACTT GGTCGGAGGT          2150

TGATGCTGTT CCTAGTCCAG CCCAGCCCGA CTTAGGTTTT ACATCTGAGC          2200

CTTCTATACC TAGTAGGGCC GCCACACCTA CCCCGGCGGC CCCTCTACCC          2250

CCCCCTGCAC CGGATCCTTC CCCTACTCTC TCTGCTCCGG CGCGTGGTGA          2300

GCCGGCTCCT GGCGCTACCG CCAGGGCCCC AGCCATAACC CACCAGACGG          2350

CCCGGCATCG CCGCCTGCTC TTTACCTACC CGGATGGCTC TAAGGTGTTC          2400

GCCGGCTCGC TGTTTGAGTC GACATGTACC TGGCTCGTTA ACGCGTCTAA          2450

TGTTGACCAC CGCCCTGGCG GTGGGCTCTG TCATGCATTT TACCAGAGGT          2500

ACCCCGCCTC CTTTGATGCT GCCTCTTTTG TGATGCGCGA CGGCGCGGCC          2550

GCCTACACAT TAACCCCCCG GCCAATAATT CATGCCGTCG CTCCTGATTA          2600

TAGGTTGGAA CATAACCCAA AGAGGCTTGA GGCTGCCTAC CGGGAGACTT          2650

GCTCCCGCCT CGGTACCGCT GCATACCCAC TCCTCGGGAC CGGCATATAC          2700

CAGGTGCCGA TCGGTCCCAG TTTTGACGCC TGGGAGCGGA ATCACCGCCC          2750
```

| | |
|---|---|
| CGGGGACGAG TTGTACCTTC CTGAGCTTGC TGCCAGATGG TTCGAGGCCA | 2800 |
| ATAGGCCGAC CTGCCCAACT CTCACTATAA CTGAGGATGT TGCGCGGACA | 2850 |
| GCAAATCTGG CTATCGAACT TGACTCAGCC ACAGACGTCG GCCGGGCCTG | 2900 |
| TGCCGGCTGT CGAGTCACCC CCGGCGTTGT GCAGTACCAG TTTACCGCAG | 2950 |
| GTGTGCCTGG ATCCGGCAAG TCCCGCTCTA TTACCCAAGC CGACGTGGAC | 3000 |
| GTTGTCGTGG TCCCGACCCG GGAGTTGCGT AATGCCTGGC GCCGCCGCGG | 3050 |
| CTTCGCTGCT TTCACCCCGC ACACTGCGGC TAGAGTCACC CAGGGGCGCC | 3100 |
| GGGTTGTCAT TGATGAGGCC CCGTCCCTTC CCCCTCATTT GCTGCTGCTC | 3150 |
| CACATGCAGC GGGCCGCCAC CGTCCACCTT CTTGGCGACC CGAATCAGAT | 3200 |
| CCCAGCCATC GATTTTGAGC ACGCCGGGCT CGTTCCCGCC ATCAGGCCCG | 3250 |
| ATTTGGCCCC CACCTCCTGG TGGCATGTTA CCCATCGCTG CCCTGCGGAT | 3300 |
| GTATGTGAGC TAATCCGCGG CGCATACCCT ATGATTCAGA CCACTAGTCG | 3350 |
| GGTCCTCCGG TCGTTGTTCT GGGGTGAGCC CGCCGTTGGG CAGAAGCTAG | 3400 |
| TGTTCACCCA GGCGGCTAAG GCCGCCAACC CCGGTTCAGT GACGGTCCAT | 3450 |
| GAGGCACAGG GCGCTACCTA CACAGAGACT ACCATCATTG CCACGGCAGA | 3500 |
| TGCTCGAGGC CTCATTCAGT CGTCCCGAGC TCATGCCATT GTTGCCTTGA | 3550 |
| CGCGCCACAC TGAGAAGTGC GTCATCATTG ACGCACCAGG CCTGCTTCGC | 3600 |
| GAGGTGGGCA TCTCCGATGC AATCGTTAAT AACTTTTTCC TTGCTGGTGG | 3650 |
| CGAAATTGGC CACCAGCGCC CATCTGTTAT CCCTCGCGGC AATCCTGACG | 3700 |
| CCAATGTTGA CACCTTGGCT GCCTTCCCGC CGTCTTGCCA GATTAGCGCC | 3750 |
| TTCCATCAGT TGGCTGAGGA GCTTGGCCAC AGACCTGCCC CTGTCGCGGC | 3800 |
| TGTTCTACCG CCCTGCCCTG AGCTTGAACA GGGCCTTCTC TACCTGCCCC | 3850 |
| AAGAACTCAC CACCTGTGAT AGTGTCGTAA CATTTGAATT AACAGATATT | 3900 |
| GTGCATTGTC GTATGGCCGC CCCGAGCCAG CGCAAGGCCG TGCTGTCCAC | 3950 |
| GCTCGTGGGC CGTTATGGCC GCCGCACAAA GCTCTACAAT GCCTCCCACT | 4000 |
| CTGATGTTCG CGACTCTCTC GCCCGTTTTA TCCCGGCCAT TGGCCCCGTA | 4050 |
| CAGGTTACAA CCTGTGAATT GTACGAGCTA GTGGAGGCCA TGGTCGAGAA | 4100 |
| GGGCCAGGAC GGCTCCGCCG TCCTTGAGCT CGACCTTTGT AGCCGCGACG | 4150 |
| TGTCCAGGAT CACCTTCTTC CAGAAAGATT GTAATAAATT CACCACGGGG | 4200 |
| GAGACCATCG CCCATGGTAA AGTGGGCCAG GGCATTTCGG CCTGGAGTAA | 4250 |
| GACCTTCTGT GCCCTTTTCG GCCCCTGGTT CCGTGCTATT GAGAAGGCTA | 4300 |
| TCCTGGCCCT GCTCCCTCAG GGTGTGTTTT ATGGGGATGC CTTTGATGAC | 4350 |
| ACCGTCTTCT CGGCGGCTGT GGCCGCAGCA AAGGCATCCA TGGTGTTCGA | 4400 |
| GAATGACTTT TCTGAGTTTG ATTCCACCCA GAATAATTTT TCCTTGGGCC | 4450 |
| TAGAGTGTGC TATTATGGAG GAGTGTGGGA TGCCGCAGTG GCTCATCCGC | 4500 |
| TTGTACCACC TTATAAGGTC TGCGTGGATT CTGCAGGCCC CGAAGGAGTC | 4550 |
| CCTGCGAGGG TTTTGGAAGA AACACTCCGG TGAGCCCGGC ACCCTTCTGT | 4600 |
| GGAATACTGT CTGGAACATG GCCGTTATCA CCCACTGTTA TGATTTCCGC | 4650 |
| GATCTGCAGG TGGCTGCCTT TAAAGGTGAT GATTCGATAG TGCTTTGCAG | 4700 |
| TGAGTACCGT CAGAGCCCAG GGGCTGCTGT CCTGATTGCT GGCTGTGGCC | 4750 |

```
TAAAGTTGAA GGTGGATTTC CGTCCGATTG GTCTGTATGC AGGTGTTGTG         4800

GTGGCCCCCG GCCTTGGCGC GCTTCCTGAT GTCGTGCGCT TCGCCGGTCG         4850

GCTTACTGAG AAGAATTGGG GCCCTGGCCC CGAGCGGGCG GAGCAGCTCC         4900

GCCTCGCTGT GAGTGATTTT CTCCGCAAGC TCACGAATGT AGCTCAGATG         4950

TGTGTGGATG TTGTCTCTCG TGTTTATGGG GTTTCCCCTG GGCTCGTTCA         5000

TAACCTGATT GGCATGCTAC AGGCTGTTGC TGATGGCAAG GCTCATTTCA         5050

CTGAGTCAGT GAAGCCAGTG CTTGACCTGA CAAATTCAAT TCTGTGTCGG         5100

GTGGAATGAA TAACATGTCT TTTGCTGCGC CCATGGGTTC GCGACCATGC         5150

GCCCTCGGCC TATTTTGCTG TTGCTCCTCA TGTTTCTGCC TATGCTGCCC         5200

GCGCCACCGC CCGGTCAGCC GTCTGGCCGC CGTCGTGGGC GGCGCAGCGG         5250

CGGTTCCGGC GGTGGTTTCT GGGGTGACCG GGTTGATTCT CAGCCCTTCG         5300

CAATCCCCTA TATTCATCCA ACCAACCCCT TCGCCCCCGA TGTCACCGCT         5350

GCGGCCGGGG CTGGACCTCG TGTTCGCCAA CCCGCCCGAC CACTCGGCTC         5400

CGCTTGGCGT GACCAGGCCC AGCGCCCCGC CGCTGCCTCA CGTCGTAGAC         5450

CTACCACAGC TGGGGCCGCG CCGCTAACCG CGGTCGCTCC GGCCCATGAC         5500

ACCCCGCCAG TGCCTGATGT TGACTCCCGC GGCGCCATCC TGCGCCGGCA         5550

GTATAACCTA TCAACATCTC CCCTCACCTC TTCCGTGGCC ACCGGCACAA         5600

ATTTGGTTCT TTACGCCGCT CCTCTTAGCC CGCTTCTACC CCTCCAGGAC         5650

GGCACCAATA CTCATATAAT GGCTACAGAA GCTTCTAATT ATGCCCAGTA         5700

CCGGGTTGCT CGTGCCACAA TTCGCTACCG CCCGCTGGTC CCCAACGCTG         5750

TTGGTGGCTA CGCTATCTCC ATTTCGTTCT GGCCACAGAC CACCACCACC         5800

CCGACGTCCG TTGACATGAA TTCAATAACC TCGACGGATG TCCGTATTTT         5850

AGTCCAGCCC GGCATAGCCT CCGAGCTTGT TATTCCAAGT GAGCGCCTAC         5900

ACTATCGCAA CCAAGGTTGG CGCTCTGTTG AGACCTCCGG GGTGGCGGAG         5950

GAGGAGGCCA CCTCTGGTCT TGTCATGCTC TGCATACATG GCTCACCTGT         6000

AAATTCTTAT ACTAATACAC CCTATACCGG TGCCCTCGGG CTGTTGGACT         6050

TTGCCCTCGA ACTTGAGTTC CGCAACCTCA CCCCCGGTAA TACCAATACG         6100

CGGGTCTCGC GTTACTCCAG CACTGCCCGT CACCGCCTTC GTCGCGGTGC         6150

AGATGGGACT GCCGAGCTCA CCACCACGGC TGCTACTCGC TTCATGAAGG         6200

ACCTCTATTT TACTAGTACT AATGGTGTTG GTGAGATCGG CCGCGGGATA         6250

GCGCTTACCC TGTTTAACCT TGCTGACACC CTGCTTGGCG GTCTACCGAC         6300

AGAATTGATT TCGTCGGCTG GTGGCCAGCT GTTCTACTCT CGCCCCGTCG         6350

TCTCAGCCAA TGGCGAGCCG ACTGTTAAGC TGTATACATC TGTGGAGAAT         6400

GCTCAGCAGG ATAAGGGTAT TGCAATCCCG CATGACATCG ACCTCGGGGA         6450

ATCCCGTGTA GTTATTCAGG ATTATGACAA CCAACATGAG CAGGACCGAC         6500

CGACACCTTC CCCAGCCCCA TCGCGTCCTT TTTCTGTCCT CCGAGCTAAC         6550

GATGTGCTTT GGCTTTCTCT CACCGCTGCC GAGTATGACC AGTCCACTTA         6600

CGGCTCTTCG ACCGGCCCAG TCTATGTCTC TGACTCTGTG ACCTTGGTTA         6650

ATGTTGCGAC CGGCGCGCAG GCCGTTGCCC GGTCACTCGA CTGGACCAAG         6700
```

```
GTCACACTTG ATGGTCGCCC CCTTTCCACC ATCCAGCAGT ATTCAAAGAC      6750

CTTCTTTGTC CTGCCGCTCC GCGGTAAGCT CTCCTTTTGG GAGGCAGGAA      6800

CTACTAAAGC CGGGTACCCT TATAATTATA ACACCACTGC TAGTGACCAA      6850

CTGCTCGTTG AGAATGCCGC TGGGCATCGG GTTGCTATTT CCACCTACAC      6900

TACTAGCCTG GGTGCTGGCC CCGTCTCTAT TTCCGCGGTT GCTGTTTTAG      6950

CCCCCCACTC TGTGCTAGCA TTGCTTGAGG ATACCATGGA CTACCCTGCC      7000

CGCGCCCATA CTTTCGATGA CTTCTGCCCG GAGTGCCGCC CCCTTGGCCT      7050

CCAGGGTTGT GCTTTTCAGT CTACTGTCGC TGAGCTTCAG CGCCTTAAGA      7100

TGAAGGTGGG TAAAACTCGG GAGTTATAGT TTATTTGCTT GTGCCCCCCT      7150

TCTTTCTGTT GCTTATTT                                         7168
```

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 5:

```
ACATTTGAAT TCACAGACAT TGTGC                                   25
```

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 6:

```
ACACAGATCT GAGCTACATT CGTGAG                                  26
```

(2) INFORMATION FOR SEQ ID NO: 7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 7:

```
AAAGGGATCC ATGGTGTTTG AGAATG                                  26
```

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 8:

```
ACTCACTGCA GAGCACTATC GAATC                                   25
```

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single (D) TOPOLOGY: linear (xi) SEQUENCE DESCRIPTION: SEQ ID NO: 9:

CGGTAAACTG GTACTGCACA AC                                            22

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 10:

AAGTCCCGCT CTATTACCCA AG                                            22

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 11:

ACCCACGGGT GTTGGTTTTT G                                             21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 12:

TTCTTGGGGC AGGTAGAGAA G                                             21

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 13:

TTATTGAATT CATGTCAACG GACGTC                                        26

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

AATAATTCAT GCCGTCGCTC C                                             21

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
       (xi) SEQUENCE DESCRIPTION: SEQ ID NO: 15:

AAGCTCAGGA AGGTACAACT C                                              21

(2) INFORMATION FOR SEQ ID NO: 16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 16:

AAATCGATGG CTGGGATCTG ATTC                                           24

(2) INFORMATION FOR SEQ ID NO: 17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 17:

GAGGCATTGT AGAGCTTTGT G                                              21

(2) INFORMATION FOR SEQ ID NO: 18:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 18:

GATGTTGCAC GGACAGCAAA TC                                             22

(2) INFORMATION FOR SEQ ID NO: 19:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 19:

ATCTCCGATG CAATCGTTAA TAAC                                           24

(2) INFORMATION FOR SEQ ID NO: 20:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 20:

TAATCCATTC TGTGGCGAGA G                                              21

(2) INFORMATION FOR SEQ ID NO: 21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear
```

(xi) SEQUENCE DESCRIPTION: SEQ ID NO: 21:

AAGTGTGACC TTGGTCCAGT C                                              21

(2) INFORMATION FOR SEQ ID NO: 22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 22:

TTGCTCGTGC CACAATTCGC TAC                                            23

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 23:

CATTTCACTG AGTCAGTGAA G                                              21

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 24:

TAATTATAAC ACCACTGCTA G                                              21

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 25:

GATTGCAATA CCCTTATCCT G                                              21

(2) INFORMATION FOR SEQ ID NO: 26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 26:

ATTAAACCTG TATAGGGCAG AAC                                            23

(2) INFORMATION FOR SEQ ID NO: 27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 27:

AAGTTCGATA GCCAGATTTG C                                           21

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 28:

TCATGTTGGT TGTCATAATC C                                           21

(2) INFORMATION FOR SEQ ID NO: 29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 29:

GATGACGCAC TTCTCAGTGT G                                           21

(2) INFORMATION FOR SEQ ID NO: 30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 30:

AGAACAACGA ACGGAGAAC                                              19

(2) INFORMATION FOR SEQ ID NO: 31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 31:

AGATCCCAGC CATCGACTTT G                                           21

(2) INFORMATION FOR SEQ ID NO: 32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 32:

TAGTAGTGTA GGTGGAAATA G                                           21

(2) INFORMATION FOR SEQ ID NO: 33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 33:

-continued

GTGTGGTTAT TCAGGATTAT G				21

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 34:

ACTCTGTGAC CTTGGTTAAT G				21

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 35:

AACTCAAGTT CGAGGGCAAA G				21

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 36:

CGCTTACCCT GTTTAACCTT G				21

(2) INFORMATION FOR SEQ ID NO: 37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 37:

ATCCCCTATA TTCATCCAAC CAAC			24

(2) INFORMATION FOR SEQ ID NO: 38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 38:

CTCCTCATGT TTCTGCCTAT G				21

(2) INFORMATION FOR SEQ ID NO: 39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 39:

GCCAGAACGA AATGGAGATA GC			22

(2) INFORMATION FOR SEQ ID NO: 40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 40:

CTCAGACATA AAACCTAAGT C                                      21

(2) INFORMATION FOR SEQ ID NO: 41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 41:

TGCCCTATAC AGGTTTAATC G                                      21

(2) INFORMATION FOR SEQ ID NO: 42:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 42:

ACCGGCATAT ACCAGGTGC                                        19

(2) INFORMATION FOR SEQ ID NO: 43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 43:

ACATGGCTCA CTCGTAAATT C                                      21

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 44:

AACATTAGAC GCGTTAACGA G                                      21

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 45:

CTCTTTTGAT GCCAGTCAGA G                                      21

```
(2) INFORMATION FOR SEQ ID NO: 46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 46:

ACCTACCCGG ATGGCTCTAA GG                                        22

(2) INFORMATION FOR SEQ ID NO: 47:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO: 47:

TATGGGAATT CGTGCCGTCC TGAAG                                     25

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 48:

AGTGGGAGCA GTATACCAGC G                                         21

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 49:

CTGCTATTGA GCAGGCTGCT C                                         21

(2) INFORMATION FOR SEQ ID NO: 50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 50:

GGGCCATTAG TCTCTAAAAC C                                         21

(2) INFORMATION FOR SEQ ID NO: 51:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 51:

GAGGTTTTCT GGAATCATC                                            19
```

(2) INFORMATION FOR SEQ ID NO: 52:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 52:

GCATAGGTGA GACTG                                      15

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 53:

AGTTACAGCC AGAAAACC                                  18

(2) INFORMATION FOR SEQ ID NO: 54:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 54:

CCATGGATCC TCGGCCTATT TTGCTGTTGC TCC                   33

(2) INFORMATION FOR SEQ ID NO: 55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 55:

AGGCAGACCA CATATGTG                                  18

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 56:

GGTGCACTCC TGACCAAGCC                              20

(2) INFORMATION FOR SEQ ID NO: 57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 57:

ATTGGCTGCC ACTTTGTTC                                 19

(2) INFORMATION FOR SEQ ID NO: 58:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 58:

ACCCTCATAC GTCACCACAA C                                        21

(2) INFORMATION FOR SEQ ID NO: 59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 59:

GCGGTGGACC ACATTAGGAT TATC                                     24

(2) INFORMATION FOR SEQ ID NO: 60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 60:

CATGATATGT CACCATCTG                                           19

(2) INFORMATION FOR SEQ ID NO: 61:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 61:

GTCATCCATA ACGAGCTGG                                           19

(2) INFORMATION FOR SEQ ID NO: 62:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 62:

AGCGGAATTC GAGGGGCGGC ATAAAGAACC AGG                           33

(2) INFORMATION FOR SEQ ID NO: 63:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 63:

GCGCTGAATT CGGATCACAA GCTCAGAGGC TATGCC                        36

(2) INFORMATION FOR SEQ ID NO: 64:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO: 64:

GTATAACGGA TCCACATCTC CCCTTACCTC                              30

(2) INFORMATION FOR SEQ ID NO: 65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 65:

TAACCTGGAT CCTTATGCCG CCCCTCTTAG                              30

(2) INFORMATION FOR SEQ ID NO: 66:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 66:

AAATTGGATC CTGTGTCGGG TGGAATGAAT AACATGTC                     38

(2) INFORMATION FOR SEQ ID NO: 67:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 67:

ATCGGCAGAT CTGATAGAGC GGGGACTTGC CGGATCC                      37

(2) INFORMATION FOR SEQ ID NO: 68:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 68:

TACCCTGCCC GCGCCCATAC TTTTGATG                                28

(2) INFORMATION FOR SEQ ID NO: 69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 69:

GGCTGAGATC TGGTTCGGGT CGCCAAGAAG GTG                          33

(2) INFORMATION FOR SEQ ID NO: 70:

(i) SEQUENCE CHARACTERISTICS:

(A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 70:

TACAGATCTA TACAACTTAA CAGTCGG                                           27

(2) INFORMATION FOR SEQ ID NO: 71:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 71:

GCGGCAGATC TCACCGACAC CATTAGTAC                                         29

(2) INFORMATION FOR SEQ ID NO: 72:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 72:

CCGTCGGATC CCAGGGGCTG CTGTCCTG                                          28

(2) INFORMATION FOR SEQ ID NO: 73:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 73:

AAAGGAATTC AAGACCAGAG GTAGCCTCCT C                                      31

(2) INFORMATION FOR SEQ ID NO: 74:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 74:

GTTGATATGA ATTCAATAAC CTCGACGG                                          28

(2) INFORMATION FOR SEQ ID NO: 75:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 75:

TTTGGATCCT CAGGGAGCGC GGAACGCAGA AATGAG                                 36

(2) INFORMATION FOR SEQ ID NO: 76:

(i) SEQUENCE CHARACTERISTICS:
        (A) LENGTH: 26 base pairs (B) TYPE: nucleic acid
            (C) STRANDEDNESS: single
            (D) TOPOLOGY: linear (xi) SEQUENCE DESCRIPTION: SEQ ID NO: 76:

TCACTCGTGA ATTCCTATAC TAATAC                                                26

(2) INFORMATION FOR SEQ ID NO: 77:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 77:

TTTGGATCCT CAGGGAGCGC GGAACGCAGA AATG                                       34

(2) INFORMATION FOR SEQ ID NO: 78:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 78:

TGATAGAGCG GGACTTGCCG GATCC                                                 25

(2) INFORMATION FOR SEQ ID NO: 79:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 79:

TTGCATTAGG TTAATGAGGA TCTC                                                  24

(2) INFORMATION FOR SEQ ID NO: 80:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 80:

ACCTGCTTCC TTCAGCCTGC AGAAG                                                 25

(2) INFORMATION FOR SEQ ID NO: 81:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 81:

GCGGTGGATC CGCTCCCAGG CGTCAAAAC                                             29

(2) INFORMATION FOR SEQ ID NO: 82:

(i) SEQUENCE CHARACTERISTICS:
            (A) LENGTH: 29 base pairs
            (B) TYPE: nucleic acid

```
            (C) STRANDEDNESS: single
            (D) TOPOLOGY: linear (xi) SEQUENCE DESCRIPTION: SEQ ID NO: 82:

GGGCGGATCG AATTCGAGAC CCTTCTTGG                                29

(2) INFORMATION FOR SEQ ID NO: 83:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 83:

AGGATGGATC CATAAGTTAC CGATCAG                                  27

(2) INFORMATION FOR SEQ ID NO: 84:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO: 84:

GGCTGGAATT CCTCTGAGGA CGCCCTCAC                                29

(2) INFORMATION FOR SEQ ID NO: 85:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 85:

GCCGAAGATC TATCGGACAT AGACCTC                                  27

(2) INFORMATION FOR SEQ ID NO: 86:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 86:

CAGACGACGG ATCCCCTTGG ATATAGCCTG                               30

(2) INFORMATION FOR SEQ ID NO: 87:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO: 87:

GGCCGAATTC AGGCAGACCA CATATGTGGT CGATGCCATG                    40

(2) INFORMATION FOR SEQ ID NO: 88:

(i) SEQUENCE CHARACTERISTICS:
            (A) LENGTH: 25 base pairs
            (B) TYPE: nucleic acid
            (C) STRANDEDNESS: single
```

-continued (D) TOPOLOGY: linear (xi) SEQUENCE DESCRIPTION: SEQ ID NO: 88:

GCAGGTGTGC CTGGATCCGG CAAGT                                              25

(2) INFORMATION FOR SEQ ID NO: 89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 89:

GTTAGAATTC CGGCCCAGCT GTGGTAGGTC                                     30

(2) INFORMATION FOR SEQ ID NO: 90:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 90:

CCGTCCGATT GGTCTGTATG CAGG                                               24

(2) INFORMATION FOR SEQ ID NO: 91:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 91:

TACCAGTTTA CTGCAGGTGT GC                                                 22

(2) INFORMATION FOR SEQ ID NO: 92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 92:

CAAGCCGATG TGGACGTTGT CG                                                 22

(2) INFORMATION FOR SEQ ID NO: 93:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 93:

GGCGCTGGGC CTGGTCACGC CAAG                                               24

(2) INFORMATION FOR SEQ ID NO: 94:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 94:

GCAGAAACTA GTGTTGACCC AG                                              22

(2) INFORMATION FOR SEQ ID NO: 95:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 95:

TAGGTCTACG ACGTGAGGCA AC                                              22

(2) INFORMATION FOR SEQ ID NO: 96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 96:

TACAATCTTT CAGGAAGAAG G                                               21

(2) INFORMATION FOR SEQ ID NO: 97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 97:

CCCACACTCC TCCATAATAG C                                               21

(2) INFORMATION FOR SEQ ID NO: 98:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 98:

GATAGTGCTT TGCAGTGAGT ACCG                                            24

(2) INFORMATION FOR SEQ ID NO: 99:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 99:

GTATAACGGA TCCACATCTC CCCTTACCTC                                      30

(2) INFORMATION FOR SEQ ID NO: 100:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued (xi) SEQUENCE DESCRIPTION: SEQ ID NO: 100:

TACAGATCTA TACAACTTAA CAGTCGG                                            27

(2) INFORMATION FOR SEQ ID NO: 101:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 101:

GCGGCAGATC TCACCGACAC CATTAGTAC                                          29

(2) INFORMATION FOR SEQ ID NO: 102:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 102:

TAACCTGGAT CCTTATGCCG CCCCTCTTAG                                         30

(2) INFORMATION FOR SEQ ID NO: 103:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 103:

GCACAACCTA GGTTACTATA ACTCCCGAGT TTTACC                                  36

(2) INFORMATION FOR SEQ ID NO: 104:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 104:

GGGTTCCCTA GGATGCGCCC TCGGCCTATT TTG                                     33

(2) INFORMATION FOR SEQ ID NO: 105:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 105:

CGTGGGCCTA GGAGCGGCGG TTCCGGCGGT GGT                                     33

(2) INFORMATION FOR SEQ ID NO: 106:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 106:

-continued

```
GCTTGGCCTA GGCAGGCCCA GCGCCCCGCC GCT                                      33

(2) INFORMATION FOR SEQ ID NO: 107:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (xi) SEQUENCE DESCRIPTION: SEQ ID NO: 107:

CCGCCACCTA GGGATGTTGA CTCCCGCGGC GCC                                      33
```